United States Patent
Dinsmore et al.

(10) Patent No.: US 9,957,265 B2
(45) Date of Patent: *May 1, 2018

(54) N-(2-CYANO HETEROCYCLYL) PYRAZOLO PYRIDONES AS JANUS KINASE INHIBITORS

(71) Applicant: Merck Sharp & Dohme Corp., Rahway, NJ (US)

(72) Inventors: Christopher Dinsmore, Newton, MA (US); Peter Fuller, Ashland, MA (US); David Guerin, Natick, MA (US); Christopher F. Thompson, Arlington, MA (US); Qinglin Pu, Needham, MA (US); Mark E. Scott, Andover, MA (US); Jason David Katz, Newton, MA (US); Ravi Kurukulasuriya, Niantic, CT (US); Joshua T. Close, Franklin, MA (US); Danielle Falcone, Brookline, MA (US); Jason Brubaker, Cambridge, MA (US); Hongbo Zeng, Westford, MA (US); Yunfeng Bai, Beijing (CN); Jianmin Fu, Beijing (CN); Norman Kong, Beijing (CN); Yumei Liu, Beijing (CN); Zhixiang Zheng, Beijing (CN)

(73) Assignee: Merck Sharp & Dohme Corp., Rahway, NJ (US)

( * ) Notice: Subject to any disclaimer, the term of this patent is extended or adjusted under 35 U.S.C. 154(b) by 109 days.

This patent is subject to a terminal disclaimer.

(21) Appl. No.: 14/778,052

(22) PCT Filed: Mar. 19, 2014

(86) PCT No.: PCT/CN2014/000298
§ 371 (c)(1),
(2) Date: Sep. 17, 2015

(87) PCT Pub. No.: WO2014/146492
PCT Pub. Date: Sep. 25, 2014

(65) Prior Publication Data
US 2016/0272633 A1    Sep. 22, 2016

Related U.S. Application Data

(60) Provisional application No. 61/803,226, filed on Mar. 19, 2013.

(51) Int. Cl.
*C07D 471/04* (2006.01)
*C07D 519/00* (2006.01)

(52) U.S. Cl.
CPC ......... *C07D 471/04* (2013.01); *C07D 519/00* (2013.01)

(58) Field of Classification Search
None
See application file for complete search history.

(56) References Cited

U.S. PATENT DOCUMENTS

| 7,049,312 | B1 | 5/2006 | Rafferty et al. |
| 7,807,653 | B2 | 10/2010 | Cook et al. |
| 2005/0208582 | A1 | 9/2005 | Ohi et al. |
| 2010/0105661 | A1 | 4/2010 | Shirakami |
| 2012/0178740 | A1 | 7/2012 | Nielsen et al. |
| 2016/0280704 | A1* | 9/2016 | Childers ............ C07D 519/00 |

FOREIGN PATENT DOCUMENTS

| CN | 1656079 A | 8/2005 |
| CN | 102574857 A | 7/2012 |
| EP | 2857400 | 4/2015 |
| JP | 4139185 | 5/1992 |
| JP | 04139185 A2 | 5/1992 |
| JP | 2003501429 | 1/2003 |
| JP | 2005525358 | 8/2005 |
| JP | 4414881 | 2/2010 |
| WO | 2011112662 A1 | 9/2011 |
| WO | 2012127506 A1 | 9/2012 |
| WO | 2013041042 A1 | 3/2013 |
| WO | 2013180265 A1 | 5/2013 |

OTHER PUBLICATIONS

Silverman, R. The Organic Chemistry of Drug Design and Drug Action 2004, NY Elsevier, pp. 29-32.*
European Search Report for EP14767458.4 dated Aug. 1, 2016, 7 pages.
International Search Report for PCT/CN2014/000298 dated Jun. 30, 2014.
Smyth, et al, Synthesis and reactivity of 3-amino-1H-pyrazolo[4,3-c]pyridin-4(5H)-ones: development of a novel kinase-focussed library, Tetrahedron, 2010, pp. 2843-2854, vol. 66.

* cited by examiner

*Primary Examiner* — Heidi Reese
(74) *Attorney, Agent, or Firm* — Patricia A. Shatynski; John C. Todaro

(57) ABSTRACT

Provided are compounds of Formula I, a JAK inhibitor, and use thereof for the treatment of JAK-mediated diseases by the application.

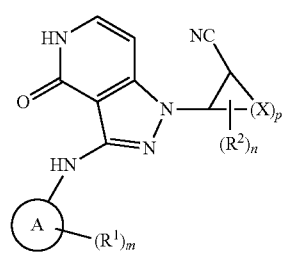

11 Claims, No Drawings

N-(2-CYANO HETEROCYCLYL) PYRAZOLO PYRIDONES AS JANUS KINASE INHIBITORS

CROSS REFERENCE TO RELATED APPLICATIONS

This application is a U.S. National Phase application under 35 U.S.C. § 371 of PCT Application No. PCT/CN2014/000298, filed Mar. 19, 2014 which claims benefit under 35 U.S.C. § 119(e) of U.S. Provisional Application No. 61/803,226 filed on Mar. 19, 2013.

BACKGROUND OF THE INVENTION

Protein kinases are a group of enzymes that regulate the activity of their target proteins by the addition of phosphate groups to the protein substrate. Kinases play an essential role in many physiological processes including cell division, differentiation, cellular homeostasis and signal transduction. Kinases can be subdivided by their target into Serine/Threonine kinases and Tyrosine kinases. Tyrosine kinases are further subdivided into receptor tyrosine kinases and non-receptor tyrosine kinases. The mammalian Janus kinase (JAK) family members are non-receptor tyrosine kinases.

The JAK family has four members; JAK1, JAK2, JAK3 and TYK2. JAK1, JAK2 and TYK2 are universally expressed, whereas JAK3 expression is limited to hematopoetic cells. The JAK family is involved in intracellular signal transduction from >70 different cytokines. Cytokines bind to their cell surface receptors resulting in receptor dimerization and subsequent activation/phosphorylation of JAK tyrosine kinases. The JAKs are either constitutively associated with the receptor or are recruited upon cytokine binding. Specific tyrosine residues on the receptor are then phosphorylated by activated JAKs and serve as docking sites for STAT proteins. STATs are phosphorylated by JAKs, dimerize, then translocate to the nucleus where they bind specific DNA elements and activate gene transcription. JAK1 signals in conjunction with all JAK isoforms in a cytokine dependent manner.

JAKs are essential for multiple physiological functions. This has been demonstrated using genetically engineered mouse models that are deficient in specific JAKs. Jak1$^{-/-}$ mice die perinatally, while Jak2$^{-/-}$ mice have deficiencies in erythropoesis and die around day E12. Jak3$^{-/-}$ mice are viable, but have a SCID phenotype with deficiencies in T cells, B cells and NK cells. TYK2$^{-/-}$ mice exhibit features of hyper IgE syndrome. These phenotypes demonstrate the essential and non-redundant roles of JAK activity in vivo (K. Ghoreschi, A. Laurence, J. J. O'Shea, *Immunol. Rev.* 228, 273 (2009)).

Furthermore, mutations in the JAK enzymes have been associated with diseases in humans. Inactivating mutations in JAK3 (or the cognate common gamma chain cytokine receptor) cause a severe SCID phenotype (J. J. O'Shea, M. Pesu, D. C. Borie, P. S. Changelian, *Nat. Rev. Drug Discov.* 3, 555 (2004)). Deletions of TYK2 result in hyper IgG syndrome and increased infection risk (Y. Minegishi et al., *Immunity.* 25, 745 (2006)). No inactivating mutations have been reported for JAK1 or JAK2, consistent with the data from mice that demonstrates that JAK1 and JAK2 deficient mice are not viable. However, several mutations that result in constitutively active JAK2 have been identified, resulting in myeloproliferative diseases and confirming the central role of JAK2 in hematopoesis (O. bdel-Wahab, *Curr. Opin. Hematol.* 18, 117 (2011)). JAK2 is the sole JAK family member involved in signal transduction of the critical hematopoetic cytokines IL-3, GMCSF, EPO and TPO.

The wealth of mouse and human genetic data demonstrating a central role for JAK kinase activity in autoimmune disease, hematopoesis and oncology has been supported by the use of pan-JAK inhibitors in clinical trials for autoimmune diseases and neoplasms (See K. Ghoreschi, et al, *Immunol. Rev.* 228, 273 (2009), and A. Quintas-Cardama, H. Kantarjian, J. Cortes, S. Verstovsek, *Nat. Rev. Drug Discov.* 10, 127 (2011)).

A considerable body of literature has accumulated that link the JAK/STAT pathway to various diseases and disorders including hyperproliferative disorders and cancer such as leukemia and lymphomas, immunological and inflammatory disorders such as transplant rejection, asthma, chronic obstructive pulmonary disease, allergies, rheumatoid arthritis, type I diabetes, amyotropic lateral sclerosis and multiple sclerosis.

SUMMARY OF THE INVENTION

The present invention provides novel compounds which are inhibitors of JAKs. The invention also provides a method for the treatment and prevention of JAK-mediated diseases and disorders using the novel compounds, as well as pharmaceutical compositions containing the compounds.

DETAILED DESCRIPTION OF THE INVENTION

The present invention provides compounds of Formula I or pharmaceutically acceptable salts, or stereoisomers thereof:

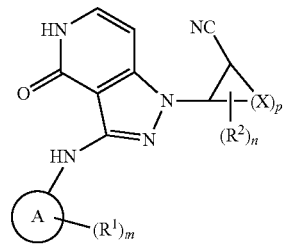

A is selected from aryl and heteroaryl;
X is independently selected from $CH_2$, NH, S, and O, wherein at least one X is other than $CH_2$;
n is 0, 1, 2, 3, or 4;
m is 0, 1, 2, 3, or 4;
p is 1, 2, 3, 4 or 5;
$R^1$ is selected from:
  halogen,
  oxo (=O),
  $C_{0-10}$ alkyliminoC$_{0-10}$ alkyl,
  $C_{1-10}$ alkyl(oxy)$_{0-1}$(carbonyl)$_{0-1}$C$_{0-10}$ alkyl,
  $C_{1-10}$ heteroalkyl(oxy)$_{0-1}$(carbonyl)$_{0-1}$C$_{0-10}$ alkyl,
  aryl C$_{0-10}$ alkyl(oxy)$_{0-1}$(carbonyl)$_{0-1}$C$_{0-10}$ alkyl,
  $C_{3-12}$ cycloalkyl C$_{0-10}$ alkyl(oxy)$_{0-1}$(carbonyl)$_{0-1}$C$_{0-10}$ alkyl,
  heteroaryl C$_{0-10}$ alkyl(oxy)$_{0-1}$(carbonyl)$_{0-1}$C$_{0-10}$ alkyl,
  $(C_{3-12})$heterocycloalkyl C$_{0-10}$ alkyl(oxy)$_{0-1}$(carbonyl)$_{0-1}$C$_{0-10}$ alkyl,
  $C_{0-10}$ alkyl(oxy)$_{0-1}$(carbonyl)$_{0-1}$ aminoC$_{0-10}$ alkyl,
  $(C_{1-10})$heteroalkyl(oxy)$_{0-1}$(carbonyl)$_{0-1}$aminoC$_{0-10}$ alkyl, $C_{3-12}$ cycloalkyl $C_{0-10}$ alkyl(oxy)$_{0-1}$(carbonyl)$_{0-1}$amino$C_{0-10}$ alkyl,
aryl $C_{0-10}$ alkyl(oxy)$_{0-1}$(carbonyl)$_{0-1}$amino$C_{0-10}$ alkyl,
heteroaryl $C_{0-10}$ alkyl(oxy)$_{0-1}$(carbonyl)$_{0-1}$amino-$C_{0-10}$ alkyl,
$(C_{3-12})$heterocycloalkyl $C_{0-10}$ alkyl(oxy)$_{0-1}$(carbonyl)$_{0-1}$amino$C_{0-10}$ alkyl,
$C_{0-10}$ alkylamino(oxy)$_{0-1}$(carbonyl)$_{0-1}C_{0-10}$ alkyl,
$(C_{1-10})$heteroalkylamino(oxy)$_{0-1}$(carbonyl)$_{0-1}C_{0-10}$ alkyl,
$C_{3-12}$ cycloalkylamino(oxy)$_{0-1}$(carbonyl)$_{0-1}C_{0-10}$ alkyl,
aryl $C_{0-10}$ alkylamino(oxy)$_{0-1}$(carbonyl)$_{0-1}C_{0-10}$ alkyl,
heteroaryl $C_{0-10}$ alkylamino(oxy)$_{0-1}$(carbonyl)$_{0-1}C_{0-10}$ alkyl,
$(C_{3-12})$heterocycloalkylamino(oxy)$_{0-1}$(carbonyl)$_{0-1}C_{0-10}$ alkyl,
$C_{0-10}$ alkylsulfonyl$C_{0-10}$ alkyl,
$C_{1-10}$ heteroalkylsulfonyl$C_{0-10}$ alkyl,
$(C_{3-12})$cycloalkyl$C_{0-10}$alkylsulfonyl$C_{0-10}$ alkyl,
$(C_{3-12})$cycloheteroalkyl$C_{0-10}$alkylsulfonyl$C_{0-10}$ alkyl,
heteroaryl$C_{0-10}$ alkylsulfonyl$C_{0-10}$ alkyl,
aryl$C_{0-10}$ alkylsulfonyl$C_{0-10}$ alkyl,
$C_{1-10}$ alkylsulfamoyl$C_{0-10}$ alkyl,
$C_{1-10}$ heteroalkylsulfamoyl$C_{0-10}$ alkyl,
$(C_{3-12})$cycloalkyl$C_{0-10}$ alkylsulfamoyl$C_{0-10}$ alkyl,
$(C_{3-12})$cycloheteroalkyl$C_{0-10}$alkylsulfamoyl$C_{0-10}$ alkyl,
heteroaryl$C_{0-10}$ alkylsulfamoyl$C_{0-10}$ alkyl,
aryl$C_{0-10}$ alkylsulfamoyl$C_{0-10}$ alkyl,
$(C_{0-10}$ alkyl$)_{1-2}$ amino,
—$CO_2(C_{0-10}$ alkyl),
—$(C_{0-10}$ alkyl)$CO_2H$,
—$SO_2NH_2$,
—$SO_2NH(C_{1-10}$ alkyl),
—$SO_2N(C_{1-10}$ alkyl)$_2$,
—$SO_2CF_3$,
—$SO_2CF_2H$,
$C_{1-10}$ alkylsulfinyl$C_{0-10}$ alkyl,
$C_{1-10}$ heteroalkylsulfinyl$C_{0-10}$alkyl,
$(C_{3-12})$cycloalkyl$C_{0-10}$alkylsulfinyl$C_{0-10}$alkyl,
$(C_{3-12})$cycloheteroalkyl$C_{0-10}$alkylsulfinyl$C_{0-10}$alkyl,
heteroaryl$C_{0-10}$ alkylsulfinyl$C_{0-10}$alkyl,
aryl$C_{0-10}$alkylsulfinyl$C_{0-10}$alkyl,
$C_{0-10}$ alkylsulfinylamino$C_{0-10}$ alkyl,
$C_{1-4}$acylamino $C_{0-10}$ alkyl,
thio$C_{1-10}$ alkyl,
hydroxy,
—$(C_{1-10}$ alkyl)OH,
—$C_{0-10}$ alkylalkoxy,
cyano,
$(C_{1-6}$alkyl)cyano, and
$C_{1-6}$haloalkyl;
$R^2$ is selected from:
halogen,
oxo (=O),
$C_{1-10}$ alkyl(oxy)$_{0-1}$(carbonyl)$_{0-1}C_{0-10}$ alkyl,
$C_{3-12}$ cycloalkyl,
$(C_{3-12})$heterocycloalkyl $C_{0-10}$ alkyl(oxy)$_{0-1}$(carbonyl)$_{0-1}C_{0-10}$ alkyl,
$C_{0-10}$ alkylamino$C_{0-10}$ alkyl,
$(C_{1-10})$heteroalkylamino$C_{0-10}$ alkyl,
$C_{3-12}$ cycloalkyl $C_{0-10}$ alkylamino$C_{0-10}$ alkyl,
aryl $C_{0-10}$ alkylamino$C_{0-10}$ alkyl,
heteroaryl $C_{0-10}$ alkylamino$C_{0-10}$ alkyl,
$(C_{3-12})$heterocycloalkyl $C_{0-10}$ alkylamino$C_{0-10}$ alkyl,
$C_{1-10}$ alkylsulfonyl,
$(C_{3-12})$cycloalkyl$C_{0-10}$alkylsulfonyl,
$(C_{3-12})$cycloheteroalkyl$C_{0-10}$alkylsulfonyl,
$(C_{0-10}$ alkyl$)_{1-2}$ amino,
—$CO_2(C_{0-10}$ alkyl),
—$(C_{0-10}$ alkyl)$CO_2H$,
—$SO_2CF_3$,
—$SO_2CF_2H$,
$C_{1-10}$ alkylsulfinyl,
hydroxy,
—$(C_{1-10}$ alkyl)OH,
—$C_{0-10}$ alkylalkoxy,
cyano,
$(C_{1-6}$alkyl)cyano, and
$C_{1-6}$haloalkyl, and
wherein $R^1$ and $R^2$ are each optionally substituted with 1, 2, 3, or 4 $R^3$ substituents;
$R^3$ is independently selected from:
halogen,
$C_{1-10}$ alkyl(oxy)$_{0-1}$(carbonyl)$_{0-1}C_{0-10}$ alkyl,
$C_{1-10}$ heteroalkyl(oxy)$_{0-1}$(carbonyl)$_{0-1}C_{0-10}$ alkyl,
aryl $C_{0-10}$ alkyl(oxy)$_{0-1}$(carbonyl)$_{0-1}C_{0-10}$ alkyl,
$C_{3-12}$ cycloalkyl $C_{0-10}$ alkyl(oxy)$_{0-1}$(carbonyl)$_{0-1}C_{0-10}$ alkyl,
heteroaryl $C_{0-10}$ alkyl(oxy)$_{0-1}$(carbonyl)$_{0-1}C_{0-10}$ alkyl,
$(C_{3-12})$heterocycloalkyl $C_{0-10}$ alkyl(oxy)$_{0-1}$(carbonyl)$_{0-1}C_{0-10}$ alkyl,
$((C_{0-10})$alkyl$)_{1-2}$aminocarbonyloxy,
aryl $(C_{0-10})$alkylaminocarbonyloxy,
—$CO_2(C_{0-10}$ alkyl),
—$(C_{0-10}$ alkyl)$CO_2H$,
oxo (=O),
—$SO_2NH_2$,
—$SO_2NH(C_{1-10}$ alkyl),
—$SO_2N(C_{1-10}$ alkyl)$_2$,
—$SO_2CF_3$,
—$SO_2CF_2H$,
$C_{1-10}$ alkylsulfinyl,
amino,
$(C_{0-10}$ alkyl$)_{1-2}$ amino,
-(oxy)$_{0-1}$(carbonyl)$_{0-1}$N$(C_{0-10}$ alkyl$)_{1-2}$
hydroxy,
$(C_{1-10}$ alkyl)OH,
$C_{1-10}$ alkoxy,
$(C_{1-10}$ alkyl)cyano,
cyano, and
$C_{1-6}$haloalkyl; and
$R^3$ is optionally substituted with 1, 2, or 3 $R^4$ substituents selected from hydroxy, $(C_{1-6})$alkyl, $(C_{1-6})$alkoxy, $(C_{1-10}$ alkyl)OH, halogen, $CO_2H$, —$(C_{0-6})$alkylCN, —$O(C=O)C_1$-$C_6$ alkyl, $NO_2$, trifluoromethoxy, trifluoroethoxy, trifluoromethyl, trifluoroethyl, —N—C(O)O$(C_{0-6})$alkyl, $C_{1-10}$ alkylsulfonyl, oxo (O=), aminosulfonyl, —$SO_2NH_2$, —$SO_2NH(C_{1-10}$ alkyl), —$SO_2N(C_{1-10}$ alkyl)$_2$, —$SO_2C_{1-6}$alkyl, —$SO_2CF_3$, —$SO_2CF_2H$, —$C_{1-10}$ alkylsulfinyl, —$O_{(0-1)}(C_{1-10})$haloalkyl, amino$(C_{1-6}$alkyl$)_{0-2}$ and $NH_2$.

Representative compounds of the instant invention include, but are not limited to the following compounds and their pharmaceutically acceptable salts and stereoisomers thereof:

3-(3-((4-(methylsulfonyl)phenyl)amino)-4-oxo-4,5-dihydro-1H-pyrazolo[4,3-c]pyridin-1-yl)tetrahydro-2H-pyran-4-carbonitrile;

3-(4-oxo-3-(phenylamino)-4,5-dihydro-1H-pyrazolo[4,3-c]pyridin-1-yl)tetrahydro-2H-pyran-4-carbonitrile;

3-(3-((2-methyl-1,1-dioxido-2,3-dihydrobenzo[d]isothiazol-5-yl)amino)-4-oxo-4,5-dihydro-1H-pyrazolo[4,3-c]pyridin-1-yl)tetrahydro-2H-pyran-4-carbonitrile;

3-(3-((2-(tert-butyl)-1,1-dioxido-2,3-dihydrobenzo[d]isothiazol-5-yl)amino)-4-oxo-4,5-dihydro-1H-pyrazolo[4,3-c]pyridin-1-yl)tetrahydro-2H-pyran-4-carbonitrile;

4-((1-(4-cyanotetrahydro-2H-pyran-3-yl)-4-oxo-4,5-dihydro-1H-pyrazolo[4,3-c]pyridin-3-yl)amino)-N,N-dimethylbenzenesulfonamide;

3-(3-((1,1-dioxido-2-(2,2,2-trifluoroethyl)-2,3-dihydrobenzo[d]isothiazol-5-yl)amino)-4-oxo-4,5-dihydro-1H-pyrazolo[4,3-c]pyridin-1-yl)tetrahydro-2H-pyran-4-carbonitrile;

3-(3-((4-(1-amino-2,2,2-trifluoroethyl)phenyl)amino)-4-oxo-4,5-dihydro-1H-pyrazolo[4,3-c]pyridin-1-yl)tetrahydro-2H-pyran-4-carbonitrile;

N-(tert-butyl)-4-((1-(4-cyanotetrahydro-2H-pyran-3-yl)-4-oxo-4,5-dihydro-1H-pyrazolo[4,3-c]pyridin-3-yl)amino)benzenesulfonamide;

3-(3-((4-(isopropylsulfonyl)phenyl)amino)-4-oxo-4,5-dihydro-1H-pyrazolo[4,3-c]pyridin-1-yl)tetrahydro-2H-pyran-4-carbonitrile;

N-(tert-butyl)-4-((1-(4-cyanotetrahydro-2H-pyran-3-yl)-4-oxo-4,5-dihydro-1H-pyrazolo[4,3-c]pyridin-3-yl)amino)-N-methylbenzenesulfonamide;

3-(3-((4-(tert-butylsulfonyl)phenyl)amino)-4-oxo-4,5-dihydro-1H-pyrazolo[4,3-c]pyridin-1-yl)tetrahydro-2H-pyran-4-carbonitrile;

3-(3-{[2-(2-methylpropyl)-2,3-dihydro-1H-isoindol-5-yl]amino}-4-oxo-4,5-dihydro-1H-pyrazolo[4,3-c]pyridin-1-yl)tetrahydro-2H-pyran-4-carbonitrile;

3-(3-{[2-(1-methylethyl)-2,3-dihydro-1H-isoindol-5-yl]amino}-4-oxo-4,5-dihydro-1H-pyrazolo[4,3-c]pyridin-1-yl)tetrahydro-2H-pyran-4-carbonitrile;

methyl 5-({1-[4-cyanotetrahydro-2H-pyran-3-yl]-4-oxo-4,5-dihydro-1H-pyrazolo[4,3-c]pyridin-3-yl}amino)-2-hydroxybenzenecarboximidoate;

3-{3-[(4-fluoro-3-methoxyphenyl)amino]-4-oxo-4,5-dihydro-1H-pyrazolo[4,3-c]pyridin-1-yl}tetrahydro-2H-pyran-4-carbonitrile;

3-[3-({4-[(1R or 1S)-1-(dimethylamino)-2,2,2-trifluoroethyl]phenyl}amino)-4-oxo-4,5-dihydro-1H-pyrazolo[4,3-c]pyridin-1-yl]tetrahydro-2H-pyran-4-carbonitrile;

3-(3-{[4-(5,5-dimethyl-3-oxo-2-oxabicyclo[2.2.2]oct-1-yl)phenyl]amino}-4-oxo-4,5-dihydro-1H-pyrazolo[4,3-c]pyridin-1-yl)tetrahydro-2H-pyran-4-carbonitrile;

3-(3-{[4-(tert-butylsulfonyl)phenyl]amino}-4-oxo-4,5-dihydro-1H-pyrazolo[4,3-c]pyridin-1-yl)oxepane-4-carbonitrile;

3-(3-{[4-(tert-butylsulfonyl)phenyl]amino}-4-oxo-4,5-dihydro-1H-pyrazolo[4,3-c]pyridin-1-yl)oxepane-4-carbonitrile;

5-(3-{[4-(tert-butylsulfonyl)phenyl]amino}-4-oxo-4,5-dihydro-1H-pyrazolo[4,3-c]pyridin-1-yl)oxepane-4-carbonitrile;

5-(3-{[4-(tert-butylsulfonyl)phenyl]amino}-4-oxo-4,5-dihydro-1H-pyrazolo[4,3-c]pyridin-1-yl)oxepane-4-carbonitrile;

3-{3-[(2-fluoropyridin-4-yl)amino]-4-oxo-4,5-dihydro-1H-pyrazolo[4,3-c]pyridin-1-yl}tetrahydro-2H-pyran-4-carbonitrile;

3-{3-[(4-cyanophenyl)amino]-4-oxo-4,5-dihydro-1H-pyrazolo[4,3-c]pyridin-1-yl}tetrahydro-2H-pyran-4-carbonitrile;

3-{3-[(4-cyano-3-fluorophenyl)amino]-4-oxo-4,5-dihydro-1H-pyrazolo[4,3-c]pyridin-1-yl}tetrahydro-2H-pyran-4-carbonitrile;

3-(4-oxo-3-((4-(1,1,1-trifluoro-2-methoxypropan-2-yl)phenyl)amino)-4,5-dihydro-1H-pyrazolo[4,3-c]pyridin-1-yl)tetrahydro-2H-pyran-4-carbonitrile;

3-(3-((2,3-dimethyl-1,1-dioxido-2,3-dihydrobenzo[d]isothiazol-5-yl)amino)-4-oxo-4,5-dihydro-1H-pyrazolo[4,3-c]pyridin-1-yl)tetrahydro-2H-pyran-4-carbonitrile;

3-(3-((4-(4,4-difluoropiperidine-1-carbonyl)-3-methylphenyl)amino)-4-oxo-4,5-dihydro-1H-pyrazolo[4,3-c]pyridin-1-yl)tetrahydro-2H-pyran-4-carbonitrile;

3-[4-oxo-3-({4-[2,2,2-trifluoro-1-(4-methylpiperazin-1-yl)ethyl]phenyl}amino)-4,5-dihydro-1H-pyrazolo[4,3-c]pyridin-1-yl]tetrahydro-2H-pyran-4-carbonitrile;

3-[4-oxo-3-({4-[2,2,2-trifluoro-1-piperazin-1-ylethyl]phenyl}amino)-4,5-dihydro-1H-pyrazolo[4,3-c]pyridin-1-yl]tetrahydro-2H-pyran-4-carbonitrile;

tert-butyl N-{1-[4-({1-[4-cyanotetrahydro-2H-pyran-3-yl]-4-oxo-4,5-dihydro-1H-pyrazolo[4,3-c]pyridin-3-yl}amino)phenyl]-2,2,2-trifluoroethyl}glycinate;

3-[4-oxo-3-({4-[2,2,2-trifluoro-1-pyrrolidin-1-ylethyl]phenyl}amino)-4,5-dihydro-1H-pyrazolo[4,3-c]pyridin-1-yl]tetrahydro-2H-pyran-4-carbonitrile;

3-[4-oxo-3-({4-[1-(2H-1,2,3-triazol-2-yl)ethyl]phenyl}amino)-4,5-dihydro-1H-pyrazolo[4,3-c]pyridin-1-yl]tetrahydro-2H-pyran-4-carbonitrile;

3-{3-[({[(2,2-dimethylcyclopropyl)amino]-2,2,2-trifluoroethyl}phenyl)amino]-4-oxo-4,5-dihydro-1H-pyrazolo[4,3-c]pyridin-1-yl}tetrahydro-2H-pyran-4-carbonitrile;

3-[3-({4-[1-(tert-butylamino)-2,2,2-trifluoroethyl]phenyl}amino)-4-oxo-4,5-dihydro-1H-pyrazolo[4,3-c]pyridin-1-yl]tetrahydro-2H-pyran-4-carbonitrile;

3-{4-oxo-3-[(4-{2,2,2-trifluoro-1-[(1-methylethyl)amino]ethyl}phenyl)amino]-4,5-dihydro-1H-pyrazolo[4,3-c]pyridin-1-yl]tetrahydro-2H-pyran-4-carbonitrile;

3-[3-({4-[1-(ethylamino)-2,2,2-trifluoroethyl]phenyl}amino)-4-oxo-4,5-dihydro-1H-pyrazolo[4,3-c]pyridin-1-yl]tetrahydro-2H-pyran-4-carbonitrile;

3-[3-({4-[1-azetidin-1-yl-2,2,2-trifluoroethyl]phenyl}amino)-4-oxo-4,5-dihydro-1H-pyrazolo[4,3-c]pyridin-1-yl]tetrahydro-2H-pyran-4-carbonitrile;

3-[3-({4-[1-(dimethylamino)-2,2,2-trifluoroethyl]phenyl}amino)-4-oxo-4,5-dihydro-1H-pyrazolo[4,3-c]pyridin-1-yl]tetrahydro-2H-pyran-4-carbonitrile;

3-(3-{[4-(1-amino-1-methylethyl)phenyl]amino}-4-oxo-4,5-dihydro-1H-pyrazolo[4,3-c]pyridin-1-yl)tetrahydro-2H-pyran-4-carbonitrile;

3-{3-[(4-{1-methyl-1-[(1-methylethyl)amino]ethyl}phenyl)amino]-4-oxo-4,5-dihydro-1H-pyrazolo[4,3-c]pyridin-1-yl}tetrahydro-2H-pyran-4-carbonitrile;

3-(3-{[1,1-dioxido-2-(2,2,2-trifluoroethyl)-2,3-dihydro-1,2-benzisothiazol-5-yl]amino}-4-oxo-4,5-dihydro-1H-pyrazolo[4,3-c]pyridin-1-yl)tetrahydro-2H-pyran-4-carbonitrile;

N-tert-butyl-4-({1-[4-cyanotetrahydro-2H-pyran-3-yl]-4-oxo-4,5-dihydro-1H-pyrazolo[4,3-c]pyridin-3-yl}amino)-N-methylbenzenesulfonamide;

tert-butyl[5-({1-[4-cyanotetrahydro-2H-pyran-3-yl]-4-oxo-4,5-dihydro-1H-pyrazolo[4,3-c]pyridin-3-yl}amino)-1,1-dioxido-1,2-benzisothiazol-2(3H)-yl]acetate;

3-[3-({4-[(1,1-dimethylpropyl)sulfonyl]phenyl}amino)-4-oxo-4,5-dihydro-1H-pyrazolo[4,3-c]pyridin-1-yl]tetrahydro-2H-pyran-4-carbonitrile;

3-[4-oxo-3-({4-[(1,1,2-trimethylpropyl)sulfonyl]phenyl}amino)-4,5-dihydro-1H-pyrazolo[4,3-c]pyridin-1-yl]tetrahydro-2H-pyran-4-carbonitrile;

5-({1-[4-cyanotetrahydro-2H-pyran-3-yl]-4-oxo-4,5-dihydro-1H-pyrazolo[4,3-c]pyridin-3-yl}amino)-N,N-dimethylpyridine-2-sulfonamide;

3-{3-[(3,4-dimethylphenyl)amino]-4-oxo-4,5-dihydro-1H-pyrazolo[4,3-c]pyridin-1-yl}tetrahydro-2H-pyran-4-carbonitrile;

3-(3-{[4-(azetidin-1-ylsulfonyl)phenyl]amino}-4-oxo-4,5-dihydro-1H-pyrazolo[4,3-c]pyridin-1-yl)tetrahydro-2H-pyran-4-carbonitrile;

3-[3-({4-[(3-methylazetidin-1-yl)sulfonyl]phenyl}amino)-4-oxo-4,5-dihydro-1H-pyrazolo[4,3-c]pyridin-1-yl]tetrahydro-2H-pyran-4-carbonitrile;

3-[3-({4-[(2,2-dimethylmorpholin-4-yl)sulfonyl]phenyl}amino)-4-oxo-4,5-dihydro-1H-pyrazolo[4,3-c]pyridin-1-yl]tetrahydro-2H-pyran-4-carbonitrile;

3-[3-({4-[(2,2-dimethylpyrrolidin-1-yl)sulfonyl]phenyl}amino)-4-oxo-4,5-dihydro-1H-pyrazolo[4,3-c]pyridin-1-yl]tetrahydro-2H-pyran-4-carbonitrile;

3-{3-[(4-{[2,6-dimethylmorpholin-4-yl]sulfonyl}phenyl)amino]-4-oxo-4,5-dihydro-1H-pyrazolo[4,3-c]pyridin-1-yl}tetrahydro-2H-pyran-4-carbonitrile;

3-{3-[(4-{[2-methylmorpholin-4-yl]sulfonyl}phenyl)amino]-4-oxo-4,5-dihydro-1H-pyrazolo[4,3-c]pyridin-1-yl}tetrahydro-2H-pyran-4-carbonitrile;

3-{3-[(4-{[2,6-dimethylmorpholin-4-yl]sulfonyl}phenyl)amino]-4-oxo-4,5-dihydro-1H-pyrazolo[4,3-c]pyridin-1-yl}tetrahydro-2H-pyran-4-carbonitrile;

3-{3-[(4-{[2-methylazetidin-1-yl]sulfonyl}phenyl)amino]-4-oxo-4,5-dihydro-1H-pyrazolo[4,3-c]pyridin-1-yl}tetrahydro-2H-pyran-4-carbonitrile;

N-(tert-butyl)-4-((1-(4-cyanotetrahydro-2H-pyran-3-yl)-4-oxo-4,5-dihydro-1H-pyrazolo[4,3-c]pyridin-3-yl)amino)-N-ethylbenzenesulfonamide;

3-[3-({4-[1-(cyclopropylamino)-2,2,2-trifluoroethyl]phenyl}amino)-4-oxo-4,5-dihydro-1H-pyrazolo[4,3-c]pyridin-1-yl]tetrahydro-2H-pyran-4-carbonitrile;

3-{3-[(4-{1-[(2,2-dimethylpropyl)amino]-2,2,2-trifluoroethyl}phenyl)amino]-4-oxo-4,5-dihydro-1H-pyrazolo[4,3-c]pyridin-1-yl}tetrahydro-2H-pyran-4-carbonitrile;

3-[3-({4-[1-(cyclopentylamino)-2,2,2-trifluoroethyl]phenyl}amino)-4-oxo-4,5-dihydro-1H-pyrazolo[4,3-c]pyridin-1-yl]tetrahydro-2H-pyran-4-carbonitrile;

3-{4-oxo-3-[(4-{2,2,2-trifluoro-1-[2-methylpyrrolidin-1-yl]ethyl}phenyl)amino]-4,5-dihydro-1H-pyrazolo[4,3-c]pyridin-1-yl}tetrahydro-2H-pyran-4-carbonitrile;

3-{4-oxo-3-[(4-{(2,2,2-trifluoro-1-[(2-methylpropyl)amino]ethyl}phenyl)amino]-4,5-dihydro-1H-pyrazolo[4,3-c]pyridin-1-yl}tetrahydro-2H-pyran-4-carbonitrile;

3-[3-({4-[1-(cyclobutylamino)-2,2,2-trifluoroethyl]phenyl}amino)-4-oxo-4,5-dihydro-1H-pyrazolo[4,3-c]pyridin-1-yl]tetrahydro-2H-pyran-4-carbonitrile;

3-(4-oxo-3-((4-(2,2,2-trifluoro-1-hydroxy-1-(pyridin-4-yl)ethyl)phenyl)amino)-4,5-dihydro-1H-pyrazolo[4,3-c]pyridin-1-yl)tetrahydro-2H-pyran-4-carbonitrile;

3-(4-oxo-3-((4-(2,2,2-trifluoro-1-hydroxy-1-(pyridin-2-yl)ethyl)phenyl)amino)-4,5-dihydro-1H-pyrazolo[4,3-c]pyridin-1-yl)tetrahydro-2H-pyran-4-carbonitrile;

3-(4-oxo-3-((4-(3-(trifluoromethyl)pyrrolidin-3-yl)phenyl)amino)-4,5-dihydro-1H-pyrazolo[4,3-c]pyridin-1-yl)tetrahydro-2H-pyran-4-carbonitrile;

3-[3-({3-methyl-3-[(1-methylethyl)amino]-2-oxo-2,3-dihydro-1H-indol-6-yl}amino)-4-oxo-4,5-dihydro-1H-pyrazolo[4,3-c]pyridin-1-yl]tetrahydro-2H-pyran-4-carbonitrile;

3-{3-[(2-methyl-1,3-benzothiazol-6-yl)amino]-4-oxo-4,5-dihydro-1H-pyrazolo[4,3-c]pyridin-1-yl}tetrahydro-2H-pyran-4-carbonitrile;

3-{3-[(3,3-dimethyl-2-oxo-2,3-dihydro-1H-indol-6-yl)amino]-4-oxo-4,5-dihydro-1H-pyrazolo[4,3-c]pyridin-1-yl}tetrahydro-2H-pyran-4-carbonitrile;

3-[4-oxo-3-({4-[(1R or 1S)-2,2,2-trifluoro-1-hydroxy-1-methylethyl]phenyl}amino)-4,5-dihydro-1H-pyrazolo[4,3-c]pyridin-1-yl]tetrahydro-2H-pyran-4-carbonitrile;

3-(3-((4-chloro-3-(methylsulfonyl)phenyl)amino)-4-oxo-4,5-dihydro-1H-pyrazolo[4,3-c]pyridin-1-yl)tetrahydro-2H-pyran-4-carbonitrile;

3-(3-((4-fluoro-3-(methylsulfinyl)phenyl)amino)-4-oxo-4,5-dihydro-1H-pyrazolo[4,3-c]pyridin-1-yl)tetrahydro-2H-pyran-4-carbonitrile, and 3-(3-{[4-chloro-3-(methylsulfinyl)phenyl]amino}-4-oxo-4,5-dihydro-1H-pyrazolo[4,3-c]pyridin-1-yl)tetrahydro-2H-pyran-4-carbonitrile.

The invention also encompasses pharmaceutical compositions containing a compound of Formula I, and methods for treatment or prevention of JAK mediated diseases using compounds of Formula I.

The invention is described using the following definitions unless otherwise indicated.

As used herein except where noted, "alkyl" is intended to include both branched- and straight-chain saturated aliphatic hydrocarbon groups, including all isomers, having the specified number of carbon atoms. Commonly used abbreviations for alkyl groups are used throughout the specification, e.g. methyl may be represented by "Me" or $CH_3$, ethyl may be represented by "Et" or $CH_2CH_3$, propyl may be represented by "Pr" or $CH_2CH_2CH_3$, butyl may be represented by "Bu" or $CH_2CH_2CH_2CH_3$, etc. "$C_{1-6}$ alkyl" (or "$C_1$-$C_6$ alkyl") for example, means linear or branched chain alkyl groups, including all isomers, having the specified number of carbon atoms. $C_{1-6}$ alkyl includes all of the hexyl alkyl and pentyl alkyl isomers as well as n-, iso-, sec- and t-butyl, n- and isopropyl, ethyl and methyl. "$C_{1-4}$ alkyl" means n-, iso-, sec- and t-butyl, n- and isopropyl, ethyl and methyl.

The term "alkylene" refers to both branched- and straight-chain saturated aliphatic hydrocarbon groups, including all isomers, having the specified number of carbons, and having two terminal end chain attachments. For illustration, the term "unsubstituted A-$C_4$alkylene-B" represents A-$CH_2$—$CH_2$—$CH_2$—$CH_2$—B.

The term "alkoxy" represents a linear or branched alkyl group of indicated number of carbon atoms attached through an oxygen bridge.

"Acyl" means a —C(O)R radical where R is optionally substituted alkyl, alkenyl, cycloalkyl, heterocycloalkyl, aryl heteroaryl, etc.

"Acylamino" means a —NRR' radical where R is H, OH, or alkoxy and R' is acyl, as defined herein.

The term "alkyl" refers to an aliphatic hydrocarbon group which may be straight or branched and having the indicated number of carbon atoms. Non-limiting examples of alkyl groups include methyl, ethyl, propyl, isopropyl, butyl, s- and t-butyl, pentyl, hexyl, and the like. The term "heteroalkyl" refers to an alkyl group where 1, 2, or 3 of the carbon atoms is substituted by a heteroatom independently chosen from N, O, or S.

"Alkenyl" refers to an aliphatic hydrocarbon group containing at least one carbon-carbon double bond and which may be straight or branched and having the indicated number of carbon atoms. Preferably alkenyl contains one carbon to carbon double bond, and up to four nonaromatic carbon-carbon double bonds may be present. Examples of alkenyl groups include ethenyl, propenyl, n-butenyl, 2-methyl-1-butenyl, 3-methylbut-2-enyl, n-pentenyl, octenyl and decenyl.

"Alkynyl" refers to an aliphatic hydrocarbon group containing at least one carbon-carbon triple bond and which may be straight or branched and having the indicated number of carbon atoms. Non-limiting examples of suitable alkynyl groups include ethynyl, propynyl, 2-butynyl and 3-methylbutynyl.

"Alkoxy" refers to an alkyl-O— group in which the alkyl group is as described above. $C_{1-6}$alkoxy, for example, includes methoxy, ethoxy, propoxy, isopropoxy, and the like.

"Alkoxyalkyl" refers to an alkyl group as described above in which one or more (in particular 1 to 3) hydrogen atoms have been replaced by alkoxy groups. Examples include $CH_2OCH_3$, $CH_2CH_2OCH_3$ and $CH(OCH_3)CH_3$.

"Aminoalkyl" refers to an alkyl group as described above in which one hydrogen atom has been replaced by an amino, monoalkylamino or dialkylamino group. Examples include $CH_2NH_2$, $CH_2CH_2NHCH_3$ and $CH(N(CH_3)_2)CH_3$.

The term "$C_0$" as employed in expressions such as "$C_{0-6}$ alkyl" means a direct covalent bond; or when the term appears at the terminus of a substituent, $C_{0-6}$ alkyl means hydrogen or C1-6alkyl. Similarly, when an integer defining the presence of a certain number of atoms in a group is equal to zero, it means that the atoms adjacent thereto are connected directly by a bond. For example, in the structure

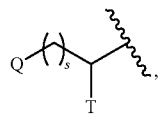

wherein s is an integer equal to zero, 1 or 2, the structure is

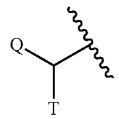

when s is zero.

The term "$C_{3-8}$ cycloalkyl" (or "$C_3$-$C_8$ cycloalkyl") means a cyclic ring of an alkane having three to eight total carbon atoms (i.e., cyclopropyl, cyclobutyl, cyclopentyl, cyclohexyl, cycloheptyl, or cyclooctyl). The terms "$C_{3-7}$ cycloalkyl", "$C_{3-6}$ cycloalkyl", "$C_{5-7}$ cycloalkyl" and the like have analogous meanings.

The term "halogen" (or "halo") refers to fluorine, chlorine, bromine and iodine (alternatively referred to as fluoro (F), chloro (Cl), bromo (Br), and iodo (I)).

The term "aryl" refers to aromatic mono- and polycarbocyclic ring systems, wherein the individual carbocyclic rings in the polyring systems are fused or attached to each other via a single bond. Suitable aryl groups include phenyl, naphthyl, 2,3-dihydro-1H-indenyl, and biphenyl.

The term "carbocycle" (and variations thereof such as "carbocyclic" or "carbocyclyl") as used herein, unless otherwise indicated, refers to (i) a $C_3$ to $C_8$ monocyclic, saturated or unsaturated ring or (ii) a $C_7$ to $C_{12}$ bicyclic saturated or unsaturated ring system. Each ring in (ii) is either independent of, or fused to, the other ring, and each ring is saturated or unsaturated. The carbocycle may be attached to the rest of the molecule at any carbon atom which results in a stable compound. The fused bicyclic carbocycles are a subset of the carbocycles; i.e., the term "fused bicyclic carbocycle" generally refers to a $C_7$ to $C_{10}$ bicyclic ring system in which each ring is saturated or unsaturated and two adjacent carbon atoms are shared by each of the rings in the ring system. A fused bicyclic carbocycle in which one ring is saturated and the other is saturated is a saturated bicyclic ring system. A fused bicyclic carbocycle in which one ring is benzene and the other is saturated is an unsaturated bicyclic ring system. A fused bicyclic carbocycle in which one ring is benzene and the other is unsaturated is an unsaturated ring system. Saturated carbocyclic rings are also referred to as cycloalkyl rings, e.g., cyclopropyl, cyclobutyl, etc. Unless otherwise noted, carbocycle is unsubstituted or substituted with $C_{1-6}$ alkyl, $C_{1-6}$ alkenyl, $C_{1-6}$ alkynyl, aryl, halogen, $NH_2$ or OH. A subset of the fused bicyclic unsaturated carbocycles are those bicyclic carbocycles in which one ring is a benzene ring and the other ring is saturated or unsaturated, with attachment via any carbon atom that results in a stable compound. Representative examples of this subset include the following:

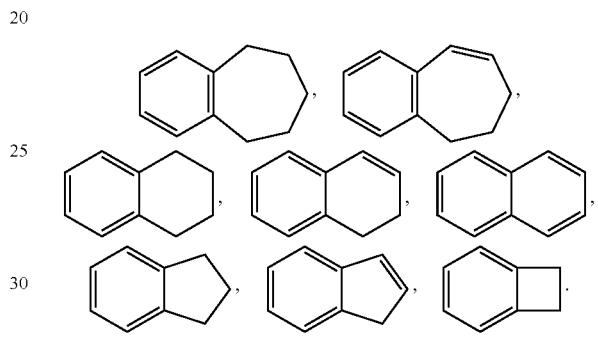

"Cyanoalkyl" refers to an alkyl group as described above in which one hydrogen atom has been replaced by a cyano group. Examples include $CH_2CN$, $CH_2CH_2CN$ and $CH(CN)CH_3$.

"Cycloalkyl" means a carbocyclic ring system having 3 to 12 ring carbon atoms; said ring system may be (a) a monocyclic saturated carbocycle optionally fused to a benzene or a partially unsaturated carbocycle, or (b) a bicyclic saturated carbocycle. For a bicyclic system, within either (a) or (b), the rings are fused across two adjacent ring carbon atoms (e.g., decalin), at one ring carbon atom (e.g., spiro [2.2]pentane), or are bridged groups (e.g., norbornane). Additional examples within the above meaning include, but are not limited to, cyclopropane, cyclobutane, cyclopentane, cyclohexane, perhydroindan, decalin, spiro[4.5]decane, bicyclo[2.2.2]octane, and the like.

"Haloalkyl" refers to an alkyl group as described above wherein one or more (in particular 1 to 5) hydrogen atoms have been replaced by halogen atoms, with up to complete substitution of all hydrogen atoms with halo groups. $C_{1-6}$ haloalkyl, for example, includes —$CF_3$, —$CF_2CF_3$, —$CH_2CF_3$, $CHFCH_3$, and the like.

"Heterocycle", "heterocyclic" or "heterocyclyl" represents a monocyclic or bicyclic 3-12 membered ring system in which at least one ring is non-aromatic (saturated or partially unsaturated) and containing at least one heteroatom selected from O, S and N. In a bicyclic ring system, the second ring may be a heteroaryl, heterocycle or a saturated, partially unsaturated or aromatic carbocycle, and the point(s) of attachment to the rest of the molecule may be on either ring. "Heterocyclyl" therefore includes heteroaryls, as well as dihydro and tetrahydro analogs thereof. Attachment of a heterocyclyl substituent can occur via a carbon atom or via a heteroatom.

Examples of heterocycles (heterocyclyl) include, but are not limited to, azetidinyl, pyrrolidinyl, piperidinyl, piperazinyl, morpholinyl, thiamorpholinyl, tetrahydrofuranyl, dihydrofuranyl, tetrahydrothienyl, tetrahydropyranyl, dihydropyranyl, dihydroimidazolyl, dihydroindolyl, 1,2,3,4-tetrahydroisoquinolinyl, 5,6,7,8-tetrahydroimidazo[1,2-a]pyrazine, 2,3-dihydrobenzofuranyl, benzo-1,4-dioxanyl, benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridinyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, aziridinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof.

Saturated heterocyclics form a subset of the heterocycles; i.e., the terms "saturated heterocyclic and $(C_{3-12})$heterocycloalkyl" generally refers to a heterocycle as defined above in which the entire ring system (whether mono- or polycyclic) is saturated. The term "saturated heterocyclic ring" refers to a 4- to 8-membered saturated monocyclic ring or a stable 7- to 12-membered bicyclic ring system which consists of carbon atoms and one or more heteroatoms selected from N, O and S. Representative examples include piperidinyl, piperazinyl, azepanyl, pyrrolidinyl, pyrazolidinyl, imidazolidinyl, oxazolidinyl, isoxazolidinyl, morpholinyl, thiomorpholinyl, thiazolidinyl, isothiazolidinyl, and tetrahydrofuryl (or tetrahydrofuranyl)

Heteroaromatics form another subset of the heterocycles; i.e., the term "heteroaromatic" (alternatively "heteroaryl") generally refers to a heterocycle as defined above in which the entire ring system (whether mono- or poly-cyclic) is an aromatic ring system. The term "heteroaromatic ring" refers a 5- or 6-membered monocyclic aromatic ring or a 7- to 12-membered bicyclic which consists of carbon atoms and one or more heteroatoms selected from N, O and S. For a bicyclic heteroaryl only one of the rings need to be heteroaromatic, the second ring may be a heteroaromatic or an aromatic, saturated, or partially unsaturated carbocycle, and the point(s) of attachment to the rest of the molecule may be on either ring. In the case of substituted heteroaryl rings containing at least one nitrogen atom (e.g., pyridine), such substitutions can be those resulting in N-oxide formation. Examples of heteroaryl include, but are not limited to, furanyl, thienyl (or thiophenyl), pyrrolyl, imidazolyl, pyrazolyl, oxazolyl, thiazolyl, isoxazolyl, isothiazolyl, triazolyl, oxadiazolyl, thiadiazolyl, tetrazolyl, pyridyl, pyrimidinyl, pyrazinyl, pyridazinyl, triazinyl, quinolinyl, isoquinolinyl, naphthyridinyl, benzothienyl, benzofuranyl, benzimidazole, benzpyrazolyl, indolyl, isoindolyl, indolizinyl, indazolyl, purinyl, quinolizinyl, phthalazinyl, quinoxalinyl, quinazolinyl, benzoxazolyl, benzisoxazolyl, 5,6,7,8-tetrahydroquinolinyl, imidazo[1,2-c]pyridinyl, imidazo[1,2-c]-pyrimidinyl, 5,6-dihydropyrrolo[1,2-b]pyrazolyl, pyrrolo[3,2-c]pyridinyl, pyrrolo[2,3-b]pyridinyl, thieno[2,3-b]pyrrolyl, furopyridine and thienopyridine.

Representative examples of bicyclic heterocycles include benzotriazolyl, indolyl, isoindolyl, indazolyl, indolinyl, isoindolinyl, quinoxalinyl, quinazolinyl, cinnolinyl, chromanyl, isochromanyl, tetrahydroquinolinyl, quinolinyl, tetrahydroisoquinolinyl, isoquinolinyl, 2,3-dihydrobenzofuranyl, 2,3-dihydrobenzo-1,4-dioxinyl (i.e., 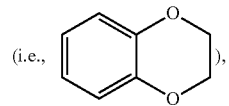), imidazo(2,1-b)(1,3)thiazole, (i.e., 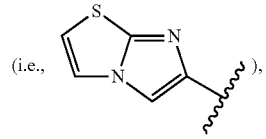), and benzo-1,3-dioxolyl (i.e., 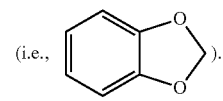).

In certain contexts herein,

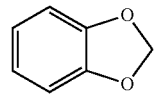

is alternatively referred to as phenyl having as a substituent methylenedioxy attached to two adjacent carbon atoms.

Non-limiting examples of substituted heteroaryls include: isoindolinone, isoindolin-1-one, 2,3-dihydro-1H-pyrazolo[4,3-c]pyridin-4(5H)-one, 2,3,4,5-tetrahydrobenzo[d]isothiazole 1,1-dioxide, and 2,3,4,5-tetrahydrobenzo[b]thiophene 1,1-dioxide.

"Hydroxyalkyl" refers to an alkyl group as described above in which one or more (in particular 1 to 3) hydrogen atoms have been replaced by hydroxy groups. Examples include $CH_2OH$, $CH_2CHOH$ and $CHOHCH_3$.

The term "imino" refers to a bivalent group =NH united to an alkyl or other non-acidic radicals, such as for example, iminomethyl (.HC=NH).

"Alkylene," "alkenylene," "alkynylene," "cycloalkylene," "arylene," "heteroarylene," and "heterocyclylene" refer to a divalent radical obtained by the removal of one hydrogen atom from an alkyl, alkenyl, alkynyl, cycloalkyl, aryl, heteroaryl, and heterocyclyl group, respectively, each of which is as defined above.

Unless expressly stated to the contrary, an "unsaturated" ring is a partially or fully unsaturated ring. For example, an "unsaturated monocyclic $C_6$ carbocycle" refers to cyclohexene, cyclohexadiene, and benzene.

Unless expressly stated to the contrary, all ranges cited herein are inclusive. For example, a heterocycle described as containing from "1 to 4 heteroatoms" means the heterocycle can contain 1, 2, 3 or 4 heteroatoms.

When any variable occurs more than one time in any constituent or in any Formula depicting and describing compounds of the invention, its definition on each occurrence is independent of its definition at every other occurrence. Also, combinations of substituents and/or variables are permissible only if such combinations result in stable compounds.

The term "sulfamoyl" is a suffix to denote radicals derived from sulfamide such as —SO$_2$NH$_2$, —SO$_2$NHR and —SO$_2$N(RR$^1$).

The term "substituted" (e.g., as in "aryl which is optionally substituted with one or more substituents . . . ") includes mono- and poly-substitution by a named substituent to the extent such single and multiple substitution (including multiple substitution at the same site) is chemically allowed.

The term "oxy" means an oxygen (O) atom. The term "thio" means a sulfur (S) atom. The term "oxo" means "=O". The term "carbonyl" means "C=O."

When any variable (e.g., R$^2$, R$^3$, etc.) occurs more than one time in any substituent or in Formula I its definition in each occurrence is independent of its definition at every other occurrence. Also, combinations of substituents and/or variables are permissible only if such combinations result in stable compounds.

Under standard nomenclature used throughout this disclosure, the terminal portion of the designated side chain is described first, followed by the adjacent functionality toward the point of attachment. For example, a C$_{1-5}$ alkyl-carbonylamino C$_{1-6}$ alkyl substituent is equivalent to

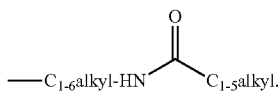

In choosing compounds of the present invention, one of ordinary skill in the art will recognize that the various substituents, i.e. R$^1$, R$^2$, R$^3$, etc., are to be chosen in conformity with well-known principles of chemical structure connectivity.

Lines drawn into the ring systems from substituents indicate that the indicated bond can be attached to any of the substitutable ring atoms. If the ring system is polycyclic, it is intended that the bond be attached to any of the suitable carbon atoms on the proximal ring only.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups can be on the same carbon or on different carbons, so long as a stable structure results. The phrase "optionally substituted with one or more substituents" should be taken to be equivalent to the phrase "optionally substituted with at least one substituent" and in such cases one embodiment will have from zero to three substituents.

Structural representations of compounds having substituents terminating with a methyl group may display the terminal methyl group either using the characters "CH$_3$", e.g. "—CH$_3$," or using a straight line representing the presence of the methyl group, e.g., "—", i.e.,

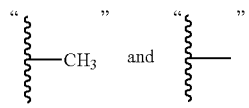

have equivalent meanings

For variable definitions containing terms having repeated terms, e.g., (CR$^i$R$^j$)$_r$, where r is the integer 2, R$^i$ is a defined variable, and R$^j$ is a defined variable, the value of R$^i$ may differ in each instance in which it occurs, and the value of R$^j$ may differ in each instance in which it occurs. For example, if R$^i$ and R$^j$ are independently selected from the group consisting of methyl, ethyl, propyl and butyl, then (CR$^i$R$^j$)$_2$ can be

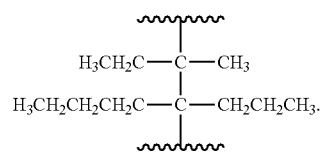

"Patient" includes both human and animals.

"Mammal" means humans and other mammalian animals.

"Therapeutically effective amount" means that amount of a drug or pharmaceutical agent that will elicit the biological or medical response of a tissue, a system, animal or human that is being sought by a researcher, veterinarian, medical doctor or other clinician.

The term "treatment" or "treating" includes alleviating, ameliorating, relieving or otherwise reducing the signs and symptoms associated with a disease or disorder.

The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I, and pharmaceutically acceptable excipients.

The term "optionally substituted" means "unsubstituted or substituted," and therefore, the generic structural formulas described herein encompasses compounds containing the specified optional substituent as well as compounds that do not contain the optional substituent.

Each variable is independently defined each time it occurs within the generic structural formula definitions. For example, when there is more than one substituent for aryl/heteroaryl, each substituent is independently selected at each occurrence, and each substituent can be the same or different from the other(s). As another example, for the group —(CR$^3$R$^3$)$_2$—, each occurrence of the two R$^3$ groups may be the same or different. As used herein, unless explicitly stated to the contrary, each reference to a specific compound of the present invention or a generic formula of compounds of the present invention is intended to include the compound(s) as well as pharmaceutically acceptable salts thereof.

In one embodiment of the invention, The present invention provides compounds of Formula I or pharmaceutically acceptable salts, or stereoisomers thereof:

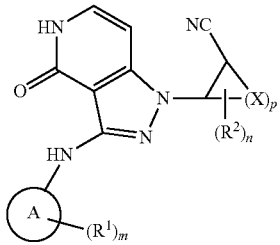

I

A is selected from aryl and heteroaryl;
X is independently selected from $CH_2$, NH, S, and O, wherein at least one X is other than $CH_2$;
n is 0, 1, 2, 3, or 4;
m is 0, 1, 2, 3, or 4;
p is 1, 2, 3, 4 or 5;
$R^1$ is selected from:
halogen,
oxo (=O),
$C_{1-10}$ alkyl(oxy)$_{0-1}$(carbonyl)$_{0-1}C_{0-10}$ alkyl,
$C_{1-10}$ heteroalkyl(oxy)$_{0-1}$(carbonyl)$_{0-1}C_{0-10}$ alkyl,
aryl $C_{0-10}$ alkyl(oxy)$_{0-1}$(carbonyl)$_{0-1}C_{0-10}$ alkyl,
$C_{3-12}$ cycloalkyl $C_{0-10}$ alkyl(oxy)$_{0-1}$(carbonyl)$_{0-1}C_{0-10}$ alkyl,
heteroaryl $C_{0-10}$ alkyl(oxy)$_{0-1}$(carbonyl)$_{0-1}C_{0-10}$ alkyl,
$(C_{3-12})$heterocycloalkyl $C_{0-10}$ alkyl(oxy)$_{0-1}C_{0-10}$ alkyl,
$C_{0-10}$ alkyl(oxy)$_{0-1}$(carbonyl)$_{0-1}$ amino$C_{0-10}$ alkyl,
$(C_{1-10})$heteroalkyl(oxy)$_{0-1}$(carbonyl)$_{0-1}$ amino$C_{0-10}$ alkyl,
$C_{3-12}$ cycloalkyl $C_{0-10}$ alkyl(oxy)$_{0-1}$(carbonyl)$_{0-1}$ amino$C_{0-10}$ alkyl,
aryl $C_{0-10}$ alkyl(oxy)$_{0-1}$(carbonyl)$_{0-1}$ amino$C_{0-10}$ alkyl,
heteroaryl $C_{0-10}$ alkyl(oxy)$_{0-1}$(carbonyl)$_{0-1}$amino$C_{0-10}$ alkyl,
$(C_{3-12})$heterocycloalkyl $C_{0-10}$ alkyl(oxy)$_{0-1}$(carbonyl)$_{0-1}$amino$C_{0-10}$ alkyl,
$C_{0-10}$ alkylamino(oxy)$_{0-1}$(carbonyl)$_{0-1}C_{0-10}$ alkyl,
$(C_{1-10})$heteroalkylamino(oxy)$_{0-1}$(carbonyl)$_{0-1}C_{0-10}$ alkyl,
$C_{3-12}$ cycloalkylamino(oxy)$_{0-1}$(carbonyl)$_{0-1}C_{0-10}$ alkyl,
aryl $C_{0-10}$ alkylamino(oxy)$_{0-1}$(carbonyl)$_{0-1}C_{0-10}$ alkyl,
heteroaryl $C_{0-10}$ alkylamino(oxy)$_{0-1}$(carbonyl)$_{0-1}C_{0-10}$ alkyl,
$(C_{3-12})$heterocycloalkylamino(oxy)$_{0-1}$(carbonyl)$_{0-1}C_{0-10}$ alkyl,
$C_{0-10}$ alkylsulfonyl$C_{0-10}$ alkyl,
$C_{1-10}$ heteroalkylsulfonyl$C_{0-10}$ alkyl,
$(C_{3-12})$cycloalkyl$C_{0-10}$alkylsulfonyl$C_{0-10}$ alkyl,
$(C_{3-12})$cycloheteroalkyl$C_{0-10}$alkylsulfonyl$C_{0-10}$ alkyl,
heteroaryl$C_{0-10}$ alkylsulfonyl$C_{0-10}$ alkyl,
aryl$C_{0-10}$ alkylsulfonyl$C_{0-10}$ alkyl,
$C_{1-10}$ alkylsulfamoyl$C_{0-10}$ alkyl,
$C_{1-10}$ heteroalkylsulfamoyl$C_{0-10}$ alkyl,
$(C_{3-12})$cycloalkyl$C_{0-10}$ alkylsulfamoyl$C_{0-10}$ alkyl,
$(C_{3-12})$cycloheteroalkyl$C_{0-10}$alkylsulfamoyl$C_{0-10}$ alkyl,
heteroaryl$C_{0-10}$ alkylsulfamoyl$C_{0-10}$ alkyl,
aryl$C_{0-10}$ alkylsulfamoyl$C_{0-10}$ alkyl,
$(C_{0-10}$ alkyl$)_{1-2}$ amino,
—$CO_2(C_{0-10}$ alkyl),
—$(C_{0-10}$ alkyl)$CO_2H$,
—$SO_2NH_2$,
—$SO_2NH(C_{1-10}$ alkyl),
—$SO_2N(C_{1-10}$ alkyl)$_2$,
—$SO_2CF_3$,
—$SO_2CF_2H$,
$C_{1-10}$ alkylsulfinyl$C_{0-10}$ alkyl,
$C_{1-10}$ heteroalkylsulfinyl$C_{0-10}$alkyl,
$(C_{3-12})$cycloalkyl$C_{0-10}$alkylsulfinyl$C_{0-10}$alkyl,
$(C_{3-12})$cycloheteroalkyl$C_{0-10}$alkylsulfinyl$C_{0-10}$alkyl,
heteroaryl$C_{0-10}$ alkylsulfinyl$C_{0-10}$alkyl,
aryl$C_{0-10}$alkylsulfinyl$C_{0-10}$alkyl,
$C_{0-10}$ alkylsulfinylamino$C_{0-10}$alkyl,
$C_{1-4}$acylamino $C_{0-10}$ alkyl,
hydroxy,
—$(C_{1-10}$ alkyl)OH,
—$C_{0-10}$ alkylalkoxy,
cyano,
$(C_{1-6}$alkyl)cyano, and
$C_{1-6}$haloalkyl;
$R^2$ is selected from
halogen,
oxo (=O),
$C_{1-10}$ alkyl(oxy)$_{0-1}$(carbonyl)$_{0-1}C_{0-10}$ alkyl,
$C_{3-12}$ cycloalkyl,
$(C_{3-12})$heterocycloalkyl $C_{0-10}$ alkyl(oxy)$_{0-1}$(carbonyl)$_{0-1}C_{0-10}$ alkyl,
$C_{0-10}$ alkylamino$C_{0-10}$ alkyl,
$(C_{1-10})$heteroalkylamino$C_{0-10}$alkyl,
$C_{3-12}$ cycloalkyl $C_{0-10}$ alkylamino$C_{0-10}$ alkyl,
aryl $C_{0-10}$ alkylamino$C_{0-10}$ alkyl,
heteroaryl $C_{0-10}$ alkylamino$C_{0-10}$ alkyl,
$(C_{3-12})$heterocycloalkyl $C_{0-10}$ alkylamino$C_{0-10}$ alkyl,
$C_{1-10}$ alkylsulfonyl,
$(C_{3-12})$cycloalkyl$C_{0-10}$ alkylsulfonyl,
$(C_{3-12})$cycloheteroalkyl$C_{0-10}$alkylsulfonyl,
$(C_{0-10}$ alkyl$)_{1-2}$ amino,
—$CO_2(C_{0-10}$ alkyl),
—$(C_{0-10}$ alkyl)$CO_2H$,
—$SO_2CF_3$,
—$SO_2CF_2H$,
$C_{1-10}$ alkylsulfinyl,
hydroxy,
—$(C_{1-10}$ alkyl)OH,
—$C_{0-10}$ alkylalkoxy,
cyano,
$(C_{1-6}$alkyl)cyano, and
$C_{1-6}$haloalkyl, and
wherein $R^1$ and $R^2$ are each optionally substituted with 1, 2, 3, or 4 $R^3$ substituents;
$R^3$ is independently selected from:
halogen,
$C_{1-10}$ alkyl(oxy)$_{0-1}$(carbonyl)$_{0-1}C_{0-10}$ alkyl,
$C_{1-10}$ heteroalkyl(oxy)$_{0-1}$(carbonyl)$_{0-1}C_{0-10}$ alkyl,
aryl $C_{0-10}$ alkyl(oxy)$_{0-1}$(carbonyl)$_{0-1}C_{0-10}$ alkyl,
$C_{3-12}$ cycloalkyl $C_{0-10}$ alkyl(oxy)$_{0-1}$(carbonyl)$_{0-1}C_{0-10}$ alkyl,
heteroaryl $C_{0-10}$ alkyl(oxy)$_{0-1}$(carbonyl)$_{0-1}C_{0-10}$ alkyl,
$(C_{3-12})$heterocycloalkyl $C_{0-10}$ alkyl(oxy)$_{0-1}C_{0-10}$ alkyl,
$((C_{0-10})$alkyl$)_{1-2}$aminocarbonyloxy,
aryl $(C_{0-10})$alkylaminocarbonyloxy,
—$CO_2(C_{0-10}$ alkyl),
—$(C_{0-10}$ alkyl)$CO_2H$,
oxo (=O),
—$SO_2NH_2$,
—$SO_2NH(C_{1-10}$ alkyl),
—$SO_2N(C_{1-10}$ alkyl)$_2$,
—$SO_2CF_3$, —SO$_2$CF$_2$H,
C$_{1-10}$ alkylsulfinyl,
amino,
(C$_{0-10}$ alkyl)$_{1-2}$ amino,
-(oxy)$_{0-1}$(carbonyl)$_{0-1}$N(C$_{0-10}$ alkyl)$_{1-2}$
hydroxy,
(C$_{1-10}$ alkyl)OH,
C$_{1-10}$ alkoxy,
(C$_{1-10}$ alkyl)cyano,
cyano, and
C$_{1-6}$haloalkyl; and
R$^3$ is optionally substituted with 1, 2, or 3 R$^4$ substituents selected from hydroxy, (C$_{1-6}$)alkyl, (C$_{1-6}$)alkoxy, (C$_{1-10}$ alkyl)OH, halogen, CO$_2$H, —(C$_{0-6}$)alkylCN, —O(C=O)C$_1$-C$_6$ alkyl, NO$_2$, trifluoromethoxy, trifluoroethoxy, trifluoromethyl, trifluoroethyl, —N=C(O)O(C$_{0-6}$)alkyl, C$_{1-10}$ alkylsulfonyl, oxo (O=), aminosulfonyl, —SO$_2$NH$_2$, —SO$_2$NH(C$_{1-10}$ alkyl), —SO$_2$N(C$_{1-10}$ alkyl)$_2$, —SO$_2$C$_{1-6}$alkyl, —SO$_2$CF$_3$, —SO$_2$CF$_2$H, —C$_{1-10}$ alkylsulfinyl, —O$_{(0-1)}$(C$_{1-10}$)haloalkyl, amino(C$_{1-6}$alkyl)$_{1-2}$ and NH$_2$.

In one embodiment of the invention, A is selected from phenyl, pyridinyl, isoindolinyl, 6,7-dihydrobenzo[d]thiazolyl, 2,3-dihydro-1H-indolyl, dihydrobenzo[d]thiazolyl, indolyl, 1,3-benzothiazolyl, benzodioxolyl, benzo[d][1,3]dioxolyl, 2,3-dihydroisoindolyl, quinolinyl, quinoxalinyl, dihydrobenzisothiazolyl, 2,3-dihydrobenzo[d]isothiazolyl, dihydroindenyl, dihydrobenzofuranyl, 2,3-dihydrobenzofuranyl, 2,3-dihydro-1H-indenyl, isoindolyl, dihydrobenzo[b]thiophenyl, 2,3-dihydrobenzo[b]thiophenyl, and

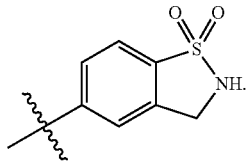 [SMILES: *c1ccc2c(c1)CNS2(=O)=O]

In another embodiment, A is selected from phenyl, pyridinyl, isoindolinyl, indolyl, 1,3-benzothazolyl, benzodioxolyl, benzo[d][1,3]dioxolyl, dihydroisoindolyl, quinolinyl, quinoxalinyl, dihydrobenzisothiazolyl, 2,3-dihydrobenzo[d]isothiazolyl, dihydroindenyl, dihydrobenzofuranyl, 2,3-dihydrobenzofuranyl, 2,3-dihydro-1H-indenyl, isoindolyl, dihydrobenzo[b]thiophenyl, 2,3-dihydrobenzo[b]thiophenyl and

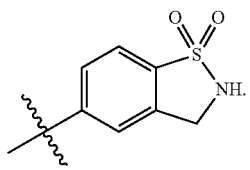 [SMILES: *c1ccc2c(c1)CNS2(=O)=O]

In one embodiment of the invention, A is selected from phenyl, pyridinyl, benzodioxolyl, benzo[d][1,3]dioxolyl, dihydroisoindolyl, quinolinyl, quinoxalinyl, dihydrobenzisothiazolyl, 2,3-dihydrobenzo[d]isothiazolyl, dihydroindenyl, dihydrobenzofuranyl, 2,3-dihydrobenzofuranyl, 2,3-dihydro-1H-indenyl, isoindolyl, and dihydrobenzo[b]thiophenyl, 2,3-dihydrobenzo[b]thiophenyl.

In yet another embodiment of the invention, A is selected from phenyl, pyridinyl, 2,3-dihydro-1H-indolyl, 1,3-benzothiazolyl, 2,3-dihydroisoindolyl, dihydrobenzisothiazolyl, 2,3-dihydrobenzo[d]isothiazolyl, and

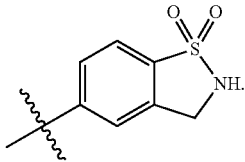 [SMILES: *c1ccc2c(c1)CNS2(=O)=O]

In another embodiment of the invention, A is selected from phenyl, dihydrobenzisothiazolyl, and 2,3-dihydrobenzo[d]isothiazolyl.

In one embodiment p is 2, 3, 4, or 5. In a variant of this embodiment, p is 3, 4, or 5. In another variant, p is 4, or 5.
In one embodiment, m is 0. In another embodiment of the invention m is 1, 2, or 3.
In one embodiment, n is 0. In another embodiment of the invention n is 1, 2, or 3.
In one embodiment, X is selected from CH$_2$ and O, wherein at least one X is other than CH$_2$. In a variant of this embodiment only one X is O.
In one embodiment, X is selected from CH$_2$, NH, and S, wherein at least one X is other than CH$_2$.
In one embodiment the ring system found in Formula I formed by

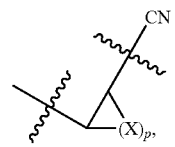

is selected from tetrahydropyranyl, piperidinyl, and azetidinyl. In a variant of this embodiment, the ring system is tetrahydropyranyl.

In one embodiment the ring system found in Formula I formed by

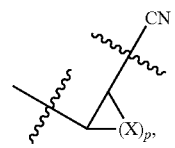

is selected from tetrahydropyranyl, oxepanyl, piperidinyl, and azetidinyl. In a variant of this embodiment, the ring system is oxepanyl or tetrahydropyranyl.

In one embodiment, R$^1$ is selected from: halogen, oxo (=O), C$_{1-10}$ alkyl(oxy)$_{0-1}$(carbonyl)$_{0-1}$C$_{0-10}$ alkyl, C$_{1-10}$ heteroalkyl(oxy)$_{0-1}$(carbonyl)$_{0-1}$C$_{0-10}$ alkyl, aryl C$_{0-10}$ alkyl(oxy)$_{0-1}$(carbonyl)$_{0-1}$C$_{0-10}$ alkyl, C$_{3-12}$ cycloalkyl C$_{0-10}$ alkyl(oxy)$_{0-1}$(carbonyl)$_{0-10}$ alkyl, heteroaryl C$_{0-10}$ alkyl(oxy)$_{0-1}$(carbonyl)$_{0-1}$C$_{0-10}$ alkyl, (C$_{3-12}$)heterocycloalkyl C$_{0-10}$ alkyl(oxy)$_{0-1}$(carbonyl)$_{0-1}$C$_{0-10}$ alkyl, C$_{0-10}$ alkyl(oxy)$_{0-10}$(carbonyl)$_{0-1}$ aminoC$_{0-10}$ alkyl, aryl C$_{0-10}$ alkyl(oxy)$_{0-1}$(carbonyl)$_{0-1}$ aminoC$_{0-10}$ alkyl, heteroaryl C$_{0-10}$ alkyl(oxy)$_{0-1}$(carbonyl)$_{0-1}$aminoC$_{0-10}$ alkyl, C$_{0-10}$ alkylamino(oxy)$_{0-1}$(carbonyl)$_{0-1}$C$_{0-10}$ alkyl, aryl C$_{0-10}$ alkylamino(oxy)$_{0-1}$(carbonyl)$_{0-1}$C$_{0-10}$ alkyl, heteroaryl C$_{0-10}$ alkylamino(oxy)$_{0-1}$(carbonyl)$_{0-1}$C$_{0-10}$ alkyl, C$_{0-10}$ alkylsulfonylC$_{0-10}$ alkyl, C$_{1-10}$ heteroalkylsulfonylC$_{0-10}$ alkyl, (C$_{3-12}$)

cycloalkyl$C_{0-10}$alkylsulfonyl$C_{0-10}$ alkyl, ($C_{3-12}$) cycloheteroalkyl$C_{0-10}$alkylsulfonyl$C_{0-10}$ alkyl, heteroaryl$C_{0-10}$ alkylsulfonyl$C_{0-10}$ alkyl, aryl$C_{0-10}$ alkylsulfonyl$C_{0-10}$ alkyl, $C_{1-10}$ alkylsulfamoyl$C_{0-10}$ alkyl, $C_{1-10}$ heteroalkylsulfamoyl$C_{0-10}$ alkyl, ($C_{3-12}$)cycloalkyl$C_{0-10}$ alkylsulfamoyl$C_{0-10}$ alkyl, ($C_{3-12}$)cycloheteroalkyl$C_{0-10}$alkylsulfamoyl$C_{0-10}$ alkyl, heteroaryl$C_{0-10}$ alkylsulfamoyl$C_{0-10}$ alkyl, aryl$C_{0-10}$ alkylsulfamoyl$C_{0-10}$ alkyl, ($C_{0-10}$ alkyl)$_{1-2}$ amino, —SO$_2$NH$_2$, —SO$_2$NH($C_{1-10}$ alkyl), —SO$_2$N($C_{1-10}$ alkyl)$_2$, —SO$_2$CF$_3$, —SO$_2$CF$_2$H, $C_{1-4}$acylamino $C_{0-10}$ alkyl, hydroxy, —($C_{1-10}$ alkyl)OH, —$C_{0-10}$ alkylalkoxy, cyano, ($C_{1-6}$alkyl)cyano, and $C_{1-6}$haloalkyl; wherein $R^1$ is optionally substituted with 1, 2, 3, or 4 $R^3$ substituents.

In another embodiment, $R^1$ is selected from: halogen, oxo (=O), $C_{1-10}$ alkyl(oxy)$_{0-1}$(carbonyl)$_{0-1}$$C_{0-10}$ alkyl, $C_{1-10}$ heteroalkyl(oxy)$_{0-1}$(carbonyl)$_{0-1}$$C_{0-10}$ alkyl, aryl $C_{0-10}$ alkyl (oxy)$_{0-1}$(carbonyl)$_{0-1}$$C_{0-10}$ alkyl, $C_{3-12}$ cycloalkyl $C_{0-10}$ alkyl (oxy)$_{0-1}$(carbonyl)$_{0-1}$$C_{0-10}$ alkyl, heteroaryl $C_{0-10}$ alkyl (oxy)$_{0-1}$(carbonyl)$_{0-1}$$C_{0-10}$ alkyl, ($C_{3-12}$)heterocycloalkyl $C_{0-10}$ alkyl(oxy)$_{0-1}$(carbonyl)$_{0-1}$$C_{0-10}$ alkyl, $C_{0-10}$ alkylsulfonyl$C_{0-10}$ alkyl, $C_{1-10}$ heteroalkylsulfonyl$C_{0-10}$ alkyl, ($C_{3-12}$) cycloalkyl$C_{0-10}$alkylsulfonyl$C_{0-10}$ alkyl, ($C_{3-12}$)cycloheteroalkyl$C_{0-10}$alkylsulfonyl$C_{0-10}$ alkyl, heteroaryl$C_{0-10}$ alkylsulfonyl$C_{0-10}$ alkyl, aryl$C_{0-10}$ alkylsulfonyl$C_{0-10}$ alkyl, ($C_{0-10}$ alkyl)$_{1-2}$ amino, —SO$_2$NH$_2$, —SO$_2$NH($C_{1-10}$ alkyl), —SO$_2$N($C_{1-10}$ alkyl)$_2$, —SO$_2$CF$_3$, —SO$_2$CF$_2$H, $C_{1-4}$acylamino $C_{0-10}$ alkyl, hydroxy, —($C_{1-10}$ alkyl)OH, —$C_{0-10}$ alkylalkoxy, cyano, ($C_{1-6}$alkyl)cyano, and $C_{1-6}$haloalkyl; wherein $R^1$ is optionally substituted with 1, 2, 3, or 4 $R^3$ substituents.

In yet another embodiment, $R^1$ is selected from: halogen, oxo (=O), $C_{0-10}$ alkylimino$C_{0-10}$ alkyl, $C_{1-10}$ alkyl(oxy)$_{0-1}$(carbonyl)$_{0-1}$$C_{0-10}$ alkyl, $C_{3-12}$ cycloalkyl $C_{0-10}$ alkyl (oxy)$_{0-1}$(carbonyl)$_{0-1}$$C_{0-10}$ alkyl, heteroaryl $C_{0-10}$ alkyl (oxy)$_{0-1}$(carbonyl)$_{0-1}$$C_{0-10}$ alkyl, ($C_{3-12}$)heterocycloalkyl $C_{0-10}$ alkyl(oxy)$_{0-1}$(carbonyl)$_{0-1}$$C_{0-10}$ alkyl, $C_{0-10}$ alkyl (oxy)$_{0-1}$(carbonyl)$_{0-1}$ amino$C_{0-10}$ alkyl, $C_{3-12}$ cycloalkyl $C_{0-10}$ alkyl(oxy)$_{0-1}$(carbonyl)$_{0-1}$ amino$C_{0-10}$ alkyl, ($C_{3-12}$) heterocycloalkyl $C_{0-10}$ alkyl(oxy)$_{0-1}$(carbonyl)$_{0-1}$amino-$C_{0-10}$ alkyl, $C_{0-10}$ alkylsulfonyl$C_{0-10}$ alkyl, ($C_{3-12}$)cycloheteroalkyl$C_{0-10}$alkylsulfonyl$C_{0-10}$ alkyl, $C_{1-10}$ alkylsulfamoyl$C_{0-10}$ alkyl, —SO$_2$NH$_2$, —SO$_2$NH($C_{1-10}$ alkyl), —SO$_2$N($C_{1-10}$ alkyl)$_2$, $C_{1-10}$ alkylsulfinyl$C_{0-10}$ alkyl, thio-$C_{1-10}$ alkyl, hydroxy, —($C_{1-10}$ alkyl)OH, —$C_{0-10}$ alkylalkoxy, cyano, and $C_{1-6}$haloalkyl.

In another embodiment, $R^1$ is selected from: oxo (=O), $C_{1-10}$ alkyl(oxy)$_{0-1}$(carbonyl)$_{0-1}$$C_{0-10}$ alkyl, $C_{0-10}$ alkylsulfonyl$C_{0-10}$ alkyl, ($C_{0-10}$ alkyl)$_{1-2}$ amino, —SO$_2$NH($C_{1-10}$ alkyl), —SO$_2$N($C_{1-10}$ alkyl)$_2$, and $C_{1-6}$haloalkyl; wherein $R^1$ is optionally substituted with 1, 2, 3, or 4 $R^3$ substituents.

In another embodiment, $R^1$ is selected from: methylsulfonyl, methyl, oxo, tert-butyl, —SO$_2$N(CH$_3$)$_2$, trifluoroethyl, amino, —SO$_2$NH(tert-butyl), isopropylsulfonyl, and —SO$_2$N((methyl)(tert-butyl)), wherein $R^1$ is optionally substituted with 1, 2, 3, or 4 $R^3$ substituents.

In yet another embodiment, $R^1$ is selected from: trifluoroethyl, iminomethyl, oxo, tert-butylsulfamoyl, isobutyl, cyano, methylthio, fluoro, methoxy, tert-butyloxycarbonylmethyl, chloro, methylsulfonyl, methylsulfinyl, hydroxy, tert-butylaminomethyl, isobutylaminomethyl, cyclopentylaminomethyl, dimethylpropylaminomethyl, cyclobutylaminomethyl, pyridinylmethyl, dimethylaminosulfonyl, methyl, trifluoromethyl, methylaminomethyl, piperazinylmethyl, tert-butyl, 2,2,2-trifluoroethyl, oxabicyclo[2.2.2]octyl, triazolylmethyl, tert-butylaminosulfonyl, (1,1-dimethylpropyl)sulfonyl, (1,1,2-trimethylpropyl)sulfonyl, dimethylaminomethyl, pyrrolidinylmethyl, cyclopropylaminomethyl, isopropylaminomethyl, ethylaminomethyl, azetidinylsulfonyl, morpholinylsulfonyl, pyrrolidinylsulfonyl, methoxyeth-2-yl, tert-butylsulfonyl, aminomethyl, isopropylcarbonyl, isopropylsulfonyl, isopropyl, pyrrolidinyl, piperidinyl, thiomorpholinylmethyl, piperidinylcarbonyl, azetidinylmethyl, 1-hydroxy-1-methylethyl, 1-methylethylamino, and hydroxymethyl, wherein $R^1$ is optionally substituted with 1, 2, 3, or 4 $R^3$ substituents.

In one embodiment, $R^2$ is selected from: halogen, $C_{1-10}$ alkyl(oxy)$_{0-1}$(carbonyl)$_{0-1}$$C_{0-10}$ alkyl, $C_{3-12}$ cycloalkyl, $C_{0-10}$ alkylamino$C_{0-10}$ alkyl, $C_{1-10}$ alkylsulfonyl, ($C_{0-10}$ alkyl)$_{1-2}$ amino, —CO$_2$($C_{0-10}$ alkyl), —($C_{0-10}$ alkyl)CO$_2$H, —SO$_2$CF$_3$, —SO$_2$CF$_2$H, hydroxy, —($C_{1-10}$ alkyl)OH, —$C_{0-10}$ alkylalkoxy, cyano, ($C_{1-6}$alkyl)cyano, and $C_{1-6}$haloalkyl, and wherein $R^2$ is optionally substituted with 1, 2, 3, or 4 $R^3$ substituents.

In one embodiment of the invention, $R^3$ is independently selected from: halogen, $C_{1-10}$ alkyl(oxy)$_{0-1}$(carbonyl)$_{0-1}$ $C_{0-10}$ alkyl, $C_{1-10}$ heteroalkyl(oxy)$_{0-1}$(carbonyl)$_{0-1}$$C_{0-10}$ alkyl, aryl $C_{0-10}$ alkyl(oxy)$_{0-1}$(carbonyl)$_{0-1}$$C_{0-10}$ alkyl, $C_{3-12}$ cycloalkyl $C_{0-10}$ alkyl(oxy)$_{0-1}$(carbonyl)$_{0-1}$$C_{0-10}$ alkyl, heteroaryl $C_{0-10}$ alkyl(oxy)$_{0-1}$(carbonyl)$_{0-1}$$C_{0-10}$ alkyl, ($C_{3-12}$) heterocycloalkyl $C_{0-10}$ alkyl(oxy)$_{0-1}$(carbonyl)$_{0-1}$$C_{0-10}$ alkyl, (($C_{0-10}$)alkyl)$_{1-2}$aminocarbonyloxy, —CO$_2$($C_{0-10}$ alkyl), —($C_{0-10}$ alkyl)CO$_2$H, oxo (=O), —SO$_2$NH$_2$, —SO$_2$NH($C_{1-10}$ alkyl), —SO$_2$N($C_{1-10}$ alkyl)$_2$, —SO$_2$CF$_3$, —SO$_2$CF$_2$H, amino, hydroxy, ($C_{1-10}$ alkyl)OH, $C_{1-10}$ alkoxy, ($C_{1-10}$ alkyl)cyano, cyano, and $C_{1-6}$haloalkyl, wherein $R^1$ is optionally substituted with 1, 2, 3, or 4 $R^3$ substituents.

In one embodiment of the invention $R^3$ is independently selected from: halogen, $C_{1-10}$ alkyl(oxy)$_{0-1}$(carbonyl)$_{0-1}$$C_{0-10}$alkyl, oxo (=O), amino, hydroxy, ($C_{1-10}$ alkyl)OH, $C_{1-10}$alkoxy, and $C_{1-6}$haloalkyl; wherein $R^3$ is optionally substituted with 1, 2, or 3 $R^4$ substituents.

In one embodiment, $R^3$ is independently selected from: halogen, $C_{1-10}$ alkyl(oxy)$_{0-1}$(carbonyl)$_{0-1}$$C_{0-10}$ alkyl, amino, and $C_{1-6}$haloalkyl, wherein $R^3$ is optionally substituted with 1, 2, 3, or 4 $R^4$ substituents.

In another embodiment of the invention $R^3$ is independently selected from: methyl, trifluoromethyl, tert-butyl, and amino; wherein $R^3$ is optionally substituted with 1, 2, or 3 $R^4$ substituents.

In yet another embodiment of the invention $R^3$ is independently selected from: methyl, ethyl, fluoro, tert-butyl, oxo, trifluoromethyl, tert-butyloxycarbonyl, isopropyl, hydroxy, amino, methoxy, and tert-butyloxycarbonylmethyl, wherein $R^3$ is optionally substituted with 1, 2, or 3 $R^4$ substituents.

In one embodiment of the invention, $R^4$ is independently selected from hydroxy, ($C_{1-6}$)alkyl, ($C_{1-6}$)alkoxy, ($C_{1-10}$ alkyl)OH, halogen, —O(C=O)$C_1$-$C_6$ alkyl, trifluoromethoxy, trifluoroethoxy, trifluoromethyl, trifluoroethyl, oxo (O=), —O$_{(0-1)}$($C_{1-10}$)haloalkyl, amino($C_{1-6}$alkyl)$_{0-2}$ and NH$_2$.

In another embodiment of the invention, $R^4$ is independently selected from hydroxy, methyl, oxo, trifluoromethyl, methoxy, 1-hydroxy-1-methylethyl, amino, methoxyethyl, difluoromethyl, dimethylamino, ethyl, and NH$_2$.

In a particular variant of the invention, in the compound of Formula I, the substituents are: A is selected from phenyl, dihydrobenzisothiazolyl, and 2,3-dihydrobenzo[d]isothiazolyl; m and n are both 0; p is 4; X is CH$_2$ or O wherein only one X is O; $R^3$ is independently selected from: methyl, trifluoromethyl, tert-butyl, and amino; wherein $R^3$ is optionally substituted with 1, 2, or 3 $R^4$ substituents; and $R^4$ is independently selected from hydroxy, methyl, oxo, trifluoromethyl, methoxy, 1-hydroxy-1-methylethyl, amino, methoxyethyl, difluoromethyl, dimethylamino, ethyl, and NH₂.

In another particular variant of the invention, in the compound of Formula I, the substituents are: A is selected from phenyl, pyridinyl, 2,3-dihydro-1H-indolyl, 1,3-benzothiazolyl, 2,3-dihydroisoindolyl, dihydrobenzisothiazolyl, and 2,3-dihydrobenzo[d]isothiazolyl and

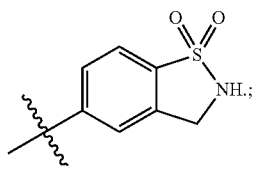 [SMILES: *c1ccc2c(c1)CNS2(=O)=O]

X is CH₂ or O wherein only one X is O; p is 4 or 5; n is 0; m is 0, 1, 2, 3, or 4; R³ is independently selected from: methyl, ethyl, fluoro, tert-butyl, oxo, trifluoromethyl, tert-butyloxycarbonyl, isopropyl, hydroxy, amino, methoxy, and tert-butyloxycarbonylmethyl; R¹ is selected from: trifluoroethyl, iminomethyl, oxo, tert-butylsulfamoyl, isobutyl, cyano, methylthio, fluoro, methoxy, tert-butyloxycarbonylmethyl, chloro, methylsulfonyl, methylsulfinyl, hydroxy, tert-butylaminomethyl, isobutylaminomethyl, cyclopentylaminomethyl, dimethylpropylaminomethyl, cyclobutylaminomethyl, pyridinylmethyl, dimethylaminosulfonyl, methyl, trifluoromethyl, methylaminomethyl, piperazinylmethyl, tert-butyl, 2,2,2-trifluoroethyl, oxabicyclo[2.2.2]octyl, triazolylmethyl, tert-butylaminosulfonyl, (1,1-dimethylpropyl)sulfonyl, (1,1,2-trimethylpropyl)sulfonyl, dimethylaminomethyl, pyrrolidinylmethyl, cyclopropylaminomethyl, isopropylaminomethyl, ethylaminomethyl, azetidinylsulfonyl, morpholinylsulfonyl, pyrrolidinylsulfonyl, methoxyeth-2-yl, tert-butylsulfonyl, aminomethyl, isopropylcarbonyl, isopropylsulfonyl, isopropyl, pyrrolidinyl, piperidinyl, thiomorpholinylmethyl, piperidinylcarbonyl, azetidinylmethyl, 1-hydroxy-1-methylethyl, 1-methylethylamino, and hydroxymethyl, wherein R¹ is optionally substituted with 1, 2, 3, or 4 R³ substituents.

Optical Isomers-Diastereomers-Geometric Isomers Tautomers

Compounds of Formula I contain one or more asymmetric centers and can thus occur as racemates and racemic mixtures, single enantiomers, diastereomeric mixtures and individual diastereomers. The present invention is meant to comprehend all such isomeric forms of the compounds of Formula I, either as single species or mixtures thereof.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form known as keto-enol tautomers. The individual tautomers as well as mixture thereof are encompassed with compounds of Formula I.

Specific embodiments of the present invention include a compound which is selected from the group consisting of the subject compounds of the Examples herein or a pharmaceutically acceptable salt thereof.

The compounds of the present invention may contain one or more asymmetric centers and can thus occur as "stereoisomers" including racemates and racemic mixtures, enantiomeric mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the scope of this invention. The present invention is meant to comprehend all such isomeric forms of these compounds. When bonds to the chiral carbon are depicted as straight lines in the formulas of the invention, it is understood that both the (R) and (S) configurations of the chiral carbon, and hence both enantiomers and mixtures thereof, are embraced within the Formula. For example, Formula I shows the structure of the class of compounds without specific stereochemistry. When the compounds of the present invention contain one chiral center, the term "stereoisomer" includes both enantiomers and mixtures of enantiomers, such as the specific 50:50 mixture referred to as racemic mixtures.

The compounds of Formula (I) may contain asymmetric or chiral centers, and, therefore, exist in different stereoisomeric forms. It is intended that all stereoisomeric forms of the compounds of Formula (I) as well as mixtures thereof, including racemic mixtures, form part of the present invention. In addition, the present invention embraces all geometric and positional isomers. For example, if a compound of Formula (I) incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) may be atropisomers (e.g., substituted biaryls) and are considered as part of this invention. Enantiomers can also be separated by use of chiral HPLC column.

It is also possible that the compounds of Formula (I) may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of Formula (I) incorporates a double bond or a fused ring, both the cis- and trans-forms, as well as mixtures, are embraced within the scope of the invention. Also, for example, all keto-enol and imine-enamine forms of the compounds are included in the invention.) Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

In the present application when a particular stereomeric compound is named using an "and" in the stereomeric designation, the "and" indicates a racemic mixture of the enantiomers. That is, the individual enantiomers were not individually isolated.

When the stereomeric nomenclature includes "or", for example, the "or" indicates that chiral resolution of racemate into individual enantiomers was accomplished but the actual optical activity of the specific enantiomer was not necessarily determined.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art. Alternatively, any enantiomer of a compound can be obtained by stereoselective synthesis using optically pure starting materials or reagents of known configuration by methods well known in the art.

Salts

The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, 1-hydroxy-2-naphthoic acid (xinafoate) and the like. Particularly preferred are citric, hydrobromic, hydrochloric, maleic, phosphoric, sulfuric, and tartaric acids.

It will be understood that, unless otherwise specified, references to the compound of Formula I subsets thereof, embodiments thereof, as well as specific compounds are meant to also include the pharmaceutically acceptable salts and stereoisomers thereof.

Furthermore, some of the crystalline forms for compounds of the present invention may exist as polymorphs and as such all forms are intended to be included in the present invention. In addition, some of the compounds of the instant invention may form solvates with water (hydrates) or common organic solvents. Such solvates are encompassed within the scope of this invention.

Labelled Compounds

In the compounds of generic Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the schemes and examples herein using appropriate isotopically-enriched reagents and/or intermediates.

Utilities

Compound of Formula I or its pharmaceutically acceptable salts and pharmaceutical compositions can be used to treat or prevent a variety of conditions or diseases mediated by Janus kinases, in particular diseases or conditions that can be ameliorated by the inhibition of a Janus kinase such as JAK1, JAK2, JAK3 or TYK2. Such conditions and diseases include, but are not limited to: (1) arthritis, including rheumatoid arthritis, juvenile arthritis, and psoriatic arthritis; (2) asthma and other obstructive airways diseases, including chronic asthma, late asthma, airway hyper-responsiveness, bronchitis, bronchial asthma, allergic asthma, intrinsic asthma, extrinsic asthma, dust asthma, recurrent airway obstruction, and chronic obstruction pulmonary disease including emphysema; (3) autoimmune diseases or disorders, including those designated as single organ or single cell-type autoimmune disorders, for example Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia, sympathetic ophthalmia, myasthenia gravis, Graves' disease, primary biliary cirrhosis, chronic aggressive hepatitis, ulcerative colitis and membranous glomerulopathy, those designated as involving systemic autoimmune disorder, for example systemic lupus erythematosis, rheumatoid arthritis, Sjogren's syndrome, Reiter's syndrome, polymyositis-dermatomyositis, systemic sclerosis, polyarteritis nodosa, multiple sclerosis and bullous pemphigoid, and additional autoimmune diseases, which can be B-cell (humoral) based or T-cell based, including Cogan's syndrome, ankylosing spondylitis, Wegener's granulomatosis, autoimmune alopecia, Type I or juvenile onset diabetes, and thyroiditis; (4) cancers or tumors, including alimentary/gastrointestinal tract cancer, colon cancer, liver cancer, skin cancer including mast cell tumor and squamous cell carcinoma, breast and mammary cancer, ovarian cancer, prostate cancer, lymphoma, leukemia, including acute myelogenous leukemia and chronic myelogenous leukemia, kidney cancer, lung cancer, muscle cancer, bone cancer, bladder cancer, brain cancer, melanoma including oral and metastatic melanoma, Kaposi's sarcoma, myelomas including multiple myeloma, myeloproliferative disorders, proliferative diabetic retinopathy, and angiogenic-associated disorders including solid tumors; (5) diabetes, including Type I diabetes and complications from diabetes; (6) eye diseases, disorders or conditions including autoimmune diseases of the eye, keratoconjunctivitis, vernal conjunctivitis, uveitis including uveitis associated with Behcet's disease and lens-induced uveitis, keratitis, herpetic keratitis, conical keratitis, corneal epithelial dystrophy, keratoleukoma, ocular premphigus, Mooren's ulcer, scleritis, Grave's ophthalmopathy, Vogt-Koyamagi-Harada syndrome, keratoconjunctivitis sicca (dry eye), phlyctenule, iridocyclitis, sarcoidosis, endocrine ophthalmopathy, sympathetic ophthalmitis, allergic conjunctivitis, and ocular neovascularization; (7) intestinal inflammations, allergies or conditions including Crohn's disease and/or ulcerative colitis, inflammatory bowel disease, coeliac diseases, proctitis, eosinophilic gastroenteritis, and mastocytosis; (8) neurodegenerative diseases including motor neuron disease, Alzheimer's disease, Parkinson's disease, amyotrophic lateral sclerosis, Huntington's disease, cerebral ischemia, or neurodegenerative disease caused by traumatic injury, strike, glutamate neurotoxicity or hypoxia; ischemic/reperfusion injury in stroke, myocardial ischemica, renal ischemia, heart attacks, cardiac hypertrophy, atherosclerosis and arteriosclerosis, organ hypoxia, and platelet aggregation; (9) skin diseases, conditions or disorders including atopic dermatitis, eczema, psoriasis, scleroderma, pruritus and other pruritic conditions; (10) allergic reactions including anaphylaxis, allergic rhinitis, allergic dermatitis, allergic urticaria, angioedema, allergic asthma, or allergic reaction to insect bites, food, drugs, or pollen; and (11) transplant rejection, including pancreas islet transplant rejection, bone marrow transplant rejection, graft-versus-host disease, organ and cell transplant rejection such as bone marrow, cartilage, cornea, heart, intervertebral disc, islet, kidney, limb, liver, lung, muscle, myoblast, nerve, pancreas, skin, small intestine, or trachea, and xeno transplantation.

Accordingly, another aspect of the present invention provides a method for the treatment or prevention of a JAK-mediated disease or disorder comprising administering to a mammal in need thereof a therapeutically effective amount of a compound of Formula I. In one embodiment such diseases include asthma and rheumatoid arthritis. In another embodiment, such diseases include recurrent airway obstruction, and chronic obstruction pulmonary disease (COPD), or obstructive airways diseases. In a variant of this embodiment the disease is COPD.

Another aspect of the present invention provides for the use of a compound of Formula I in the manufacture of a medicament for the treatment or prevention of a JAK-mediated diseases or disorder.

One aspect of the invention is the use of a compound of Formula I or a pharmaceutically acceptable salt or a stereoisomer thereof in the manufacture of a medicament for the treatment of a disease or a disorder ameliorated by the inhibition of Janus kinases JAK1 and JAK2.

Another aspect of the invention is the use of a compound of Formula I or a pharmaceutically acceptable salt or a stereoisomer thereof and a second active agent in the manufacture of a medicament for the treatment of a disease or a disorder ameliorated by the inhibition of Janus kinases JAK1 and JAK2.

Dose Ranges

The magnitude of prophylactic or therapeutic dose of a compound of Formula I will, of course, vary with the nature and the severity of the condition to be treated and with the particular compound of Formula I and its route of administration. It will also vary according to a variety of factors including the age, weight, general health, sex, diet, time of administration, rate of excretion, drug combination and response of the individual patient. In general, the daily dose from about 0.001 mg to about 100 mg per kg body weight of a mammal, preferably 0.01 mg to about 10 mg per kg. On the other hand, it may be necessary to use dosages outside these limits in some cases.

The amount of active ingredient that may be combined with the carrier materials to produce a single dosage form will vary depending upon the host treated and the particular mode of administration. For example, a formulation intended for the oral administration of humans may contain from 0.05 mg to 5 g, of active agent compounded with an appropriate and convenient amount of carrier material which may vary from about 5 to about 99.95 percent of the total composition. In some cases, the dosage unit forms may contain from about 0.05 to about 3 g of active ingredient. Dosage unit forms will generally contain between from about 0.1 mg to about 0.4 g of an active ingredient, typically 0.1 mg, 0.2 mg, 0.3 mg, 0.4 mg, 0.5 mg, 1 mg, 2 mg, 5 mg, 10 mg, 25 mg, 50 mg, 100 mg, 200 mg, or 400 mg.

Pharmaceutical Compositions

Another aspect of the present invention provides pharmaceutical compositions comprising a compound of Formula I with a pharmaceutically acceptable carrier. For the treatment of any of the prostanoid mediated diseases compounds of Formula I may be administered orally, by inhalation spray, topically, parenterally or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle, sheep, dogs, cats, etc., the compound of the invention is effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and U.S. Pat. No. 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water-miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropyl methylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of an oil-in-water emulsion. The oily phase may be a vegetable oil, for example olive oil or *arachis* oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. Cosolvents such as ethanol, propylene glycol or polyethylene glycols may also be used. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Dosage forms for inhaled administration may conveniently be formulated as aerosols or dry powders. For compositions suitable and/or adapted for inhaled administration, it is preferred that the active substance is in a particle-size-reduced form, and more preferably the size-reduced form is obtained or obtainable by micronization.

In one embodiment the medicinal preparation is adapted for use with a pressurized metered dose inhaler (pMDI) which releases a metered dose of medicine upon each actuation. The formulation for pMDIs can be in the form of solutions or suspensions in halogenated hydrocarbon propellants. The type of propellant being used in pMDIs is being shifted to hydrofluoroalkanes (HFAs), also known as hydrofluorocarbons (HFCs). In particular, 1,1,1,2-tetrafluoroethane (HFA 134a) and 1,1,1,2,3,3,3-heptafluoropropane (HFA 227) are used in several currently marketed pharmaceutical inhalation products. The composition may include other pharmaceutically acceptable excipients for inhalation use such as ethanol, oleic acid, polyvinylpyrrolidone and the like.

Pressurized MDIs typically have two components. Firstly, there is a canister component in which the drug particles are stored under pressure in a suspension or solution form. Secondly, there is a receptacle component used to hold and actuate the canister. Typically, a canister will contain multiple doses of the formulation, although it is possible to have single dose canisters as well. The canister component typically includes a valve outlet from which the contents of the canister can be discharged. Aerosol medication is dispensed from the pMDI by applying a force on the canister component to push it into the receptacle component thereby opening the valve outlet and causing the medication particles to be conveyed from the valve outlet through the receptacle component and discharged from an outlet of the receptacle. Upon discharge from the canister, the medication particles are "atomized", forming an aerosol. It is intended that the patient coordinate the discharge of aerosolized medication with his or her inhalation, so that the medication particles are entrained in the patient's aspiratory flow and conveyed to the lungs. Typically, pMDIs use propellants to pressurize the contents of the canister and to propel the medication particles out of the outlet of the receptacle component. In pMDIs, the formulation is provided in a liquid or suspension form, and resides within the container along with the propellant. The propellant can take a variety of forms. For example, the propellant can comprise a compressed gas or liquefied gas.

In another embodiment the medicinal preparation is adapted for use with a dry powder inhaler (DPI). The inhalation composition suitable for use in DPIs typically comprises particles of the active ingredient and particles of a pharmaceutically acceptable carrier. The particle size of the active material may vary from about 0.1 µm to about 10 µm; however, for effective delivery to the distal lung, at least 95 percent of the active agent particles are 5 µm or smaller. Each of the active agent can be present in a concentration of 0.01-99%. Typically however, each of the active agents is present in a concentration of about 0.05 to 50%, more typically about 0.2-20% of the total weight of the composition.

As noted above, in addition to the active ingredients, the inhalable powder preferably includes pharmaceutically acceptable carrier, which may be composed of any pharmacologically inert material or combination of materials which is acceptable for inhalation. Advantageously, the carrier particles are composed of one or more crystalline sugars; the carrier particles may be composed of one or more sugar alcohols or polyols. Preferably, the carrier particles are particles of dextrose or lactose, especially lactose. In embodiments of the present invention which utilize conventional dry powder inhalers, such as the Handihaler, Rotohaler, Diskhaler, Twisthaler and Turbohaler, the particle size of the carrier particles may range from about 10 microns to about 1000 microns. In certain of these embodiments, the particle size of the carrier particles may range from about 20 microns to about 120 microns. In certain other embodiments, the size of at least 90% by weight of the carrier particles is less than 1000 microns and preferably lies between 60 microns and 1000 microns. The relatively large size of these carrier particles gives good flow and entrainment characteristics. Where present, the amount of carrier particles will generally be up to 95%, for example, up to 90%, advantageously up to 80% and preferably up to 50% by weight based on the total weight of the powder. The amount of any fine excipient material, if present, may be up to 50% and advantageously up to 30%, especially up to 20%, by weight, based on the total weight of the powder. The powder may optionally contain a performance modifier such as L-leucine or another amino acid, and/or metals salts of stearic acid such as magnesium or calcium stearate.

Compounds of Formula I may also be administered in the form of suppositories for rectal administration of the drug. These compositions can be prepared by mixing the drug with a suitable non-irritating excipient which is solid at ambient temperatures but liquid at the rectal temperature and will therefore melt in the rectum to release the drug. Such materials are cocoa butter and polyethylene glycols.

For topical use, creams, ointments, gels, solutions or suspensions, etc., containing the compound of Formula I are employed. (For purposes of this application, topical application shall include mouth washes and gargles.) Topical formulations may generally be comprised of a pharmaceutical carrier, cosolvent, emulsifier, penetration enhancer, preservative system, and emollient.

Combinations with Other Drugs

For the treatment and prevention of JAK mediated diseases, compound of Formula I may be co-administered with other therapeutic agents. Thus in another aspect the present invention provides pharmaceutical compositions for treating JAK mediated diseases comprising a therapeutically effective amount of a compound of Formula I and one or more other therapeutic agents. In particular, for the treatment of the inflammatory diseases rheumatoid arthritis, psoriasis, inflammatory bowel disease, COPD, asthma and allergic rhinitis a compound of Formula I may be combined with agents such as: (1) TNF-α inhibitors such as Remicade® and Enbrel®); (2) non-selective COX-I/COX-2 inhibitors (such as piroxicam, diclofenac, propionic acids such as naproxen, flubiprofen, fenoprofen, ketoprofen and ibuprofen, fenamates such as mefenamic acid, indomethacin, sulindac, apazone, pyrazolones such as phenylbutazone, salicylates such as aspirin); (3) COX-2 inhibitors (such as meloxicam, celecoxib, rofecoxib, valdecoxib and etoricoxib); (4) other agents for treatment of rheumatoid arthritis including low dose methotrexate, lefunomide, ciclesonide, hydroxychloroquine, d-penicillamine, auranofin or parenteral or oral gold; (5) leukotriene biosynthesis inhibitor, 5-lipoxygenase (5-LO) inhibitor or 5-lipoxygenase activating protein (FLAP) antagonist such as zileuton; (6) LTD4 receptor antagonist such as zafirlukast, montelukast and pranlukast; (7) PDE4 inhibitor such as roflumilast; (8) antihistaminic H1 receptor antagonists such as cetirizine, loratadine, desloratadine, fexofenadine, astemizole, azelastine, and chlorpheniramine; (9) α1- and α2-adrenoceptor agonist vasoconstrictor sympathomimetic agent, such as propylhexedrine, phenylephrine, phenylpropanolamine, pseudoephedrine, naphazoline hydrochloride, oxymetazoline hydrochloride, tetrahydrozoline hydrochloride, xylometazoline hydrochloride, and ethylnorepinephrine hydrochloride; (10) anticholinergic agents such as ipratropium bromide, tiotropium bromide, oxitropium bromide, aclindinium bromide, glycopyrrolate, pirenzepine, and telenzepine; (11) β-adrenoceptor agonists such as metaproterenol, isoproterenol, isoprenaline, albuterol, salbutamol, formoterol, salmeterol, terbutaline, orciprenaline, bitolterol mesylate, and pirbuterol, or methylxanthanines including theophylline and aminophylline, sodium cromoglycate; (12) insulin-like growth factor type I (IGF-1) mimetic; (13) inhaled glucocorticoid with reduced systemic side effects, such as prednisone, prednisolone, flunisolide, triamcinolone acetonide, beclomethasone dipropionate, budesonide, fluticasone propionate, ciclesonide and mometasone furoate.

Methods of Synthesis

Schemes and Examples

The abbreviations used herein have the following tabulated meanings Abbreviations not tabulated below have their meanings as commonly used unless specifically stated otherwise.

| | |
|---|---|
| ACN, MeCN | acetonitrile |
| BAST | bis(2-methoxyethyl)aminosulfur trifluoride |
| t-Bu XPhos | 2-di tert-butylphosphino-2',4',6'-triisopropylbiphenyl |
| Chiral SFC | chiral super critical fluid chromatography |
| $CO_2$ | carbon dioxide |

| | |
|---|---|
| Cs₂CO₃ | cesium carbonate |
| Dba | dibenzylideneacetone |
| DBU | 1,8-diazabicyclo[5.4.0]undec-7-ene |
| DCE | 1,2-dichloroethane |
| DCM | dichloromethane |
| DEA | diethylamine |
| DIPEA | N,N-diisopropylethylamine |
| DMEA | dimethylethylamine |
| DMF | N,N-dimethylformamide |
| DMSO | dimethyl sulfoxide |
| DSC | N,N-disuccinimidyl carbonate |
| EDC | 3-(ethyliminomethyleneamino)-N,N-dimethyl-propan-1-amine |
| EtOAc | ethyl acetate |
| GCMS | gas chromatography/mass spectrometry |
| HATU | O-(7-aza-1H-benzotriazol-1-yl)-N,N,N',N'-tetramethyluronium hexafluorophosphate |
| HCl | hydrogen chloride |
| HOBt | 1-hydroxybenzotriazole |
| HPLC | high pressure liquid chromatography |
| IPA | 2-propanol |
| LDA | lithium diisopropylamide |
| m-CPBA | meta-chloroperoxybenzoic acid |
| LR | low resolution |
| LRMS | low resolution mass spectrometry |
| MeI | iodomethane |
| Me-THF | 2-methyltetrahydrofuran |
| Me₄-t-Bu-X-Phos | di-tert-butyl[3,4,5,6-tetramethyl-2',4',6'-tri(propan-2-yl)biphenyl-2-yl]phosphane |
| MgSO₄ | magnesium sulfate |
| MP-(OAc)₃BH | solid supported (macro porous) triacetoxyborohydride |
| MPLC | medium pressure liquid chromatography |
| NaH | sodium hydride |
| Na₂SO₄ | sodium sulfate |
| NaBH₄ | sodium borohydride |
| NaHCO₃ | sodium bicarbonate |
| NaOMe | sodium methoxide |
| NMO | 4-methylmorpholine N-oxide |
| Pd₂(dba)₃ | tris(dibenzylideneacetone)dipalladium(0) |
| POCl₃ | phosphorus (V) oxychloride |
| PyBOP | (7-azabenzotriazol-1-yloxy)tripyrrolidinophosphonium hexafluorophosphate |
| SEM-Cl | 2-(trimethylsilyl)ethoxymethyl chloride |
| SFC | Supercritical fluid chromatography |
| SiliaCat® DPP-Pd | silica bound diphenylphosphine palladium (II) |
| TBAF | tetra-n-butylammonium fluoride |
| TBS-Cl | tert-butyldimethylsilyl chloride |
| t-BuOH | tert-butanol |
| t-Bu Xphos | 2-di-tert-butylphosphino-2',4',6'-triisopropylbiphenyl |
| TEA | triethylamine |
| TFA | trifluoroacetic acid |
| THF | tetrahydrofuran |
| TPAP | tetra-n-propylammonium perruthenate (VII) |
| X-Phos | 2-dicyclohexylphosphino-2',4',6'-triisopropyl-biphenyl |
| HCOOH | formic acid |
| Kt-OBu | potassium tert-butoxide |
| Na₂S₂O₅ | sodium metabisulfite |
| NMR | nuclear magnetic resonance |
| TLC | thin layer chromatography |
| (EtO)₂P(O)CH₂CN | diethyl (cyanomethyl)phosphonate |
| MsCl | methanesulfonyl chloride |
| TsOH | p-toluenesulfonic acid |
| KCN | potassium cyanide |
| Si-DMT | silica supported dimercaptotriazine |
| TMS | trimethylsilane |
| CF₃TMS | (trifluoromethyl)trimethylsilane |

Alkyl Group Abbreviations

| | |
|---|---|
| Me | methyl |
| Et | ethyl |
| n-Pr | normal propyl |
| i-Pr | isopropyl |
| n-Bu | normal butyl |
| i-Bu | isobutyl |
| s-Bu | secondary butyl |
| t-Bu | tertiary butyl |
| c-Pr | cyclopropyl |
| c-Bu | cyclobutyl |
| c-Pen | cyclopentyl |
| c-Hex | cyclohexyl |

Methods of Synthesis

The compounds of the present invention can be prepared according to the following general schemes using appropriate materials, and are further exemplified by the subsequent specific examples. The compounds illustrated in the examples are not to be construed as forming the only genus that is considered as the invention. The illustrative Examples below, therefore, are not limited by the compounds listed or by any particular substituents employed for illustrative purposes. Substituent numbering as shown in the schemes does not necessarily correlate to that used in the claims and often, for clarity, a single substituent is shown attached to the compound where multiple substituents are allowed under the definitions of the instant invention herein above.

Those skilled in the art will readily understand that known variations of the conditions and processes of the following preparative procedures can be used to prepare these compounds. The invention will now be illustrated in the following non-limiting Examples in which, unless otherwise stated:

All starting materials used to prepare the intermediates and final compounds described herein were obtained from commercial vendors, and were used as is upon receipt.

All reactions were stirred (mechanically, stir bar/stir plate, or shaken) and conducted under an inert atmosphere of nitrogen or argon unless specifically stated otherwise.

All starting materials used to prepare the intermediates and final compounds described herein were obtained from commercial vendors, and were used as is upon receipt.

All temperatures are degrees Celsius (° C.) unless otherwise noted.

Ambient temperature is 15-25° C.

Most compounds were purified by reverse-phase preparative HPLC, MPLC on silica gel, SFC, recrystallization and/or swish (suspension in a solvent followed by filtration of the solid).

The course of the reactions was followed by thin layer chromatography (TLC) and/or LCMS and/or NMR and reaction times are given for illustration only.

All end products were analyzed by NMR and LCMS.

Intermediates were analyzed by NMR and/or TLC and/or LCMS.

Method 1

General procedures to prepare intermediates of the instant invention are described in Scheme 1. Using an appropriate base, such as DBU, in a suitable solvent, such as MeCN, EtOH, n-BuOH or tert-BuOH, at a temperature between 25-110° C., protected pyrazolopyridone I can undergo conjugate addition to optionally substituted acrylonitriles to yield alkylated protected pyrazolopyridones II, an intermediate in the synthesis of examples of the instant invention. Deprotection of II to the free alkylated pyridone III can then be effected either using a suitable acid, such as TFA, or under hydrogenolysis conditions using Pd on carbon at approximately 1 atmosphere of hydrogen, in a suitable solvent such as EtOAc, EtOH, MeOH, or using combinations of solvents thereof

SCHEME 1

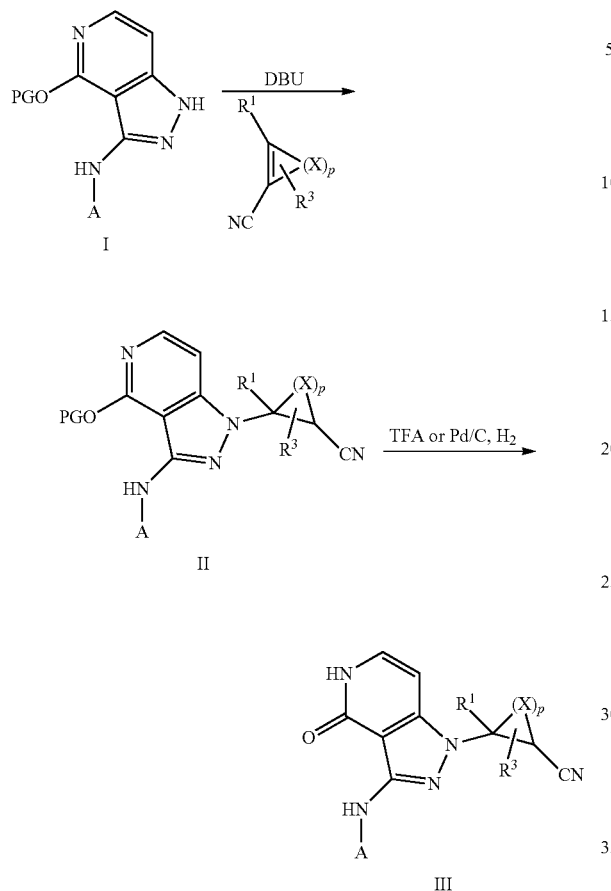

SCHEME 2

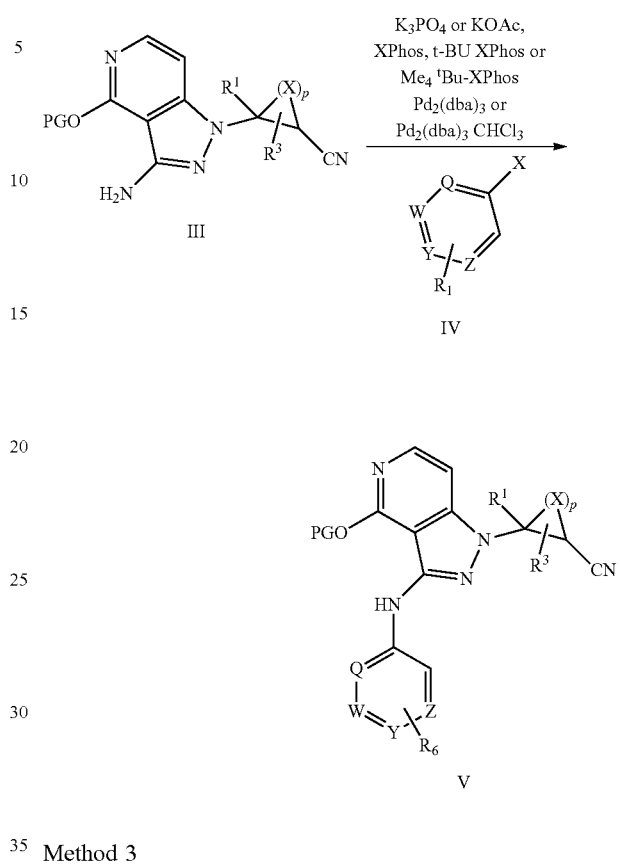

Method 2

General procedures to prepare examples of the instant invention are described in Scheme 2. Alkylated 3-amino pyrazolopyrimidines III (A=H) are cross coupled to aryl and heteroaryl halides IV using an appropriate catalytic palladium-ligand system, such as $Pd_2(dba)_3$ or $Pd_2(dba)_3 \cdot CHCl_3$, and 2-di-tert-butylphosphino-2',4',6'-triisopropylbiphenyl (t-Bu XPhos) or di-tert-butyl[3,4,5,6-tetramethyl-2',4',6'-tri(propan-2-yl)biphenyl-2-yl]phosphane ($Me_4$ t-Bu-XPhos), or 2-dicyclohexylphosphino-2',4',6'-triisopropylbiphenyl (XPhos). Alternatively, a suitable precatalyst complex such as [t-Bu XPhos Pd G3] (Aldrich catalogue #762229) could also be employed in place of the independent palladium source and ligand. Typical conditions employ 1-2 equivalents of the aryl/heteroaryl halide relative to the pyrazolopyrimidine with 10-25% Pd precatalyst loading. Typically, the cross coupling is carried out using either 2-propanol, t-BuOH or t-amyl alcohol solvents, using KOAc or $K_3PO_4$ as base. Reactions were typically carried out between 65-90° C., to yield intermediates V of the instant invention.

Method 3

General procedures to prepare examples of the instant invention are described in Scheme 3. Protected pyrazolopyrimidines V are deprotected in the presence of acid, such as TFA or HCl, to afford the deprotected pyrazolopyridones VI. Alternatively, in the case of hydrolytically unstable pyridone protecting groups (e.g. PG=Bn), deprotection could be achieved under hydrogenolysis conditions using Pd on carbon in the presence of hydrogen in a suitable solvent such as EtOAc, EtOH, MeOH, or combinations of solvents thereof.

SCHEME 3

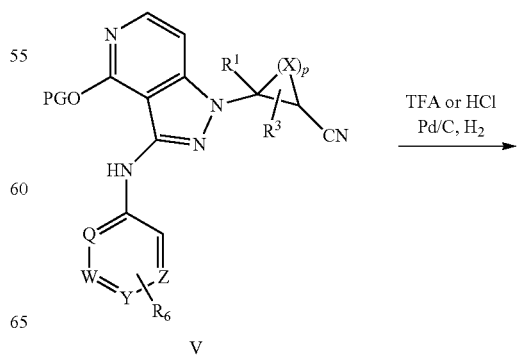

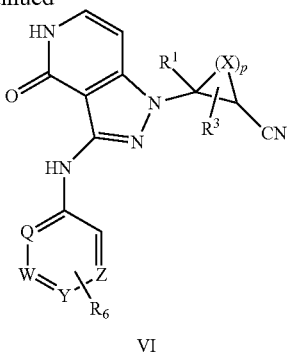

INTERMEDIATES

The following experimental procedures detail the preparation of chemical materials used in the synthesis of Examples of the instant invention. The exemplified procedures are for illustrative purposes only, and are not intended to limit the scope of the instant invention in any way.

Intermediate 1

4-(benzyloxy)-1H-pyrazolo[4,3-c]pyridin-3-amine

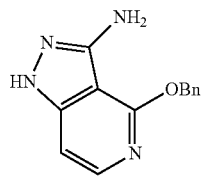

Step 1: 2-(benzyloxy)-4-methoxynicotinonitrile

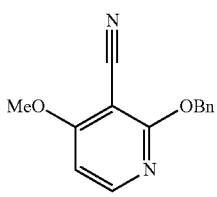

To a solution of 2-hydroxy-4-methoxynicotinonitrile (60 g, 0.40 mol) in toluene (0.60 L) was added Ag$_2$CO$_3$ (0.14 kg, 0.51 mol) and BnBr (87 g, 0.51 mol) at room temperature. The mixture was stirred at 50° C. for 3 hours. The mixture was filtered and the cake washed with DCM. The filtrate was concentrated in vacuo and petroleum ether (100 mL) was added to the residue and the solid was filtered to give compound I-1a as a solid. LRMS (ESI) calc'd for C$_{14}$H$_{13}$N$_2$O$_2$ [M+H]$^+$: 241, found 241. $^1$H NMR (600 MHz CDCl$_3$): δ 8.21 (d, J=6.6 Hz, 1H), 7.48 (d, J=7.8 Hz, 2H), 7.38 (m, 2H), 7.32 (m, 1H), 6.58 (d, J=6.0 Hz, 1H), 5.51 (s, 2H), 3.99 (s, 3H).

Step 2: 4-(benzyloxy)-1H-pyrazolo[4,3-c]pyridin-3-amine

A suspension of 2-(benzyloxy)-4-methoxynicotinonitrile (100 g, 410 mmol) in hydrazine hydrate (0.20 kg, 4.1 mol) and n-BuOH (600 mL) was heated to reflux overnight. The mixture was concentrated in vacuo and purified by silica chromatography, eluting with 25% ethyl acetate in hexanes. Concentration of the desired fraction in vacuo afforded compound I-1 as a solid. $^1$H NMR (400 MHz CDCl$_3$): δ 9.97 (s, 1H), 7.75 (d, J=6.4 Hz, 1H), 7.40 (d, J=7.2 Hz, 2H), 7.24-7.33 (m, 3H), 6.69 (d, J=6.4 Hz, 1H), 5.46 (s, 2H), 4.50 (s, 2H).

Intermediate 2

3,6-dihydro-2H-pyran-4-carbonitrile

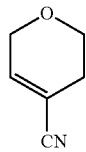

To a solution of trimethylsilanecarbonitrile (713 g, 7.19 mol) in dichloromethane (2.50 L) under nitrogen, was added oxan-4-one (600 g, 5.99 mol), followed by dropwise addition of trimethylsilyl trifluoromethanesulfonate (40.0 g, 180 mmol) at 0° C. To this was added pyridine (5 L), followed by dropwise addition of phosphoryl chloride (2.74 kg, 17.8 mol) and the resulting solution was stirred overnight at 70° C., then quenched by pouring into 20 L of water/ice. The pH was adjusted to 7 with aqueous HCl (2 M) and the solid was filtered out. The filtrate was extracted with dichloromethane (×3) and the combined organic layers were washed with brine (×2), dried over anhydrous sodium sulfate, filtered and concentrated in vacuo. The crude product was purified by distillation under reduced pressure (10 mm Hg) and the fraction was collected at 35° C. as a liquid. $^1$H NMR (600 MHz, CDCl$_3$): δ 6.64 (m, 1H), 4.25 (q, J=2.9 Hz, 2H), 3.81 (t, J=5.8 Hz, 2H), 2.35 (m, 2H).

Intermediates I-3A and I-3B (3S,4R) and (3R,4S)-3-(3-amino-4-(benzyloxy)-1H-pyrazolo[4,3-c]pyridin-1-yl)tetrahydro-2H-pyran-4-carbonitrile

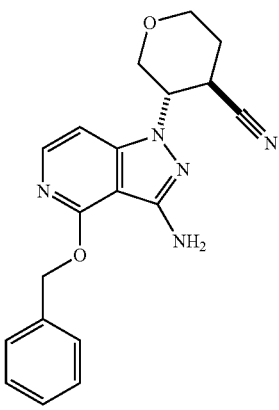

I-3B

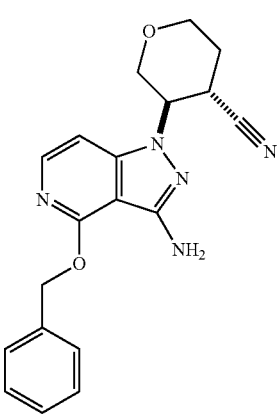

To a solution of 4-(benzyloxy)-1H-pyrazolo[4,3-c]pyridin-3-amine I-1 (300 g, 1.25 mol) in ACN (6.00 L) under nitrogen, was added 3,6-dihydro-2H-pyran-4-carbonitrile (398 g, 3.65 mol), and DBU (469 g, 3.08 mol). The resulting solution was stirred overnight at 80° C., then cooled and concentrated in vacuo. The residue was purified by silica chromatography, eluting with 50% ethyl acetate in hexanes to afford a solid. SFC separation was performed using a Phenomenex Lux-4 column with 25% methanol modifier in $CO_2$. Retention times were 3.8 minutes (Intermediate 3A) and 5.0 minutes (Intermediate 3B). LRMS (ESI) calc'd for $C_{19}H_{20}N_5O_2[M+H]^+$: 350, found 350. $^1$H NMR (600 MHz, CDCl$_3$): δ 7.89 (d, J=6.4 Hz, 1H), 7.48 (d, J=7.1 Hz, 2H), 7.41 (t, J=7.1 Hz, 2H), 7.34 (m, 1H), 6.82 (d, J=6.4 Hz, 1H), 5.53 (s, 2H), 4.97 (br s, 2H), 4.40 (dt, J=10.6, 4.7 Hz, 1H), 4.04 (dd, J=11.7, 4.0 Hz, 1H), 4.00 (dd, J=11.7, 4.5 Hz, 1H), 3.74 (t, J=11.4 Hz, 1H), 3.52 (dt, J=11.9, 4.5 Hz, 1H), 3.45 (dt, J=12.1, 1.8 Hz, 1H), 2.23 (dm, J=13.8 Hz, 1H), 2.14 (app. dq, J=13.1, 4.4 Hz, 1H).

Intermediate 4

(3R,4S)-3-(3-amino-4-oxo-4,5-dihydro-1H-pyrazolo [4,3-c]pyridin-1-yl)tetrahydro-2H-pyran-4-carbonitrile

I-4

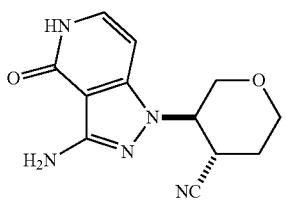

10% Palladium on carbon (1.06 g, 10 wt. %) was added to a solution of (3R,4S)-3-(3-amino-4-(benzyloxy)-1H-pyrazolo[4,3-c]pyridin-1-yl)tetrahydro-2H-pyran-4-carbonitrile (3.49 g, 10.0 mmol) (I-3B) in a mixture of EtOAc (75 mL) and MeOH (25 mL) at room temperature. The flask was sealed and degassed by evacuation and backfill with hydrogen (×3) and stirred under a hydrogen balloon at room temperature for 18 hours. The mixture was diluted with MeOH, filtered through CELITE® (Celite Corporation, Lompo, Calif. USA), and the filtrate was concentrated in vacuo to give the title compound as a solid. LRMS (ESI) calc'd for $C_{12}H_{14}N_5O_2$ [M+H]$^+$: 260, found 260.

Intermediates 5, 6, 7 and 8

(3R,4S or 3S,4R)-3-(3-Amino-4-(benzyloxy)-1H-pyrazolo[4,3-c]pyridin-1-yl)oxepane-4-carbonitrile (I-5A) and (3S,4R or 3R,4S)-3-(3-Amino-4-(benzyloxy)-1H-pyrazolo[4,3-c]pyridin-1-yl)oxepane-4-carbonitrile (I-5B)

I-5A

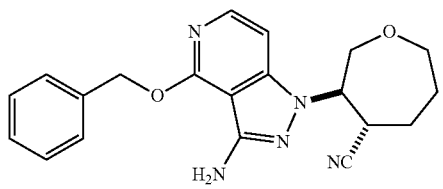

I-5B

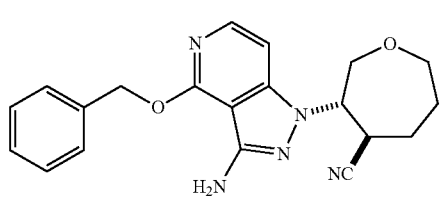

(3R,4R or 3S,4S)-3-(3-amino-4-(benzyloxy)-1H-pyrazolo[4,3-c]pyridin-1-yl)oxepane-4-carbonitrile (I-6A) and (3S,4S or 3R,4R)-3-(3-amino-4-(benzyloxy)-1H-pyrazolo[4,3-c]pyridin-1-yl)oxepane-4-carbonitrile (I-6B)

I-6A

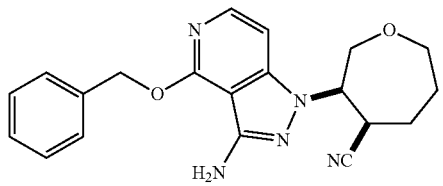

I-6B

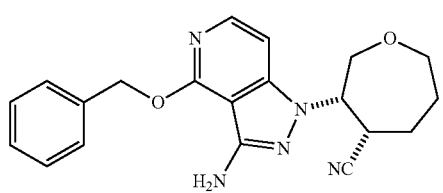

(4R,5S or 4S,5R)-5-(3-amino-4-(benzyloxy)-1H-pyrazolo[4,3-c]pyridin-1-yl)oxepane-4-carbonitrile (I-7A) and (4S,5R or 4R,5S)-5-(3-amino-4-(benzyloxy)-1H-pyrazolo[4,3-c]pyridin-1-yl)oxepane-4-carbonitrile (I-7B)

I-7A
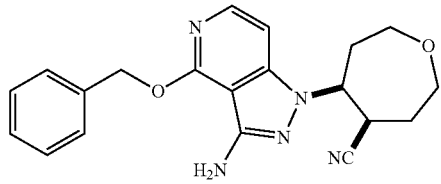

I-7B
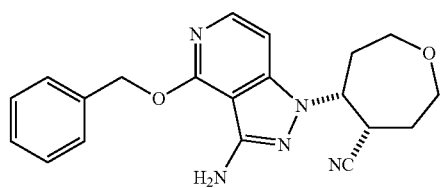

(4S,5S or 4R,5R)-5-(3-amino-4-(benzyloxy)-1H-pyrazolo[4,3-c]pyridin-1-yl)oxepane-4-carbonitrile (I-8A); (4R,5R or 4S,5S)-5-(3-amino-4-(benzyloxy)-1H-pyrazolo[4,3-c]pyridin-1-yl)oxepane-4-carbonitrile (I-8B)

I-8A
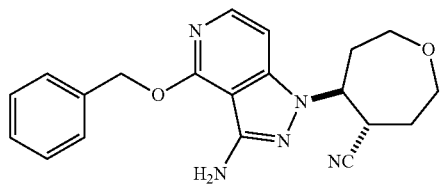

I-8B
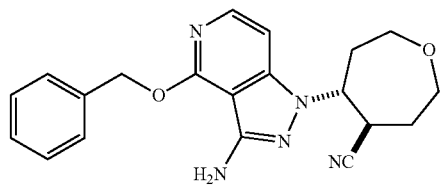

Step 1: oxepan-4-one

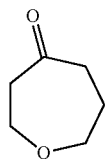

To a stirred solution of dihydro-2H-pyran-4(3H)-one (16.8 mL, 0.100 mol) and boron trifluoride diethyl etherate (25 mL, 0.11 mol) in dichloromethane (400 mL) at −25° C. was added (trimethylsily)diazomethane (100 mL, 110 mmol, 2.0 M in hexane) slowly via syringe. The reaction mixture was stirred for 2.5 hours at −25° C. The reaction mixture was diluted with water (500 mL) and extracted with dichloromethane (×3). The organic layer was washed with a mixture of saturated aqueous ammonium chloride/ammonium hydroxide (10/1) and brine, dried over anhydrous sodium sulfate and filtered. The filtrate was concentrated in vacuo and the resulting residue was purified by silica chromatography, eluting with 1:10 EtOAc:petroleum ether to afford of oxepan-4-one: $^1$H NMR (300 MHz, CDCl$_3$) δ 3.88-3.84 (m, 4H), 2.71-2.65 (m, 4H), 1.89-1.81 (m, 2H).

Step 2: 4-((trimethylsilyl)oxy)oxepane-4-carbonitrile

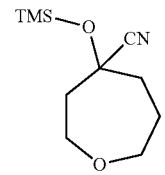

Into a 250 ml, round-bottom flask was placed a solution of oxepan-4-one (5.8 g, 0.051 mol) in dichloromethane (100 mL). Zinc iodide (0.81 g, 2.5 mmol) and trimethylsilyl cyanide (6.04 g, 60.9 mol) were added at 0° C. The resulting mixture was stirred for 90 minutes at ambient temperature and then quenched by addition of water (100 mL). The resulting solution was extracted with dichloromethane (×3) and the combined organic layers were washed with brine, dried over anhydrous sodium sulfate and filtered. The filtrate was concentrated in vacuo and purified by silica chromatography, eluting with 3:1 petroleum ether:EtOAc to afford 4-((trimethylsilyl)oxy)oxepane-4-carbonitrile: $^1$H NMR (300 MHz, CDCl$_3$) δ 3.78-3.72 (m, 2H), 3.70-3.64 (m, 2H), 2.19-1.83 (m, 6H), 0.26 (s, 9H).

Step 3: 2,3,6,7-tetrahydrooxepine-4-carbonitrile and 2,5,6,7-tetrahydrooxepine-4-carbonitrile

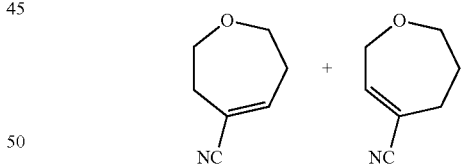

To a solution of 4-((trimethylsilyl)oxy)oxepane-4-carbonitrile (2.0 g, 9.4 mmol) in pyridine (10 mL), was added phosphoryl trichloride (6.9 mL, 75 mmol). The resulting mixture was refluxed for 16 hours, cooled to ambient temperature, and water (50 mL) was then added to quench the reaction. The mixture was extracted with ethyl acetate (×3) and the combined organic layers were washed with brine, dried over anhydrous sodium sulfate and filtered. The filtrate was concentrated in vacuo and the residue was purified by silica chromatography, eluting with 1:1 ethyl acetate:petroleum ether to afford a mixture of 2,3,6,7-tetrahydrooxepine-4-carbonitrile and 2,5,6,7-tetrahydrooxepine-4-carbonitrile (1/2 ratio on $^1$H NMR). 2,3,6,7-tetrahydrooxepine-4-carbonitrile: $^1$H NMR (300 MHz, CDCl$_3$) δ 6.82-6.78 (m, 1H), 3.80-3.69 (m, 4H), 2.64-2.62 (m, 4H), 2.56-

2.50 (m, 2H); and 2,5,6,7-tetrahydrooxepine-4-carbonitrile: ¹H NMR (300 MHz, CDCl₃) δ 6.56-6.54 (m, 1H), 4.27-4.25 (m, 2H), 3.86-3.81 (m, 2H), 2.60-2.50 (m, 2H), 1.99-1.97 (m, 2H).

Step 4: (3R,4S or 3 S,4R)-3-(3-Amino-4-(benzyloxy)-1H-pyrazolo[4,3-c]pyridin-1-yl)oxepane-4-carbonitrile (I-5A); (3S,4R or 3R,4S)-3-(3-amino-4-(benzyloxy)-1H-pyrazolo[4,3-c]pyridin-1-yl)oxepane-4-carbonitrile (I-5B); (3R,4R or 3 S,4S)-3-(3-amino-4-(benzyloxy)-1H-pyrazolo[4,3-c]pyridin-1-yl)oxepane-4-carbonitrile (I-6A); (3S,4S or 3R,4R)-3-(3-amino-4-(benzyloxy)-1H-pyrazolo[4,3-c]pyridin-1-yl)oxepane-4-carbonitrile (I-6B); (4R,5S or 4S,5R)-5-(3-amino-4-(benzyloxy)-1H-pyrazolo[4,3-c]pyridin-1-yl)oxepane-4-carbonitrile (I-7A); (4S,5R or 4R,5S)-5-(3-amino-4-(benzyloxy)-1H-pyrazolo[4,3-c]pyridin-1-yl)oxepane-4-carbonitrile (I-7B); (4S,5S or 4R,5R)-5-(3-amino-4-(benzyloxy)-1H-pyrazolo[4,3-c]pyridin-1-yl)oxepane-4-carbonitrile (I-8A); (4R,5R or 4S,5S)-5-(3-amino-4-(benzyloxy)-1H-pyrazolo[4,3-c]pyridin-1-yl)oxepane-4-carbonitrile (I-8B)

To a nitrogen purged flask, was added 4-(benzyloxy)-1H-pyrazolo[4,3-c]pyridin-3-amine (6.34 g, 26.5 mmol) (I-1), a mixture of 2,3,6,7-tetrahydrooxepine-4-carbonitrile and 2,5,6,7-tetrahydrooxepine-4-carbonitrile (6.5 g, 0.053 mol) and acetonitrile (24 mL). This solution was stirred for 15 minutes then 1,5-diazabicyclo[4.3.0]non-5-ene (9.6 g, 0.053 mol) was added. The reaction was stirred for 16 hours at 80° C. and then water (30 mL) was added and the mixture was extracted with ethyl acetate (×3). The combined organic layers were washed with brine, dried over anhydrous sodium sulfate and filtered. The filtrate was concentrated in vacuo and the resulting residue was purified by silica chromatography, eluting with 1:1 ethyl acetate:petroleum ether to afford a mixture of isomers of both 3-(3-amino-4-(benzyloxy)-1H-pyrazolo[4,3-c]pyridin-1-yl)oxepane-4-carbonitrile and 5-(3-amino-4-(benzyloxy)-1H-pyrazolo[4,3-c]pyridin-1-yl)oxepane-4-carbonitrile.

The four isomers of 3-(3-amino-4-(benzyloxy)-1H-pyrazolo[4,3-c]pyridin-1-yl)oxepane-4-carbonitrile was purified by chiral Prep-HPLC with a CHIRALCEL® IC-H, 4.6×100 mm, 3 μm column, using 30% of ethanol (with 0.1% DEA) in hexanes (with 0.1% DEA) to afford the desired compounds as solids.

(3R,4S or 3S,4R)-3-(3-Amino-4-(benzyloxy)-1H-pyrazolo[4,3-c]pyridin-1-yl)oxepane-4-carbonitrile eluted at 3.9 minutes (I-5A) and (3S,4R or 3R,4S)-3-(3-amino-4-(benzyloxy)-1H-pyrazolo[4,3-c]pyridin-1-yl)oxepane-4-carbonitrile eluted at 4.5 minutes (I-5B): ¹H NMR (400 MHz, CDCl₃) δ 7.91 (d, J=6.0 Hz, 1H), 7.52-7.41 (m, 2H), 7.39-7.29 (m, 3H), 6.87 (d, J=6.0 Hz, 1H), 5.58 (s, 2H), 4.54 (s, 1H), 4.62-4.58 (m, 1H), 4.05-4.00 (m, 1H), 3.92-3.78 (m, 2H), 3.53-3.46 (m, 1H), 2.30-2.29 (m, 1H), 2.14-2.01 (m, 3H).

(3R,4R or 3S,4S)-3-(3-Amino-4-(benzyloxy)-1H-pyrazolo[4,3-c]pyridin-1-yl)oxepane-4-carbonitrile eluted at 5.4 minutes (I-6A) and (3S,4S or 3R,4R)-3-(3-amino-4-(benzyloxy)-1H-pyrazolo[4,3-c]pyridin-1-yl)oxepane-4-carbonitrile eluted at 6.1 minutes (I-6B): ¹H NMR (400 MHz, CDCl₃) δ 7.90 (d, J=6.4 Hz, 1H), 7.52-7.43 (m, 2H), 7.41-7.37 (m, 3H), 6.82 (d, J=6.4 Hz, 1H), 5.59 (s, 2H), 4.81-4.75 (m, 1H), 4.54 (s, 2H), 4.33-4.21 (m, 2H), 4.04-3.89 (m, 1H), 3.88-3.85 (m, 1H), 3.44-3.41 (m, 1H), 2.59-2.54 (m, 1H), 2.08-2.04 (m, 2H), 1.96-1.93 (m, 1H).

The four isomers of 5-(3-amino-4-(benzyloxy)-1H-pyrazolo[4,3-c]pyridin-1-yl)oxepane-4-carbonitrile were purified by chiral Prep-HPLC using a CHIRACEL® OJ-3, 2.0×250 mm, 3 μm, eluting with 25% propan-2-ol (with 0.1% DEA) in hexanes (with 0.1% DEA) to afford the desired isomers as solids.

(4R,5S or 4S,5R)-5-(3-amino-4-(benzyloxy)-1H-pyrazolo[4,3-c]pyridin-1-yl)oxepane-4-carbonitrile eluted at 5.5 minutes (I-7A) and (4S,5R or 4R,5S)-5-(3-amino-4-(benzyloxy)-1H-pyrazolo[4,3-c]pyridin-1-yl)oxepane-4-carbonitrile eluted at 6.7 minutes (I-7B): ¹H NMR (400 MHz, CDCl₃) δ 7.91 (d, J=6.4 Hz, 1H), 7.52 (d, J=7.2 Hz, 2H), 7.45-7.38 (m, 3H), 6.84 (d, J=6.4 Hz, 1H), 5.58 (s, 2H), 4.69-4.63 (m, 1H), 4.53 (s, 2H), 4.01-3.92 (m, 2H), 3.81 (m, 2H), 3.63 (m, 1H), 2.49 (m, 1H), 2.32 (m, 1H), 2.24 (m, 1H), 2.16 (m, 1H).

(4S,5S or 4R,5R)-5-(3-Amino-4-(benzyloxy)-1H-pyrazolo[4,3-c]pyridin-1-yl)oxepane-4-carbonitrile eluted at 8.0 minutes (I-8A) and (4R,5R or 4S,5S)-5-(3-amino-4-(benzyloxy)-1H-pyrazolo[4,3-c]pyridin-1-yl)oxepane-4-carbonitrile eluted at 10.3 minutes (I-8B): ¹H NMR (400 MHz, CDCl₃) δ 7.88 (d, J=6.0 Hz, 1H), 7.51 (d, J=7.2 Hz, 2H), 7.45-7.37 (m, 3H), 6.81 (d, J=6.4 Hz, 1H), 5.57 (s, 2H), 4.73-4.69 (m, 1H), 4.55 (s, 2H), 4.09-3.98 (m, 1H), 3.91 (m, 2H), 3.86 (m, 1H), 3.37 (s, 1H), 2.91-2.84 (m, 1H), 2.40 (m, 1H), 2.24 (m, 1H), 2.16 (m, 1H).

Intermediate 9

5-bromo-2-(2,2,2-trifluoroethyl)-2,3-dihydro-1H-isoindol-1-one

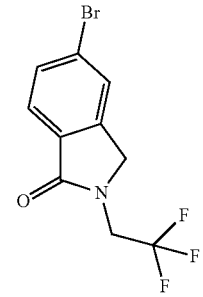

I-9

5-Bromo-2,3-dihydro-1H-isoindol-1-one (100 mg, 0.47 mmol) was dissolved in DMF (4.7 mL) and stirred at 0° C. NaH (38 mg, 0.94 mmol, 60 wt. % dispersion in oil) was carefully added in two portions, and the resulting mixture was allowed to stir at 0° C. for 15 minutes before 2,2,2-trifluoroethyl trifluoromethanesulfonate (110 mg, 0.47 mmol) was added. The mixture was allowed to stir at 0° C. for 30 minutes before saturated aqueous NaHCO₃ (10 mL) was carefully added, and the mixture was extracted with EtOAc. The organic layer was washed with water, brine, dried over anhydrous MgSO₄, filtered, and concentrated in vacuo. The residue was purified by silica chromatography, eluting with a 0-20% EtOAc/hexanes gradient. LRMS (ESI) calc'd for $C_{10}H_8BrF_3NO$ [M+H]⁺: 294, found: 294.

Intermediate 10-1

5-bromo-2-(tert-butyl)-2,3-dihydrobenzo[d]isothiazole 1,1-dioxide

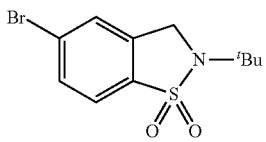
I-10-1

Step 1: 4-bromo-2-methylbenzene-1-sulfonyl chloride

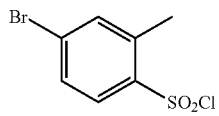
I-10a

Chlorosulfonic acid (63 g, 0.54 mol) was added slowly to a cold solution (0° C.) of 1-bromo-3-methylbenzene (10.0 g, 58 mmol) in CHCl₃ (100 mL). The reaction was allowed to proceed with stirring for 2 hours at 0° C., then reaction mixture was poured into ice water and extracted with EtOAc, and the organic layer was washed with brine, dried over NaSO₄, filtered and concentrated in vacuo to afford compound I-10a as a solid. $^1$H NMR (400 MHz, CDCl₃): δ 7.90 (d, J=8.4 Hz, 1H), 7.59-7.53 (m, 2H), 2.75 (s, 3H).

Step 2: 4-bromo-N-(tert-butyl)-2-methylbenzenesulfonamide

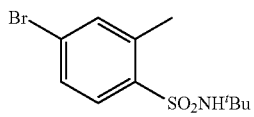
I-10b

To a solution of I-10a (2.0 g, 7.4 mmol) in CH₂Cl₂ (15 mL) was added a solution of 2-methylpropan-2-amine (0.65 g, 8.9 mmol) and triethylamine (0.90 g, 8.9 mmol) in CH₂Cl₂ (30 mL) at 0° C. The reaction mixture was stirred at 0° C. for 2 hours and then at room temperature for 16 hours. The mixture was washed with 0.1 M HCl, saturated aqueous NaHCO₃, dried over Na₂SO₄, filtered and the filtrate was concentrated in vacuo. After removal of the solvent under reduced pressure, I-10b was obtained as a solid. $^1$H NMR (400 MHz, DMSO-d6): δ 7.78 (d, J=8.4 Hz, 1H), 7.63 (d, J=1.6 Hz, 1H), 7.59-7.56 (m, 2H), 2.57 (s, 3H), 1.09 (s, 9H).

Step 3: 5-bromo-2-(tert-butyl)benzo[d]isothiazol-3(2H)-one 1,1-dioxide

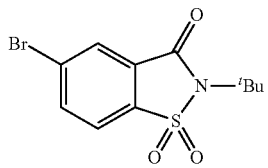
I-10c

A mixture of H₅IO₆ (5.9 g, 26 mmol) in acetonitrile (50 mL) was stirred at room temperature for 1 hour, then CrO₃ (33 mg, 0.33 mmol) was added followed by acetic anhydride (2.67 g, 26.2 mmol). The resulting orange solution was cooled to 0° C., and I-10b (1.0 g, 3.3 mmol) was added. After stirring at 0° C. for 15 minutes, the reaction was allowed to warm to room temperature and was stirred for 16 hours. The solvent was removed in vacuo, and the residue was extracted with EtOAc (×3), the combined organic layers were washed with saturated aqueous NaHCO₃, brine, dried over Na₂SO₄, filtered and the filtrate was concentrated in vacuo. The residue was purified by silica chromatography, eluting with 5% EtOAc in hexanes and the desired fractions were concentrated in vacuo to afford I-10c as a solid. $^1$H NMR (400 MHz, DMSO-d6): δ 8.82-8.14 (m, 3H), 1.66 (s, 9H).

Step 4: 5-bromo-2-(tert-butyl)-2,3-dihydrobenzo[d]isothiazole-1,1-dioxide

To a solution of I-10c (0.20 g, 0.63 mmol) in THF (4 mL) was added BH₃.Me₂S (240 mg, 3.16 mmol). The reaction mixture was refluxed for 16 hours. After being cooled to room temperature, the reaction was quenched with 2 M HCl, and extracted with EtOAc (×2), the combined extracts were washed with brine, dried over Na₂SO₄, filtered, and the filtrate was concentrated in vacuo. The residue was purified by preparative TLC to afford compound I-10-1. $^1$H NMR (400 MHz, DMSO-d6): δ 7.83-7.56 (m, 3H), 4.55 (s, 2H), 1.46 (s, 9H).

Following an analogous method to that outlined for Intermediate 10-1 above, the following intermediates in Table 1 were prepared:

TABLE 1

| Intermediate | Structure | Name | $^1$H NMR or LRMS |
|---|---|---|---|
| I-10-2 | 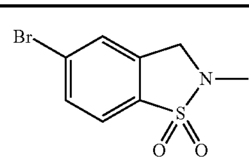 | 5-bromo-2-(methyl)-2,3-dihydrobenzo[d]isothiazole-1,1-dioxide | $^1$H NMR (400 MHz, CDCl₃): δ 7.63-7.60 (m, 2H), 7.5 (s, 1H), 4.25 (s, 2H), 2.89 (s, 3H). |

TABLE 1-continued

| Intermediate | Structure | Name | ¹H NMR or LRMS |
|---|---|---|---|
| I-10-3 | ![structure] | 5-bromo-2-(2,2,2-trifluoroethyl)-2,3-dihydrobenzo[d]isothiazole 1,1-dioxide | ¹H NMR (600 MHz, CDCl₃): δ 7.71 (s, 2H), 7.60 (s, 1H), 4.55 (s, 2H), 3.85 (q, 2H, J = 8.4 Hz). |
| I-10-4 | ![structure] | 5-bromo-2,3-dihydrobenzo[d]isothiazole 1,1-dioxide | ¹H NMR (600 MHz, DMSO-d6): δ 7.96 (bs, 1H), 7.88 (s, 1H), 7.83 (d, 1H, J = 8.0 Hz), 7.79 (d, 1H, J = 8.4 Hz), 4.44 (d, 2H, J = 4.8 Hz). |

Intermediate 11

1-(4-bromophenyl)-2,2,2-trifluoroethanamine

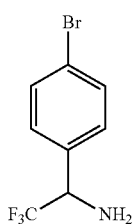

I-11

To a solution of 1-(4-bromophenyl)-2,2,2-trifluoroethanone (1.00 g, 3.95 mmol) in toluene (14 mL) at room temperature, was added (dropwise) a solution of lithium bis(trimethylsilyl)amide (4.35 mL, 4.35 mmol, 1M in THF). The reaction was stirred at room temperature for 15 minutes and then BH₃.THF (7.90 mL, 7.90 mmol, 1M in THF) was added. The reaction was stirred at room temperature for 20 minutes, then quenched at 0° C. by slow addition of aqueous NaOH (5.93 mL, 11.9 mmol, 2M). The mixture was stirred at room temperature for 90 minutes, then the organic layer was separated and washed with 1N aqueous NaOH solution, dried over Na₂SO₄, filtered and concentrated in vacuo. SFC separation of the enantiomers on the crude reaction mixture was achieved using a CHIRALPAK® AZ-H, with 7% methanol modifier in CO₂: retention times=2.4 (I-11A) & 2.9 (I-11B) minutes. LRMS (ESI) calc'd for C₈H₈NBrF₃ [M+H]⁺: 254, found 254. ¹H NMR (600 MHz, CDCl₃): δ 7.53 (d, J=8.5 Hz, 2H), 7.32 (d, J=8.5 Hz, 2H), 4.38 (q, J=7.5 Hz, 1H), 1.78 (br s, 2H).

Intermediate 12-1

4-bromo-N-(tert-butyl)-N-methylbenzenesulfonamide

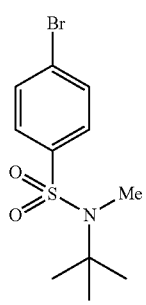

I-12-1

To a solution of 4-bromo-N-(tert-butyl)benzenesulfonamide (1.00 g, 3.42 mmol) and potassium carbonate (0.946 g, 6.84 mmol) in DMF (20 mL) was added methyl iodide (0.43 mL, 6.8 mmol) at room temperature. The reaction was stirred for 6 hours, then quenched by addition of water and extracted with EtOAc (×3). The organic layers were dried over sodium sulfate, filtered, and concentrated in vacuo and purified by silica chromatrography, eluting with 0-10% EtOAc in hexanes to give I-12-1. LRMS (ESI) calc'd for C₁₁H₁₇NBrO₂SNa[M+Na]⁺: 328, found 328. ¹H NMR (600 MHz, CDCl₃): δ 7.69 (d, J=8.7 Hz, 2H), 7.62 (d, J=8.7 Hz, 2H), 2.97 (s, 3H), 1.35 (s, 9H).

The following intermediates in Table 2 were made in analogy to I-12-1 above, using Cs₂CO₃ at 50° C. or NaH at 0-25° C. and Intermediate I-10-4.

TABLE 2

| Intermediate | Structure | Name | LRMS or ¹H NMR |
|---|---|---|---|
| I-12-2 | ![structure] | 5-bromo-2-(2-methoxyethyl)-2,3-dihydrobenzo[d]isothiazole 1,1-dioxide | LRMS (ESI) calc'd for C₁₀H₁₃BrNO₃S [M + H]⁺: 306, found 306. |

TABLE 2-continued

| Intermediate | Structure | Name | LRMS or ¹H NMR |
|---|---|---|---|
| I-12-3 | (structure) | tert-butyl 2-(5-bromo-1,1-dioxidobenzo[d]isothiazol-2(3H)-yl)acetate | ¹H NMR (600 MHz, CDCl₃): δ 7.65 (s, 2H), 7.54 (s, 2H), 4.59 (s, 2H), 3.95 (s, 2H), 1.44 (s, 9H). |
| I-12-4A | (structure) | (R or S) 5-bromo-2,3-dimethyl-2,3-dihydrobenzo[d]isothiazole-1,1-dioxide (SFC resolution was achieved using a CHIRALPAK ® AS-H, 20% of a 40%/60% MeOH/CH₃CN solvent system. Tr = 1.8 minutes) | ¹H NMR (500 MHz, CDCl₃): δ 7.67-7.65 (m, 2H), 7.56 (s, 1H), 4.30 (m, 1H), 2.90 (s, 3H), 1.56 (d, J = 6.0 Hz, 3H). LRMS (ESI) calc'd for C₉H₁₁BrNO₂S [M + H]⁺: 277, found 277. |
| I-12-4B | (structure) | (R or S) 5-bromo-2,3-dimethyl-2,3-dihydrobenzo[d]isothiazole-1,1-dioxide (SFC resolution was achieved using a CHIRAL ® AS-H, 20% of a 40%/60% MeOH/CH₃CN solvent system. Tr = 2.2 minutes) | ¹H NMR (500 MHz, CDCl₃): δ 7.67-7.65 (m, 2H), 7.56 (s, 1H), 4.30 (m, 1H), 2.90 (s, 3H), 1.56 (d, J = 6.0 Hz, 3H). LRMS (ESI) calc'd for C₉H₁₁BrNO₂S [M + H]⁺: 277, found 277. |

Intermediate 13

1-bromo-4-(tert-butylsulfonyl)benzene

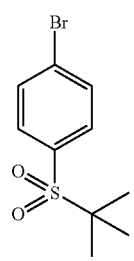

I-13

To a solution of (4-bromophenyl)(tert-butyl)sulfane (1.00 g, 4.08 mmol) in DCM (10.0 mL) was added m-CPBA (2.01 g, 8.97 mmol, 77 wt. %) at room temperature. The resulting solution was stirred at room temperature for one hour and then quenched with saturated aqueous Na₂S₂O₃ and saturated aqueous Na₂CO₃. The reaction was extracted with DCM (×3), dried over sodium sulfate, filtered and concentrated in vacuo to afford I-13 as a solid. ¹H NMR (600 MHz, DMSO-d6): δ 7.89 (d, J=8.7 Hz, 2H), 7.75 (d, J=8.7 Hz, 2H), 1.24 (s, 9H).

Intermediate 14

1-bromo-4-((2,3-dimethylbutan-2-yl)sulfonyl)benzene

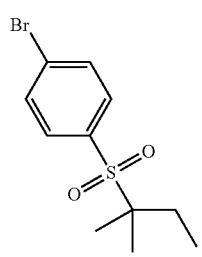

I-14-1

To a solution of 1-bromo-4-(isopropylsulfonyl)benzene (100 mg, 0.38 mmol) in dry THF (2 mL) was slowly added LDA (0.19 mL, 0.38 mmol, 2.9 M in THF/heptane/ethylbenzene) at −78° C. After 1.5 hours, iodoethane (91 μL, 1.1 mmol) was added and the mixture was allowed to warm up to room temperature overnight. The mixture was diluted with saturated aqueous ammonium chloride, extracted with ethyl acatate (×3), and the combined organic layers were dried over Na₂SO₄, filtered and concentrated in vacuo. The residue was purified by silica chromatography, eluting with 0-40% ethyl acetate/hexanes to afford intermediate I-14-1 as a solid. ¹H NMR (600 MHz, CDCl₃): δ 7.71 (d, J=8.8 Hz, 2H), 7.67 (d, J=8.2 Hz, 2H), 1.71 (q, J=7.6 Hz, 2H), 1.25 (s, 6H), 0.93 (t, J=7.6 Hz, 3H).

The following intermediates in Table 3 were prepared by analogy using the procedure outlined above for I-14-1.

TABLE 3

| Intermediate | Structure | Compound Name | NMR |
|---|---|---|---|
| I-14-2 | 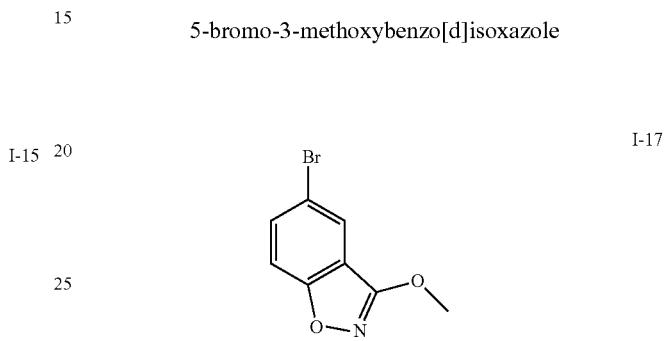 | 1-bromo-4-((2,3-dimethylbutan-2-yl)sulfonyl)benzene | $^1$H NMR (600 MHz, CDCl$_3$): δ 7.73 (d, J = 8.4 Hz, 2H), 7.69 (d, J = 8.5 Hz, 2H), 2.19 (septet, J = 6.4 Hz, 1H), 1.23 (s, 6H), 1.08 (d, 6H, J = 6.6 Hz). |

Intermediate 15

5-bromo-2-isopropyl-2,3-dihydro-1H-isoindole

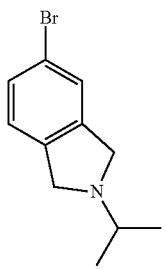

I-15

To a solution of 5-bromo-2,3-dihydro-1H-isoindole hydrochloride (2.00 g, 8.53 mmol) in N,N-dimethylformamide (50 mL), was added sodium hydride (0.850 g, 60% in mineral oil, 21.3 mmol). The mixture was stirred for 45 minutes at 20° C. and then 2-iodopropane (2.17 g, 12.8 mmol) was added dropwise. The resulting solution was stirred for 16 hours at 50° C. in an oil bath, cooled to ambient temperature and quenched by addition of water (80 mL). The reaction was extracted with ethyl acetate (×3) and the combined organic layers were washed with water, brine, and dried over anhydrous sodium sulfate and filtered. The filtrate was concentrated in vacuo to afford I-15 as a solid: LRMS (ESI) calc'd for C$_{11}$H$_{14}$BrN [M+H]$^+$: 240, 242 (1:1), found 240, 242 (1:1); $^1$H NMR (300 MHz, CDCl$_3$): δ 7.46-7.32 (m, 2H), 7.07 (d, J=7.8 Hz, 1H), 4.92 (d, J=7.8 Hz, 4H), 2.79-2.71 (m, 1H), 1.19 (d, J=6.3 Hz, 6H).

Intermediate 16

5-bromo-2-isobutylisoindoline

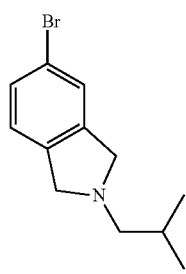

I-16

To a mixture of 5-bromoisoindoline hydrochloride (1.50 g, 6.40 mmol) in MeOH (50 mL) and isobutyraldehyde (2.31 g, 32.0 mmol) was added (portionwise) NaBH$_4$ (1.45 g, 38.4 mmol) at 0° C. The above mixture was stirred at 15° C. for one hour, then cooled and quenched by addition of water. The mixture was extracted with ethyl acetate (×3) and the combined organic fractions were washed with brine, dried over Na$_2$SO$_4$, filtered and the solvent was evaporated in vacuo. The residue was purified by silica chromatography, eluting with 1:5 EtOAc/petroleum ether to give I-16 as a oil. $^1$H NMR (400 MHz, CDCl$_3$): δ 7.41 (d, J=8.1 Hz, 1H), 7.35 (s, 1H), 7.07 (d, J=8.1 Hz, 1H), 4.50 (q, J=9.3 Hz, 2H), 4.14 (q, J=10.2 Hz, 2H), 2.87 (q, J=5.4 Hz, 2H), 2.40-2.35 (m, 1H), 1.03 (d, J=6.9 Hz, 6H).

Intermediate 17

5-bromo-3-methoxybenzo[d]isoxazole

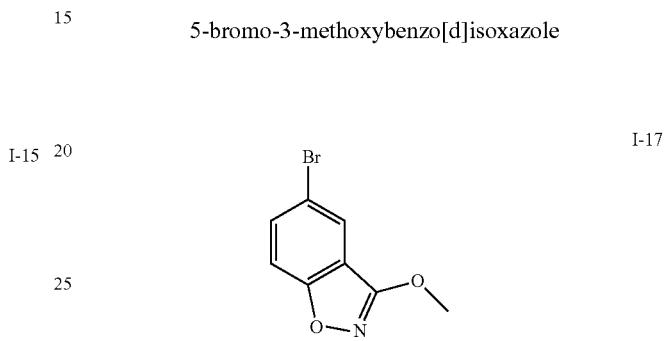

I-17

To a solution of 5-bromo-3-chlorobenzo[d]isoxazole (1.74 g, 7.50 mmol) in MeOH (20.0 mL) was added sodium methanolate (2.03 g, 37.5 mmol) in a 20 mL Biotage microwave vial (Biotage, Charlotte, N.C. USA). The vial was sealed and heated at 120° C. for 1.5 hours in the microwave. The reaction was diluted with ethyl acetate and washed with water, brine, and the organic layer was dried over sodium sulfate, filtered, silica gel was added, and the slurry was concentrated in vacuo. The residue was purified by silica chromatography eluting with 10-60% CH$_2$Cl$_2$/hexanes to give I-17 as a solid. $^1$H NMR (500 MHz, DMSO-d6): δ 8.02 (d, 1H, J=2.0 Hz), 8.24 (dd, 1H, J=8.7, 2.0 Hz), 7.69 (d, 1H, J=8.7 Hz), 4.15 (s, 3H).

Intermediate 18

1-(4-bromophenyl)-5,5-dimethyl-2-oxabicyclo[2.2.2]octan-3-one

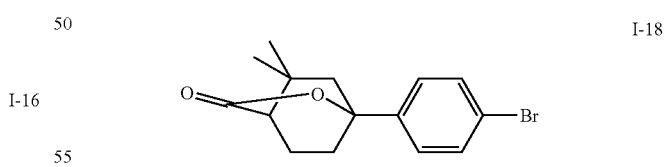

I-18

To 1-bromo-4-iodobenzene (600 mg, 2.12 mmol) in THF (7.1 mL) at −78° C. was added (dropwise) n-BuLi (1.46 mL, 2.33 mmol, 1.60 M in hexanes) and the reaction was stirred at −78° C. for 2 hours. A solution of methyl 2,2-dimethyl-4-oxocyclohexanecarboxylate (430 mg, 2.33 mmol) in THF (1.5 mL) was then added dropwise and the reaction was stirred to room temperature overnight. The reaction was quenched by pouring into a separatory funnel containing water and was extracted with ethyl acetate (×3). The organic layers were combined and dried over Na$_2$SO$_4$, filtered, and concentrated in vacuo. The crude product was then purified by silica chromatography, eluting with 0-50% EtOAc/hexane. The product was collected and concentrated to afford I-18 as a oil. LRMS (ESI) calc'd for $C_{15}H_{18}BrO_2$ [M+H]$^+$: 309, found 309.

Intermediates 19-1 and 19-2

(R or S) 1-bromo-4-(1,1,1-trifluoro-2-methoxypropan-2-yl)benzene

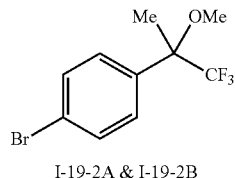 [SMILES: COC(C)(c1ccc(Br)cc1)C(F)(F)F]

I-19-2A & I-19-2B

Step 1: (R or S) 2-(4-bromophenyl)-1,1,1-trifluoropropan-2-ol

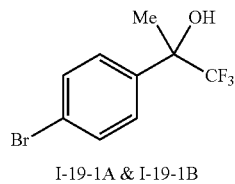 [SMILES: CC(O)(c1ccc(Br)cc1)C(F)(F)F]

I-19-1A & I-19-1B

In an oven dried round bottom flask under $N_2$, was charged 1-(4-bromophenyl)-2,2,2-trifluoroethanone (2.0 g, 7.9 mmol) and THF (13 mL). The solution was cooled to 0° C., and methyl magnesium bromide (17 mL, 23.7 mmol, 1.4 M in diethyl ether) was added. The reaction mixture was warmed to room temperature over 1-2 hours, and was quenched by the addition of saturated aqueous NH$_4$Cl (10 mL). The resulting mixture was extracted with Et$_2$O (×3), and the combined organic layers were concentrated in vacuo to afford a residue that was purified by silica chromatography, eluting with hexanes/EtOAc gradient to yield racemic 2-(4-bromophenyl)-1,1,1-trifluoropropan-2-ol. $^1$H NMR (CDCl$_3$, 500 MHz): δ 7.54 (d, J=8.3 Hz, 2H), 7.47 (d, J=8.3 Hz, 2H), 2.44 (s, 1H), 1.78 (s, 3H). Resolution of enantiomers was achieved by SFC purification using a Chiral Technology AZ-H with 5% MeOH in CO$_2$. Tr=2.6 minutes (Intermediate I-19-1A) & 3.2 minutes (Intermediate I-19-1B).

I-19-1A (S or R)-2-(4-bromophenyl)-1,1,1-trifluoropropan-2-ol. LRMS (ESI) calc'd for $C_9H_9BrF_3O$ [M+H]$^+$: 269, found 269. I-19-1B (S or R)-2-(4-bromophenyl)-1,1,1-trifluoropropan-2-ol. LRMS (ESI) calc'd for $C_9H_9BrF_3O$ [M+H]$^+$: 269, found 269.

Step 2: (R or S) 1-bromo-4-(1,1,1-trifluoro-2-methoxypropan-2-yl)benzene (I-19-2A & I-19-2B)

An oven dried round bottom flask with magnetic sir bar under an atmosphere of N$_2$ was charged with 2-(4-bromophenyl)-1,1,1-trifluoropropan-2-ol I-19-1A (300 mg, 1.10 mmol) and DMF (3.5 mL). The solution was cooled to 0° C., sodium hydride (67 mg, 1.7 mmol, 60% wt. in mineral oil) was added, and the reaction was stirred for 30 minutes. Iodomethane (0.21 mL, 3.3 mmol) was then added and the reaction mixture was warmed to room temperature over 1-2 hours, quenched by addition of saturated aqueous NH$_4$Cl (10 mL), and extracted with Et$_2$O (×3). The combined organic layers were concentrated in vacuo to afford a residue that was purified by silica chromatography, eluting with hexanes/EtOAc gradient, to yield I-19-2A. I-19-2B was prepared in an analogous manner to I-19-2A above, using I-19-1B. $^1$H NMR (CDCl$_3$, 500 MHz): δ 7.54 (d, J=8.2 Hz, 2H), 7.38 (d, J=8.1 Hz, 2H), 3.23 (s, 3H), 1.76 (s, 3H).

Intermediate I-20

(4-bromo-2-methylphenyl)(4,4-difluoropiperidin-1-yl)methanone

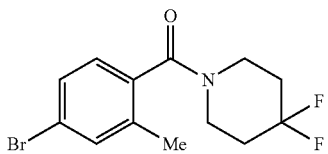

I-20

To a solution of 4-bromo-2-methylbenzoic acid (0.75 g, 3.5 mmol) in DMF (9 mL), was added 1-[bis(dimethylamino)methylene]-1H-1,2,3-triazolo[4,5-b]pyridinium 3-oxid hexafluorophosphate; HATU) (2.6 g, 7.0 mmol), Hunig's base (2.4 mL, 14 mmol), and 4,4-difluoropiperidine (0.84 g, 7.0 mmol). The resulting reaction mixture was stirred for 12-16 hours, concentrated in vacuo, and the resulting crude oil was purified by silica chromatography, eluting with hexanes/EtOAc gradient to yield I-20. $^1$H NMR (500 MHz, CDCl$_3$): δ 7.42-7.37 (m, 2H), 7.05 (d, J=8.1 Hz, 1H), 4.02 (m, 1H), 3.82 (m, 1H), 3.36 (m, 2H), 2.30 (s, 3H), 2.09 (m, 2H), 1.88 (m, 2H).

Intermediate I-21

N-(1-(4-bromophenyl)-2,2,2-trifluoroethyl)-2-methylpropan-2-amine

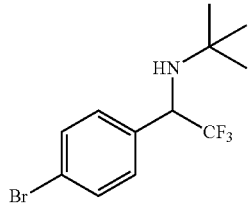

I-21-1

Step 1: 1-(4-bromophenyl)-2,2,2-trifluoroethanol

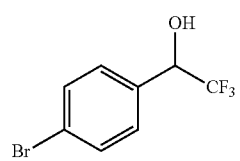

I-21-1a 1-(4-Bromophenyl)-2,2,2-trifluoroethanone (1.73 g, 6.84 mmol) was dissolved in THF (3.4 mL) and treated with sodium borohydride (0.285 g, 7.52 mmol) at 0° C. The reaction was then warmed to room temperature and stirred overnight. The reaction mixture was diluted with DCM and washed with water and brine. The combined organic layers were dried over Na$_2$SO$_4$, filtered, and the filtrate was concentrated in vacuo. The residue was purified by silica chromatography, eluting with 5-30% EtOAc in hexanes and the desired fractions were concentrated in vacuo to afford I-21-1a. $^1$H NMR (500 MHz, CDCl$_3$) δ 7.56 (d, J=8.5 Hz, 2H), 7.36 (d, J=8.5 Hz, 2H), 5.06-4.96 (m, 1H), 2.63 (d, J=4.5 Hz, 1H).

Step 2: 1-(4-bromophenyl)-2,2,2-trifluoroethyl trifluoromethanesulfonate

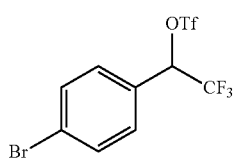

I-21-1b

A solution of 1-(4-bromophenyl)-2,2,2-trifluoroethanol (1.5 g, 5.9 mmol) and 2,6-lutidine (1.10 mL, 9.41 mmol) in DCE (12 mL) was cooled to −15° C. and triflic anhydride (8.82 mL, 8.82 mmol, 1.0 M in DCM) was added dropwise. The reaction stirred between −15° C. and room temperature for 1 hours, then diluted with DCM and washed with water, 1N aqueous HCl, and brine. The combined organic layers were dried over Na$_2$SO$_4$, filtered, and the filtrate was concentrated in vacuo to give I-21-1b as a liquid. $^1$H NMR (500 MHz, CDCl$_3$) δ 7.64 (d, J=8.3 Hz, 2H), 7.37 (d, J=8.3 Hz, 2H), 5.85-5.74 (m, 1H).

Step 3: N-(1-(4-bromophenyl)-2,2,2-trifluoroethyl)-2-methylpropan-2-amine 1-(4-Bromophenyl)-2,2,2-trifluoroethyl trifluoromethanesulfonate (7.59 g, 19.6 mmol) was dissolved in cyclohexane (70 mL) and 2-methylpropan-2-amine (6.23 mL, 58.8 mmol), DMAP (0.240 g, 1.96 mmol), and ground, dried potassium carbonate (5.42 g, 39.2 mmol) (dried over vacuum at 60° C. for one hour) was added. The reaction mixture was heated to 75° C. and stirred for 48 hours. The reaction mixture was diluted with DCM, washed with water, and the combined organic layers were dried over Na$_2$SO$_4$, filtered, and the filtrate was concentrated in vacuo. The residue was purified by silica chromatography, eluting with 2-20% EtOAc in hexanes and the desired fractions were concentrated in vacuo to afford I-21-1 as a liquid. LRMS (ESI) calc'd for C$_{12}$H$_{16}$BrF$_3$N [M+H]$^+$: 310, found 310.

Following analogous methodology to that outlined for Intermediate I-21-1 above, the following intermediates in Table 4 were synthesized. In select cases, the general procedure was modified by not using DMAP and/or the crude product was used as is. In certain instances 2.0-3.0 equivalents of amine and/or 1.5-3.0 equivalents of ground, dried potassium carbonate could also be used.

TABLE 4

| Intermediate | Structure | Name | LCMS |
|---|---|---|---|
| I-21-2 | 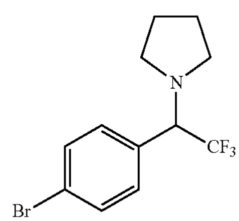 [SMILES: FC(F)(F)C(c1ccc(Br)cc1)N1CCCC1] | 1-(1-(4-bromophenyl)-2,2,2-trifluoroethyl)pyrrolidine | LRMS (ESI) calc'd for C$_{12}$H$_{14}$BrF$_3$N [M + H]$^+$: 308, found 308. |
| I-21-3 | 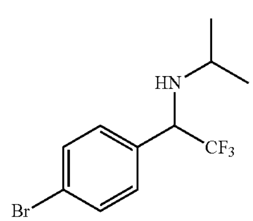 [SMILES: CC(C)NC(c1ccc(Br)cc1)C(F)(F)F] | N-(1-(4-bromophenyl)-2,2,2-trifluoroethyl)propan-2-amine | LRMS (ESI) calc'd for C$_{11}$H$_{14}$BrF$_3$N [M + H]$^+$: 296, found 296. |
| I-21-4 | 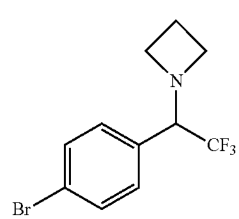 [SMILES: FC(F)(F)C(c1ccc(Br)cc1)N1CCC1] | 1-(1-(4-bromophenyl)-2,2,2-trifluoroethyl)azetidine | LRMS (ESI) calc'd for C$_{11}$H$_{12}$BrF$_3$N [M + H]$^+$: 294, found 294. |

TABLE 4-continued

| Intermediate | Name | LCMS |
|---|---|---|
| I-21-5 | 1-(4-bromophenyl)-N-ethyl-2,2,2-trifluoroethanamine | LRMS (ESI) calc'd for $C_{10}H_{12}BrF_3N$ $[M + H]^+$: 282, found 282. |
| I-21-6 | 1-(1-(4-bromophenyl)-2,2,2-trifluoroethyl)-4-methylpiperazine | LRMS (ESI) calc'd for $C_{13}H_{17}BrF_3N_2$ $[M + H]^+$: 337, found 337. |
| I-21-7 | 1-(1-(4-bromophenyl)-2,2,2-trifluoroethyl)piperazine | LRMS (ESI) calc'd for $C_{12}H_{15}BrF_3N_2$ $[M + H]^+$: 323, found 323. |
| I-21-8 | tert-butyl 2-((1-(4-bromophenyl)-2,2,2-trifluoroethyl)amino)acetate | LRMS (ESI) calc'd for $C_{10}H_9BrF_3NO_2$ $[M - C_4H_9]^+$: 312, found 312. |
| I-21-9 | N-(1-(4-bromophenyl)-2,2,2-trifluoroethyl)-2,2-dimethylcyclopropanamine | LRMS (ESI) calc'd for $C_{13}H_{16}BrF_3N$ $[M + H]^+$: 322, found 322. |
| I-21-10 | 1-(4-bromophenyl)-2,2,2-trifluoro-N,N-dimethylethanamine | LRMS (ESI) calc'd for $C_{10}H_{12}BrF_3N$ $[M + H]^+$: 282, found 282. |

TABLE 4-continued

| Intermediate | Structure | Name | LCMS |
|---|---|---|---|
| I-21-11 | 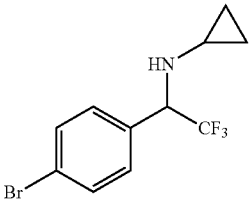 [SMILES: FC(F)(F)C(NC1CC1)c1ccc(Br)cc1] | N-(1-(4-bromophenyl)-2,2,2-trifluoroethyl)cyclopropanamine | LRMS (ESI) calc'd for $C_{11}H_{12}BrF_3N$ $[M + H]^+$: 294, 296 (1:1), found 294, 296 (1:1). |
| I-21-12 | 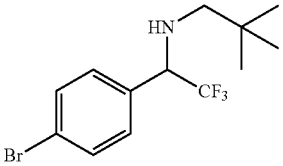 | N-(1-(4-bromophenyl)-2,2,2-trifluoroethyl)-2,2-dimethylpropan-1-amine | LRMS (ESI) calc'd for $C_{13}H_{18}BrF_3N$ $[M + H]^+$: 324, 326 (1:1), found 324, 326 (1:1). |
| I-21-13 | 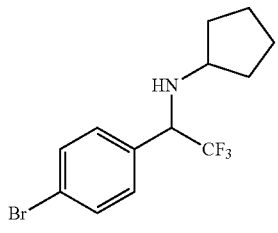 [SMILES: FC(F)(F)C(NC1CCCC1)c1ccc(Br)cc1] | N-(1-(4-bromophenyl)-2,2,2-trifluoroethyl)cyclopentanamine | LRMS (ESI) calc'd for $C_{13}H_{16}BrF_3N$ $[M + H]^+$: 322, 324 (1:1), found 322, 324 (1:1). |
| I-21-14 | 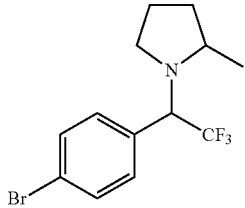 [SMILES: CC1CCCN1C(c1ccc(Br)cc1)C(F)(F)F] | 1-(1-(4-bromophenyl)-2,2,2-trifluoroethyl)-2-methylpyrrolidine | LRMS (ESI) calc'd for $C_{13}H_{16}BrF_3N$ $[M + H]^+$: 322, 324 (1:1), found 322, 324 (1:1). |
| I-21-15 | 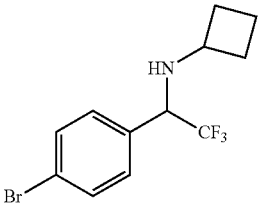 [SMILES: FC(F)(F)C(NC1CCC1)c1ccc(Br)cc1] | N-(1-(4-bromophenyl)-2,2,2-trifluoroethyl)cyclobutanamine | LRMS (ESI) calc'd for $C_{12}H_{16}BrF_3N$ $[M + H]^+$: 310, 312 (1:1), found 310, 312 (1:1). |
| I-21-16 | 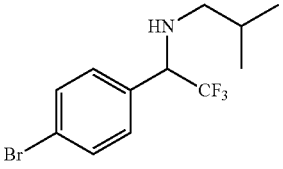 | N-(1-(4-bromophenyl)-2,2,2-trifluoroethyl)-2-methylpropan-1-amine | LRMS (ESI) calc'd for $C_{12}H_{14}BrF_3N$ $[M + H]^+$: 308, 310 (1:1), found 308, 310 (1:1). |
| I-21-17 | 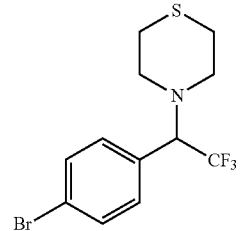 [SMILES: FC(F)(F)C(c1ccc(Br)cc1)N1CCSCC1] | 4-(1-(4-bromophenyl)-2,2,2-trifluoroethyl)thiomorpholine (Peak A from HPLC Chiralcel OJ-3, 5% EtOH in hexanes, Tr = 3.8 minutes) | LRMS (ESI) calc'd for $C_{12}H_{14}BrF_3NS$ $[M + H]^+$: 342, 340 (1:1), found 342, 340 (1:1). |

TABLE 4-continued

| Intermediate | Structure | Name | LCMS |
|---|---|---|---|
| I-21-18 | 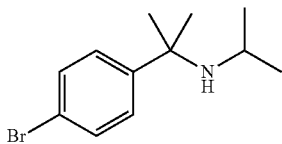 | 4-(1-(4-bromophenyl)-2,2,2-trifluoroethyl)thiomorpholine (Peak B from HPLC Chiralcel OJ-3, 5% EtOH in hexanes, Tr = 6.3 minutes) | LRMS (ESI) calc'd for $C_{12}H_{14}BrF_3NS$ [M + H]$^+$: 342, 340 (1:1), found 342, 340 (1:1). |

Intermediate I-22

2-(4-bromophenyl)-N-isopropylpropan-2-amine

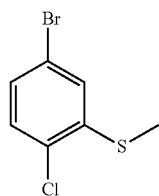

I-22

2-(4-Bromophenyl)propan-2-amine (0.5 g, 2.3 mmol) was dissolved in DCM (20 mL) and acetone (2.5 mL), and sodium triacetoxyborohydride (1.5 g, 7.0 mmol) was then added portionwise. The cloudy reaction mixture was stirred at room temperature for 48 hours. The reaction mixture was then diluted with ethyl acetate and washed with saturated sodium bicarbonate and brine. The combined organic layers were dried over $Na_2SO_4$, filtered, and the filtrate was concentrated in vacuo. The residue was purified by silica chromatography, eluting with 5-40% EtOAc in hexanes to afford I-22 as a liquid. LRMS (ESI) calc'd for $C_{12}H_{19}BrN$ [M+H]$^+$: 256, found 256.

Intermediate 23

(5-bromo-2-chlorophenyl)(methyl)sulfane

I-23-1

5-Bromo-2-chlorobenzenethiol (0.40 g, 1.8 mmol) was stirred in anhydrous THF (9.0 mL) and sodium hydride (0.11 g, 2.7 mmol, 60 wt. % in mineral oil) was added in one portion. The resulting mixture was stirred at ambient temperature for 10 minutes before iodomethane (0.25 g, 1.8 mmol) was added. The mixture was stirred for 16 hours, diluted with water, and extracted with EtOAc. The organic layer was washed with saturated aqueous sodium bicarbonate, brine, dried over anhydrous magnesium sulfate, filtered, and then concentrated in vacuo to afford I-23-1. $^1$H NMR (500 MHz, CDCl$_3$): δ 7.22 (s, 1H), 7.19 (m, 2H), 2.48 (s, 3H).

Following an analogous method to that outlined for I-23-1 above, the following intermediates in Table 5 were prepared:

TABLE 5

| Intermediate | Structure | Name | NMR |
|---|---|---|---|
| I-23-2 | 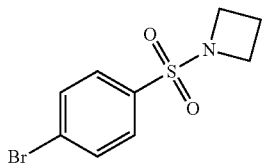 | (5-bromo-2-fluorophenyl)(methyl)sulfane | $^1$H NMR (500 MHz, CDCl$_3$): δ 7.31 (dd, J = 6.7, 2.4 Hz, 1H); 7.24 (ddd, J = 8.6, 4.4, 2.4 Hz, 1H); 6.91 (t, J = 9.0 Hz, 1H); 2.47 (s, 3H). |

Intermediate 24

1-((4-bromophenyl)sulfonyl)azetidine

I-24-1

To the solution of 4-bromobenzene-1-sulfonyl chloride (507 mg, 1.98 mmol) in DCM (6.0 mL), was added azetidine (280 mg, 4.90 mmol) and the reaction mixture was stirred at room temperature under nitrogen overnight. The reaction was then quenched by addition of saturated aqueous NH$_4$Cl and the reaction mixture was extracted with DCM (×3). The organic layers were washed with water, dried over sodium sulfate, filtered and concentrated in vacuo. The residue was purified by silica chromatography, eluting with 0-60% EtOAc in hexanes to afford I-24-1 as a solid. LRMS (ESI) calc'd for $C_9H_{11}BrNO_2S$ [M+H]$^+$: 278, found 278. $^1$H NMR (600 MHz, CDCl$_3$): δ 7.73 (d, 2H, J=8.6 Hz), 7.70 (d, 2H, J=8.6 Hz), 3.79 (t, 4H, J=7.4 Hz), 2.11 (pentet, 2H, J=7.9 Hz).

Following an analogous method to that outlined for I-24-1 above, the following intermediates in Table 6 were prepared. In certain instances the general procedure was modified by adding DIPEA or TEA to the reaction.

TABLE 6

| Intermediate | Structure | Name | LRMS or NMR |
|---|---|---|---|
| I-24-2A | 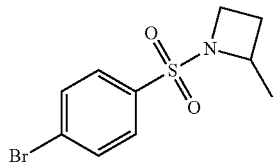 | (R or S)-1-((4-bromophenyl)sulfonyl)-2-methylazetidine (Derived from racemic material, SFC peak 1, CHIRALPAK ®, AD-H, 10% MeOH in $CO_2$, Tr = 3.9 minutes) | LRMS (ESI) calc'd for $C_{11}H_{13}BrNO_2S$ [M + H]$^+$: 292, found 292. |
| I-24-2B | 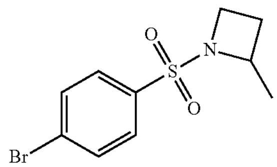 | (R or S)-1-((4-bromophenyl)sulfonyl)-2-methylazetidine (Derived from racemic material, SFC peak 2, CHIRALPAK ®, AD-H, 10% MeOH in $CO_2$, Tr = 4.5 minutes) | LRMS (ESI) calc'd for $C_{11}H_{13}BrNO_2S$ [M + H]$^+$: 292, found 292. |
| I-24-3A | 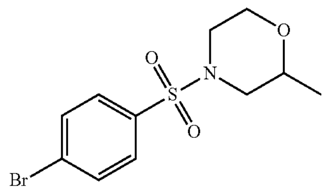 [SMILES: CC1CN(S(=O)(=O)c2ccc(Br)cc2)CCO1] | (R or S)-4-((4-bromophenyl)sulfonyl)-2-methylmorpholine (Derived from racemic material, SFC peak 1, CHIRALPAK ®, AD-H, 20% MeOH in $CO_2$, Tr = 3.2 minutes) | LRMS (ESI) calc'd for $C_{11}H_{15}BrNO_3S$ [M + H]$^+$: 322, found 322. |
| I-24-3B | 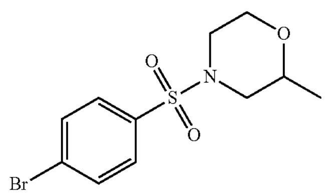 [SMILES: CC1CN(S(=O)(=O)c2ccc(Br)cc2)CCO1] | (R or S)-4-((4-bromophenyl)sulfonyl)-2-methylmorpholine (Derived from racemic material, SFC peak 2, CHIRALPAK ®, AD-H, 20% MeOH in $CO_2$, Tr = 3.9 minutes) | LRMS (ESI) calc'd for $C_{11}H_{15}BrNO_3S$ [M + H]$^+$: 322, found 322. |
| I-24-4 | 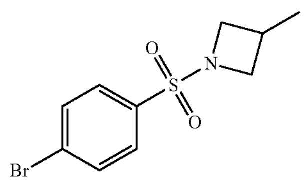 | 1-((4-bromophenyl)sulfonyl)-3-methylazetidine | LRMS (ESI) calc'd for $C_{10}H_{13}BrNO_2S$ [M + H]$^+$: 292, found 292. |
| I-24-5 | 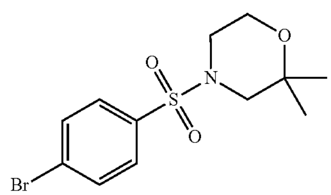 [SMILES: CC1(C)CN(S(=O)(=O)c2ccc(Br)cc2)CCO1] | 4-((4-bromophenyl)sulfonyl)-2,2-dimethylmorpholine | LRMS (ESI) calc'd for $C_{12}H_{17}BrNO_3S$ [M + H]$^+$: 336, found 336. |
| I-24-6 | 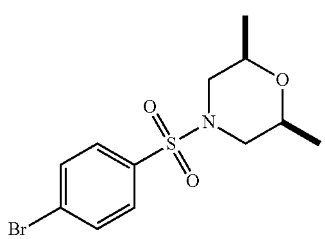 [SMILES: C[C@@H]1CN(S(=O)(=O)c2ccc(Br)cc2)C[C@H](C)O1] | (cis)-4-((4-bromophenyl)sulfonyl)-2,6-dimethylmorpholine | LRMS (ESI) calc'd for $C_{12}H_{17}BrNO_3S$ [M + H]$^+$: 336, found 336. |
| I-24-7 | 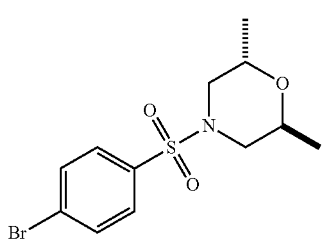 [SMILES: C[C@H]1CN(S(=O)(=O)c2ccc(Br)cc2)C[C@H](C)O1] | (trans)-4-((4-bromophenyl)sulfonyl)-2,6-dimethylmorpholine | LRMS (ESI) calc'd for $C_{12}H_{17}BrNO_3S$ [M + H]$^+$: 336, found 336. |

TABLE 6-continued

| Intermediate | Structure | Name | LRMS or NMR |
|---|---|---|---|
| I-24-8 | 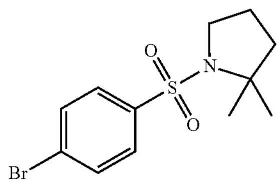 [SMILES: CC1(C)CCCN1S(=O)(=O)c1ccc(Br)cc1] | 1-((4-bromophenyl)sulfonyl-2,2-dimethylpyrrolidine | LRMS (ESI) calc'd for $C_{12}H_{17}BrNO_2S$ [M + H]$^+$: 320, found 320. |
| I-24-9 | 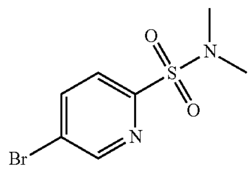 | 5-bromo-N,N-dimethylpyridine-2-sulfonamide | LRMS (ESI) calc'd for $C_7H_{10}BrN_2O_2S$ [M + H]$^+$: 267, found 267. |
| I-24-10 | 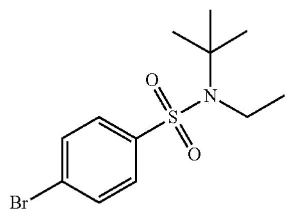 [SMILES: CCN(C(C)(C)C)S(=O)(=O)c1ccc(Br)cc1] | 4-bromo-N-(tert-butyl)-N-ethylbenzene-sulfonamide | $^1$H NMR (600 MHz, CDCl$_3$): δ 7.69 (d, J = 8.6 Hz, 2H), 7.60 (d, J = 8.60 Hz, 2H), 3.48 (q, 2H, J = 7.0 Hz), 1.34 (t, 3H, J = 7.2 Hz), 1.33 (s, 9H). |

Intermediate I-25

2-(1-(4-bromophenyl)ethyl)-2H-1,2,3-triazole

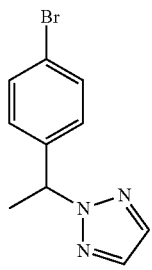

I-25

Step 1: 1-bromo-4-(1-bromoethyl)benzene (I-25a)

To a solution of 1-bromo-4-ethylbenzene (5.10 g, 27.6 mmol), in chloroform (100 mL), was added N-bromosuccinimide (5.77 g, 32.4 mmol) and azo-bis-isobutyronitrile (0.89 g, 5.4 mmol). The mixture was refluxed for 3 hours, cooled to ambient temperature, and water (100 mL) was added. The organic layer was washed with brine, dried over anhydrous sodium sulfate, filtered, and concentrated in vacuo. The residue was purified by silica chromatography, eluting with 1:20 ethyl acetate:hexanes to afford I-25a. $^1$H NMR (300 MHz, CDCl$_3$) δ 7.44 (d, J=8.4 Hz, 2H), 7.31 (d, J=8.4 Hz, 2H), 5.15 (q, J=6.9 Hz, 1H), 2.01 (d, J=6.9 Hz, 3H).

Step 2: 2-(1-(4-bromophenyl)ethyl)-2H-1,2,3-triazole (I-25)

To a solution of 1-bromo-4-(1-bromoethyl)benzene (4.60 g, 17.5 mmol) in N,N-dimethylformamide (60 mL), was added 1H-1,2,3-triazole (1.5 g, 21 mmol) and potassium carbonate (6.04 g, 43.8 mmol). The solution was stirred for 5 hours at 80° C. and then quenched by pouring into water (100 mL). The resulting mixture was extracted with ethyl acetate (×3) and the combined organic layers were dried over anhydrous sodium sulfate, filtered, and concentrated in vacuo. The resulting solid was triturated with ethyl acetate/petroleum ether (1/3, 10 mL) and filtered to afford I-25 and as a mixture of N1 and N2 isomers that could be separated after the cross coupling step. LCMS (ESI) calc'd for desired N2 isomer $C_{10}H_{10}BrN_3$ [M+H]$^+$: 252, 254 (1:1), found 252, 254 (1:1); $^1$H NMR (300 MHz, CDCl$_3$) δ 7.62 (s, 2H), 7.44 (d, J=8.4 Hz, 2H), 7.16 (d, J=8.4 Hz, 2H), 5.82 (q, J=7.2 Hz, 1H), 1.96 (d, J=7.2 Hz, 3H).

Intermediates I-26 and I-27

(R or S)-2-(4-bromophenyl)-2-(trifluoromethyl)piperidine and (R or S)-2-(4-bromophenyl)-2-(trifluoromethyl)piperidine

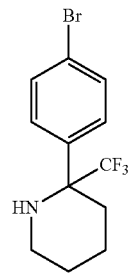

I-26

65
-continued

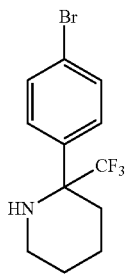

I-27

Step 1: 4-bromobenzoyl chloride

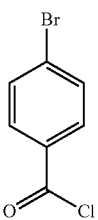

I-26a

A solution of 4-bromobenzoic acid (10.0 g, 49.7 mmol) in sulfurous dichloride (59.2 g, 0.50 mol) was heated at 80° C. for 16 hours. The mixture was then concentrated in vacuo to afford the title compound which was carried onto the next step without further purification.

Step 2: tert-butyl 3-(4-bromobenzoyl)-2-oxopiperidine-1-carboxylate

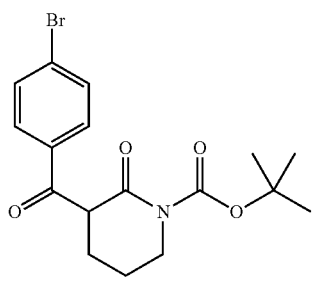

I-26b

Lithium bis(trimethylsilyl)amide (2.11 mL, 2.11 mmol, 1.0 M in THF) was added to a solution of tert-butyl 2-oxopiperidine-1-carboxylate (0.20 g, 1.0 mmol) in THF (2 mL) at −78° C. The resulting mixture was stirred for 10 minutes, then 4-bromobenzoyl chloride (0.22 g, 1.0 mmol) was added. The reaction was warmed to ambient temperature and stirred for 1 hour, then saturated aqueous ammonium chloride (20 mL) was added. The quenched reaction was extracted with EtOAc (×3) and the combined organic layers were dried over anhydrous Na₂SO₄, filtered and concentrated in vacuo. The residue was purified on silica, eluting with 0-1% EtOAc in hexanes to afford the title compound. LRMS (ESI) calc'd for: $C_{17}H_{21}BrNO_4[M+H]^+$: 382, 384 (1:1), found 382, 384 (1:1).

66

Step 3: 6-(4-bromophenyl)-2,3,4,5-tetrahydropyridine

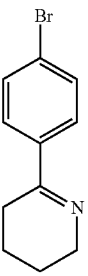

I-26c tert-Butyl 3-(4-bromobenzoyl)-2-oxopiperidine-1-carboxylate (2.00 g, 5.23 mmol) was combined with HCl (8.0 M, 43.6 mL, 0.52 mol) at ambient temperature. The resulting solution was heated at 80° C. for 16 hours. The reaction was then poured into saturated aqueous Na₂CO₃ (50 mL) and extracted with EtOAc (×3). The combined organic layers were dried over Na₂SO₄, filtered and concentrated in vacuo. The residue was purified on silica, eluting with 0-1% EtOAc in hexanes to afford the title compound. LRMS (ESI) calc'd for: $C_{11}H_{13}BrN [M+H]^+$: 238, 240 (1:1), found 238, 240 (1:1); ¹H NMR (300 MHz, CDCl₃) δ 7.66-7.63 (m, 2H), 7.52-7.47 (m, 2H), 3.90 (m, 2H), 2.59 (m, 2H), 1.88-1.79 (m, 2H), 1.78-1.66 (m, 2H).

Step 4: (R or S)-2-(4-bromophenyl)-2-(trifluoromethyl)piperidine and (R or S)-2-(4-bromophenyl)-2-(trifluoromethyl)piperidine To a solution of 6-(4-bromophenyl)-2,3,4,5-tetrahydropyridine (1.0 g, 4.2 mmol) in acetonitrile (10 mL), was successively added trifluoromethanesulfonic acid (3.30 g, 22.0 mmol), potassium hydrogen fluoride (3.94 g, 50.4 mmol) and trimethyl(trifluoromethyl)silane (5.97 g, 42.0 mmol) at 0-4° C. The resulted mixture was stirred at ambient temperature for 48 hours. The reaction was then quenched with saturated aqueous NaHCO₃ (50 mL) followed by extraction with EtOAc (×3). The combined organic layers were dried over anhydrous Na₂SO₄, filtered and concentrated in vacuo. The residue was purified on silica, eluting with 0-1% DCM in petroleum ether to afford the racemic title compound. The title compounds were then separated by SFC using a Chiralpak IA column, eluting with 15% i-PrOH in CO₂ to afford Peak A (I-26) (Tr=4.7 minutes) and Peak B (I-27) (Tr=5.5 minutes). LRMS (ESI) calc'd for $C_{12}H_{14}BrF_3N [M+H]^+$: 308, 310 (1:1), found 308, 310 (1:1); ¹H NMR (300 MHz, CDCl₃) δ 7.66 (m, 2H), 7.59 (m, 2H), 3.16-3.03 (m, 1H), 2.73-2.63 (m, 1H), 2.50-2.42 (m, 1H), 2.25-1.93 (m, 1H), 1.75 (m, 1H), 1.67-1.53 (m, 3H), 1.33 (m, 1H).

Intermediate I-28

(R or S)-1-benzyl-3-(4-bromophenyl)-3-(trifluoromethyl)pyrrolidine

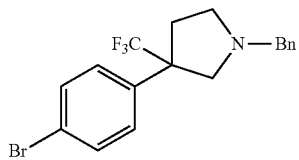

I-28

Step 1:
1-bromo-4-(3,3,3-trifluoroprop-1-en-2-yl)benzene

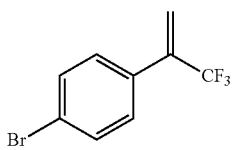

I-28a

To an oven dried round bottom flask under nitrogen, was added methyltriphenylphosphonium bromide (6.35 g, 17.8 mmol) and THF (13.2 mL). The mixture was cooled to 0° C., and then lithium bis(trimethylsilyamide (17.8 mL, 17.8 mmol, 1M in THF) was added. The reaction mixture was stirred for 30 minutes at 0° C., cooled to −78° C., and 1-(4-bromophenyl)-2,2,2-trifluoroethanone (3.00 g, 11.9 mmol) was added. The reaction mixture was allowed to warm to room temperature over 1 hour and then quenched by pouring into a 1:1 ice water/saturated aqueous NH$_4$Cl solution, and the aqeuous layer was extracted with EtOAc (×3). The combined organic layers were washed with brine, dried over Na$_2$SO$_4$, filtered and concentrated in vacuo to afford the desired compound. $^1$H NMR (600 MHz, CDCl$_3$): δ $^1$H NMR δ 7.50 (d, J=8.3 Hz, 2H), 7.30 (d, J=8.2 Hz, 2H), 5.96 (s, 1H), 5.75 (s, 1H).

Step 2: 1-benzyl-3-(4-bromophenyl)-3-(trifluoromethyl)pyrrolidine

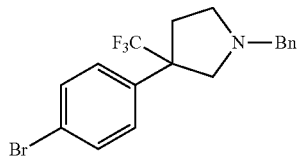

I-28b

To an oven dried round bottom flask under nitrogen, was added 1-bromo-4-(3,3,3-trifluoroprop-1-en-2-yl)benzene (0.25 g, 1.0 mmol), N-benzyl-1-methoxy-N-((trimethylsilyl)methyl)methanamine (0.51 mL, 2.0 mmol), and DCM (5 mL). The mixture was cooled to 0° C., and then trifluoroacetic acid (7.7 μL, 0.10 mmol) was added. The reaction mixture was stirred and warmed to room temperature over 3 hours and quenched with saturated aqueous NaHCO$_3$ (20 mL). The aqueous layer was extracted with EtOAc (×3) and the combined organic layers were washed with brine, dried over Na$_2$SO$_4$, filtered and concentrated in vacuo to afford the desired compound. $^1$H NMR (600 MHz, CDCl$_3$): δ 7.45 (d, J=8.2 Hz, 2H), 7.29-7.35, (m, 4H), 7.21 (m, 3H), 3.66 (m, 2H), 3.18 (m, 1H), 2.77 (m, 1H), 2.58 (m, 1H), 2.37 (m, 1H), 1.25 (m, 1H), 0.85 (m, 1H).

Intermediate I-29-1

1-(4-bromophenyl)-2,2,2-trifluoro-1-(pyridin-2-yl)ethanol

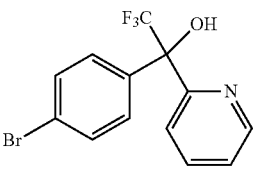

I-29-1

An oven dried round bottom flask under nitrogen was charged with (4-bromophenyl)(pyridin-2-yl)methanone (1.00 g, 3.82 mmol) and THF (5.2 mL). The solution was cooled to 0° C., and (trifluoromethyl)trimethylsilane (2.82 mL, 19.1 mmol) was added followed by the slow dropwise (exotherm) addition of tetrabutylammonium fluoride (4.8 mL, 4.8 mmol, 1M in THF). The reaction mixture was stirred and warmed to room temperature overnight. The reaction was quenched with saturated aqueous NaHCO$_3$, diluted with EtOAc, and the layers were separated and the aqueous layer was extracted with EtOAc (×3). The combined organic layers were washed with brine, dried over Na$_2$SO$_4$, and concentrated in vacuo. The resulting oil was purified by silica chromatography, eluting with 5-50% EtOAc/hexanes to give the title compound. $^1$H NMR (CDCl$_3$, 500 MHz): δ 8.59 (d, J=4.9 Hz, 1H), 7.75 (td, J=7.8, 1.7 Hz, 1H), 7.52-7.44 (m, 5H), 7.36 (m, 1H), 7.00 (br s, 1H).

Following analogous methodology to that outlined for Intermediate I-29-1 above, the following intermediates in Table 7 were synthesized.

TABLE 7

| | | |
|---|---|---|
| I-29-2 | ![structure] | 1-(4-bromophenyl)-2,2,2-trifluoro-1-(pyridin-4-yl)ethanol    $^1$H NMR (CDCl$_3$, 500 MHz): δ 8.45 (br s, 1H), 7.53-7.38 (m, 6H), 7.36-7.31 (m, 2H). |

Intermediate I-30

6-bromo-3-(isopropylamino)-3-methylindolin-2-one

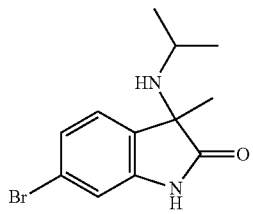

I-30

A solution of 6-bromoindole-2,3-dione (1.00 g, 4.42 mmol) and propan-2-amine (0.392 g, 6.64 mmol) in EtOH (5 mL) were heated at 130° C. for 1 hour in a microwave. The reaction was concentrated in vacuo, and excess EtOH was azeotroped with toluene followed by the imine intermediate being triturated from diethyl ether to afford a solid. The imine intermediate was taken up in diethyl ether (15 mL) at 0° C., and BF$_3$.OEt$_2$ (0.68 mL, 5.4 mmol) was added and the reaction was stirred for 15 minutes. MeMgBr (1.8 mL, 5.4 mmol, 3M in THF) was then added and the reaction was gradually warmed to ambient temperature. The reaction was quenched with aqueous saturated NH$_4$Cl, diluted with EtOAc and aqueous saturated NaHCO$_3$, and the organics were separated, washed with brine, dried over Na$_2$SO$_4$, filtered and concentrated in vacuo. Purification by silica chromatography, eluting with 0-50% EtOAc in hexanes followed by 0-20% MeOH in DCM afforded the title compound as a solid. LRMS (ESI) calc'd for C$_{12}$H$_{16}$BrN$_2$O [M+H]$^+$: 283, 285 (1:1), found 283, 285 (1:1); $^1$H NMR (500 MHz DMSO-d6): δ 10.42 (s, 1H), 7.20 (m, (2H), 6.91 (s, 1H), 2.39 (m, 1H), 1.20 (s, 3H), 1.0 (d, 1H), 0.65 (d, 6H).

Example 1-1

(3S,4R)-3-(3-((4-(methylsulfonyl)phenyl)amino)-4-oxo-4,5-dihydro-1H-pyrazolo[4,3-c]pyridin-1-yl)tetrahydro-2H-pyran-4-carbonitrile

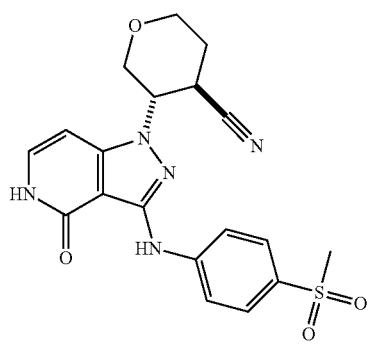

1-1

Step 1: (3S,4R)-3-(4-(benzyloxy)-3-((4-(methylsulfonyl)phenyl)amino)-1H-pyrazolo[4,3-c]pyridin-1-yl)tetrahydro-2H-pyran-4-carbonitrile

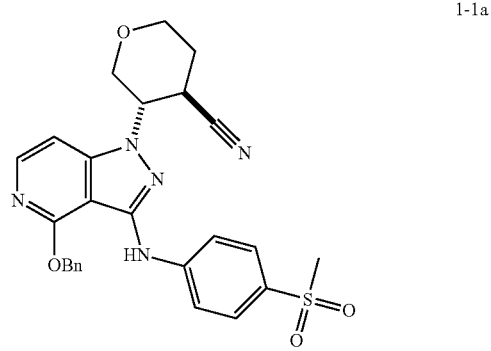

1-1a

To (3S,4R)-3-(3-amino-4-(benzyloxy)-1H-pyrazolo[4,3-c]pyridin-1-yl)tetrahydro-2H-pyran-4-carbonitrile (Intermediate 3A) (40.0 mg, 0.114 mmol), 1-bromo-4-(methylsulfonyl)benzene (53.8 mg, 0.229 mmol), Pd$_2$dba$_3$ (26 mg, 0.029 mmol), potassium phosphate tribasic (48.6 mg, 0.229 mmol), 2-di-tert-butylphosphino-3,4,5,6-tetramethyl-2',4',6'-triisopropyl-1,1'-biphenyl (41 mg, 0.086 mmol) in a degassed sealed microwave vial, was added t-amyl alcohol (1.53 mL) and the reaction was heated to 75° C. for 18 hours. The reaction was then concentrated in vacuo and purified by silica chromatography, eluting with 5-60% EtOAc in hexanes to afford the desired product, 1-1a, as a solid. LRMS (ESI) calc'd for C$_{26}$H$_{26}$N$_5$O$_4$S [M+H]$^+$: 504, found 504.

Step 2: (3S,4R)-3-(3-((4-(methylsulfonyl)phenyl)amino)-4-oxo-4,5-dihydro-1H-pyrazolo[4,3-c]pyridin-1-yl)tetrahydro-2H-pyran-4-carbonitrile To 1-1a (71 mg, 0.14 mmol) and Pd/C (15 mg, 10 wt. % Pd) was added ethyl acetate (0.71 mL) and the reaction was evacuated and backfilled with hydrogen gas (1 atmosphere). The reaction was then stirred at 25° C. overnight, filtered through CELITE®, and concentrated in vacuo and purified by silica chromatography, eluting with 1-6% methanol in DCM to afford a solid, 1-1. LRMS (ESI) calc'd for C$_{19}$H$_{20}$N$_5$O$_4$S [M+H]$^+$: 414, found 414. $^1$H NMR (600 MHz, DMSO-d6): δ 11.23 (s, 1H), 8.71 (s, 1H), 7.89 (d, J=8.8 Hz, 2H), 7.79 (d, J=8.8 Hz, 2H), 7.29 (m, 1H), 6.78 (d, J=7.4 Hz, 1H), 4.92 (dt, J=10.7, 4.6 Hz, 1H), 4.00 (dd, J=11.4, 4.7 Hz, 1H), 3.96 (dd, J=7.7, 4.0 Hz, 1H), 3.75 (dt, J=11.4, 3.7 Hz, 1H), 3.70 (t, J=10.8 Hz, 1H), 3.50 (t, J=11.8 Hz, 1H), 3.14 (s, 3H), 2.20 (d, J=12.1 Hz, 1H), 2.05 (app. dq, J=12.6, 4.5 Hz, 1H).

The following examples outlined in Table 8 were prepared by analogy using the general procedure outlined above for Example 1-1. In select cases, the general procedure was modified to alternatively utilize KOAc base, 2-di-tert-butylphosphino-2',4',6'-triisopropyl-1,1'-biphenyl ligand instead, [(2-di-tert-butylphosphino-2',4',6'-triisopropyl-1,1'-biphenyl)-2-(2'-amino-1,1'-biphenyl)]palladium(II) methanesulfonate (t-BuXPhos Pd G3) precatalyst in place of the individual phosphine and palladium source, and t-amyl alcohol or DMF in place of 2-propanol. Additionally, in certain instances the cross coupling could be run between 70-90° C. In select cases the hydrogenolysis reaction was alternatively conducted in MeOH or THF or using a suitable cosolvent with any of the above solvents to facilitate dissolution of the starting material.

TABLE 8

| Example | Structure | Compound Name | LRMS |
|---|---|---|---|
| 1-2 | 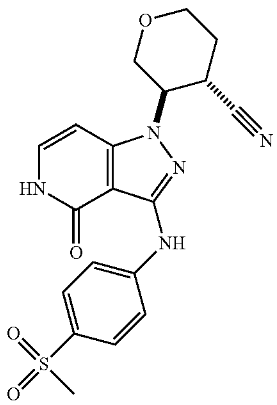 [SMILES: CS(=O)(=O)c1ccc(Nc2nn([C@H]3COCC[C@@H]3C#N)c3cc[nH]c(=O)c23)cc1] | (3R,4S)-3-(3-((4-(methylsulfonyl)phenyl)amino)-4-oxo-4,5-dihydro-1H-pyrazolo[4,3-c]pyridin-1-yl)tetrahydro-2H-pyran-4-carbonitrile | LRMS (ESI) calc'd for $C_{19}H_{20}N_5O_4S$ [M + H]$^+$: 414, found 414. |
| 1-3 | 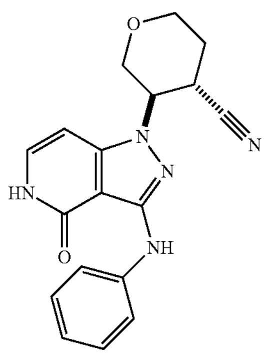 [SMILES: N#C[C@H]1CCOC[C@@H]1n1nc(Nc2ccccc2)c2c(=O)[nH]ccc21] | (3R,4S)-3-(4-oxo-3-(phenylamino)-4,5-dihydro-1H-pyrazolo[4,3-c]pyridin-1-yl)tetrahydro-2H-pyran-4-carbonitrile | LRMS (ESI) calc'd for $C_{18}H_{18}N_5O_2$ [M + H]$^+$: 336, found 336. |
| 1-4 | 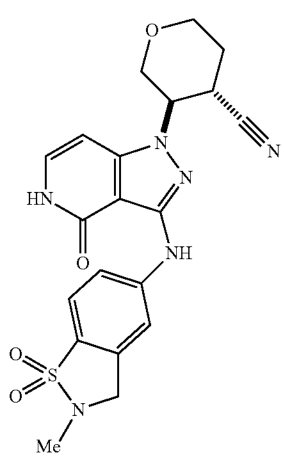 [SMILES: CN1Cc2cc(Nc3nn([C@H]4COCC[C@@H]4C#N)c4cc[nH]c(=O)c34)ccc2S1(=O)=O] | (3R,4S)-3-(3-((2-methyl-1,1-dioxido-2,3-dihydrobenzo[d]isothiazol-5-yl)amino)-4-oxo-4,5-dihydro-1H-pyrazolo[4,3-c]pyridin-1-yl)tetrahydro-2H-pyran-4-carbonitrile | LRMS (ESI) calc'd for $C_{20}H_{21}N_6O_4S$ [M + H]$^+$: 441, found 441. |

TABLE 8-continued

| Example | Structure | Compound Name | LRMS |
|---|---|---|---|
| 1-5 | 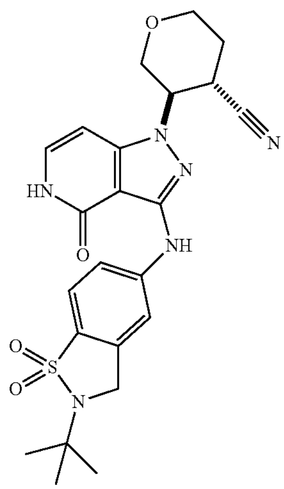 [SMILES: CC(C)(C)N1Cc2cc(Nc3nn([C@H]4COCC[C@@H]4C#N)c4cc[nH]c(=O)c34)ccc2S1(=O)=O] | (3R,4S)-3-(3-((2-(tert-butyl)-1,1-dioxido-2,3-dihydrobenzo[d]isothiazol-5-yl)amino)-4-oxo-4,5-dihydro-1H-pyrazolo[4,3-c]pyridin-1-yl)tetrahydro-2H-pyran-4-carbonitrile | LRMS (ESI) calc'd for $C_{23}H_{27}N_6O_4S$ $[M + H]^+$: 483, found 483. |
| 1-6 | 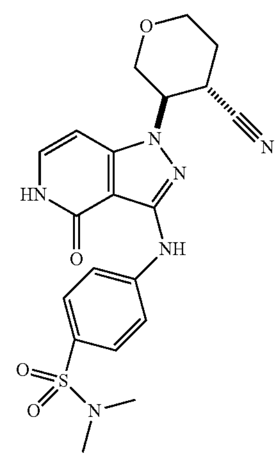 [SMILES: CN(C)S(=O)(=O)c1ccc(Nc2nn([C@H]3COCC[C@@H]3C#N)c3cc[nH]c(=O)c23)cc1] | 4-((1-((3R,4S)-4-cyanotetrahydro-2H-pyran-3-yl)-4-oxo-4,5-dihydro-1H-pyrazolo[4,3-c]pyridin-3-yl)amino)-N,N-dimethyl-benzenesulfonamide | LRMS (ESI) calc'd for $C_{20}H_{23}N_6O_4S$ $[M + H]^+$: 443, found 443. |
| 1-7 | 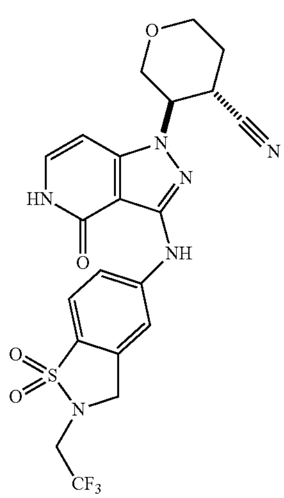 [SMILES: N#C[C@H]1CCOC[C@@H]1n1nc(Nc2ccc3c(c2)CN(CC(F)(F)F)S3(=O)=O)c2c(=O)[nH]ccc21] | (3R,4S)-3-(3-((1,1-dioxido-2-(2,2,2-trifluoroethyl)-2,3-dihydrobenzo[d]isothiazol-5-yl)amino)-4-oxo-4,5-dihydro-1H-pyrazolo[4,3-c]pyridin-1-yl)tetrahydro-2H-pyran-4-carbonitrile | LRMS (ESI) calc'd for $C_{21}H_{20}N_6O_4SF_3$ $[M + H]^+$: 509, found 509. |

TABLE 8-continued

| Example | Structure | Compound Name | LRMS |
|---|---|---|---|
| 1-8 | 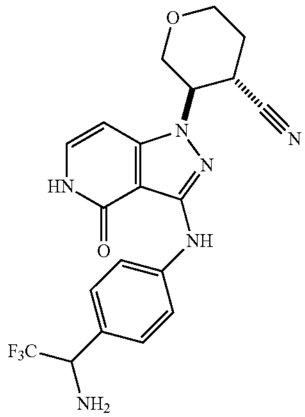 [SMILES: N#C[C@H]1CCOC[C@@H]1n1nc(Nc2ccc(C(N)C(F)(F)F)cc2)c2c(=O)[nH]ccc21] | (3R,4S)-3-(3-((4-((R or S)-1-amino-2,2-trifluoroethyl)phenyl)amino)-4-oxo-4,5-dihydro-1H-pyrazolo[4,3-c]pyridin-1-yl)tetrahydro-2H-pyran-4-carbonitrile (from I-11A) | LRMS (ESI) calc'd for $C_{20}H_{20}N_6O_2F_3$ [M + H]$^+$: 433, found 433. |
| 1-9 | 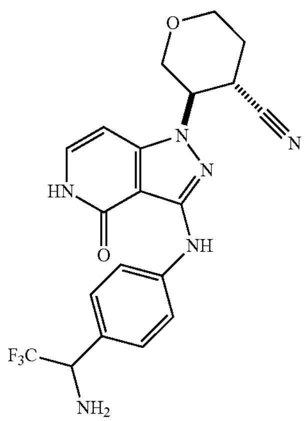 [SMILES: N#C[C@H]1CCOC[C@@H]1n1nc(Nc2ccc(C(N)C(F)(F)F)cc2)c2c(=O)[nH]ccc21] | (3R,4S)-3-(3-((4-((S or R)-1-amino-2,2-trifluoroethyl)phenyl)amino)-4-oxo-4,5-dihydro-1H-pyrazolo[4,3-c]pyridin-1-yl)tetrahydro-2H-pyran-4-carbonitrile (from I-11B) | LRMS (ESI) calc'd for $C_{20}H_{20}N_6O_2F_3$ [M + H]$^+$: 433, found 433. |
| 1-10 | 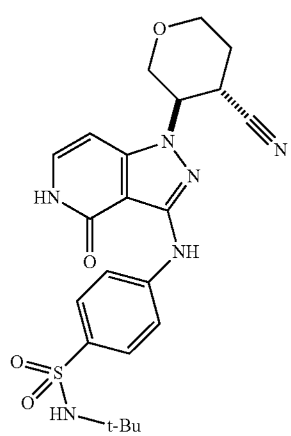 [SMILES: CC(C)(C)NS(=O)(=O)c1ccc(Nc2nn([C@H]3COCC[C@@H]3C#N)c3cc[nH]c(=O)c23)cc1] | N-(tert-butyl)-4-((1-((3R,4S)-4-cyanotetrahydro-2H-pyran-3-yl)-4-oxo-4,5-dihydro-1H-pyrazolo[4,3-c]pyridin-3-yl)amino)benzenesulfonamide | LRMS (ESI) calc'd for $C_{22}H_{27}N_6O_4S$ [M + H]$^+$: 471, found 471. |

TABLE 8-continued

| Example | Structure | Compound Name | LRMS |
|---|---|---|---|
| 1-11 | 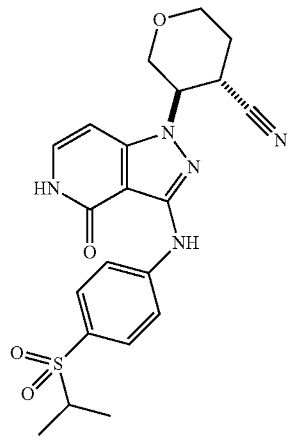 [SMILES: CC(C)S(=O)(=O)c1ccc(Nc2nn([C@H]3COCC[C@@H]3C#N)c3cc[nH]c(=O)c23)cc1] | (3R,4S)-3-(3-((4-(isopropylsulfonyl)phenyl)amino)-4-oxo-4,5-dihydro-1H-pyrazolo[4,3-c]pyridin-1-yl)tetrahydro-2H-pyran-4-carbonitrile | LRMS (ESI) calc'd for $C_{21}H_{24}N_5O_4S$ [M + H]$^+$: 442, found 442. |
| 1-12 | 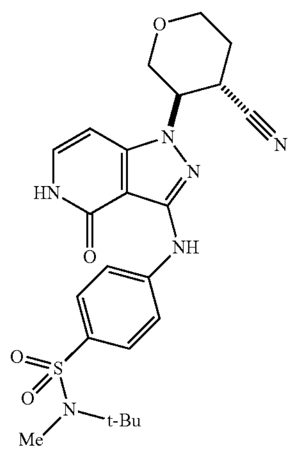 [SMILES: CN(C(C)(C)C)S(=O)(=O)c1ccc(Nc2nn([C@H]3COCC[C@@H]3C#N)c3cc[nH]c(=O)c23)cc1] | N-(tert-butyl)-4-((1-((3R,4S)-4-cyanotetrahydro-2H-pyran-3-yl)-4-oxo-4,5-dihydro-1H-pyrazolo[4,3-c]pyridin-3-yl)amino)-N-methylbenzenesulfonamide | LRMS (ESI) calc'd for $C_{23}H_{29}N_6O_4S$ [M + H]$^+$: 485, found 485. |
| 1-13 | 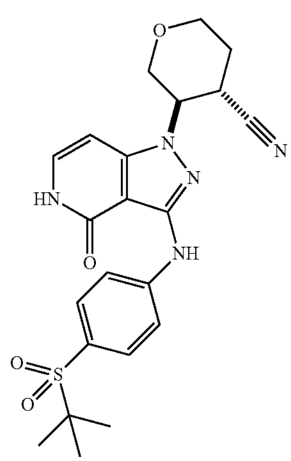 [SMILES: CC(C)(C)S(=O)(=O)c1ccc(Nc2nn([C@H]3COCC[C@@H]3C#N)c3cc[nH]c(=O)c23)cc1] | (3R,4S)-3-(3-((4-tert-butylsulfonyl)phenyl)amino)-4-oxo-4,5-dihydro-1H-pyrazolo[4,3-c]pyridin-1-yl)tetrahydro-2H-pyran-4-carbonitrile | LRMS (ESI) calc'd for $C_{22}H_{26}N_5O_4S$ [M + H]$^+$: 456, found 454. |

TABLE 8-continued

| Example | Structure | Compound Name | LRMS |
|---|---|---|---|
| I-14 | | (3R,4S)-3-(3-{[2-(2-methylpropyl)-2,3-dihydro-1H-isoindol-5-yl]amino}-4-oxo-4,5-dihydro-1H-pyrazolo[4,3-c]pyridin-1-yl)tetrahydro-2H-pyran-4-carbonitrile | LRMS (ESI) calc'd for $C_{24}H_{29}N_6O_2$ [M + H]$^+$: 433, found 433. |
| I-15 | | (3R,4S)-3-(3-{[2-(1-methylethyl)-2,3-dihydro-1H-isoindol-5-yl]amino}-4-oxo-4,5-dihydro-1H-pyrazolo[4,3-c]pyridin-1-yl)tetrahydro-2H-pyran-4-carbonitrile | LRMS (ESI) calc'd for $C_{23}H_{27}N_6O_2$ [M + H]$^+$: 419, found 419. |
| I-16 | | methyl 5-({1-[(3R,4S)-4-cyanotetrahydro-2H-pyran-3-yl]-4-oxo-4,5-dihydro-1H-pyrazolo[4,3-c]pyridin-3-yl}amino)-2-hydroxybenzenecarboximidoate (from I-17) | LRMS (ESI) calc'd for $C_{20}H_{21}N_6O_4$ [M + H]$^+$: 409, found 409. |
| I-17 | | (3R,4S)-3-{3-[(4-fluoro-3-methoxyphenyl)amino]-4-oxo-4,5-dihydro-1H-pyrazolo[4,3-c]pyridin-1-yl}tetrahydro-2H-pyran-4-carbonitrile | LRMS (ESI) calc'd for $C_{19}H_{19}N_5O_3F$ [M + H]$^+$: 384, found 384. |

TABLE 8-continued

| Example | Structure | Compound Name | LRMS |
|---|---|---|---|
| 1-18 | 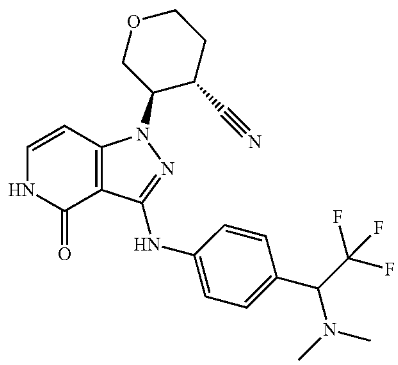 [SMILES: CN(C)C(c1ccc(Nc2nn([C@H]3COCC[C@@H]3C#N)c3cc[nH]c(=O)c23)cc1)C(F)(F)F] | (3R,4S)-3-[3-({4-[(1R, or 1S)-1-(dimethylamino)-2,2,2-trifluoroethyl]phenyl}amino)-4-oxo-4,5-dihydro-1H-pyrazolo[4,3-c]pyridin-1-yl]tetrahydro-2H-pyran-4-carbonitrile (separated as free pyridone, SFC peak 1 using CHIRALCEL® OJ-H, 15% MeOH in $CO_2$, Tr = 6.1 minutes) | LRMS (ESI) calc'd for $C_{22}H_{23}N_6O_2F_3Na$ $[M + Na]^+$: 461, found 483. |
| 1-19 | 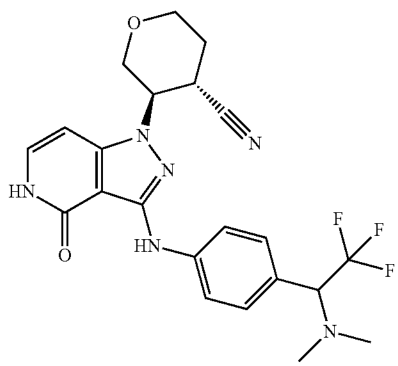 [SMILES: CN(C)C(c1ccc(Nc2nn([C@H]3COCC[C@@H]3C#N)c3cc[nH]c(=O)c23)cc1)C(F)(F)F] | (3R,4S)-3-[3-({4-[(1S or 1R)-1-(dimethylamino)-2,2,2-trifluoroethyl]phenyl}amino)-4-oxo-4,5-dihydro-1H-pyrazolo[4,3-c]pyridin-1-yl]tetrahydro-2H-pyran-4-carbonitrile (separated as free pyridone, SFC peak 2 using CHIRALCEL® OJ-H, 15% MeOH in $CO_2$, Tr = 7.2 minutes) | LRMS (ESI) calc'd for $C_{22}H_{23}N_6O_2F_3Na$ $[M + Na]^+$: 461, found 483. |
| 1-20 | 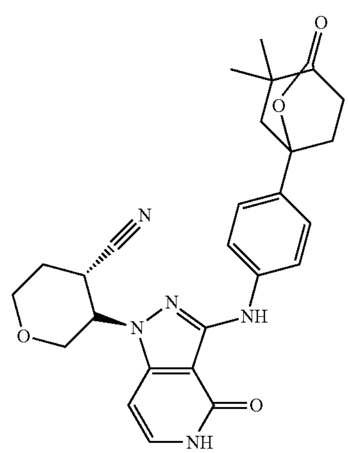 | (3R,4S)-3-(3-{[4-(5,5-dimethyl-3-oxo-2-oxabicyclo[2.2.2]oct-1-yl)phenyl]amino}-4-oxo-4,5-dihydro-1H-pyrazolo[4,3-c]pyridin-1-yl)tetrahydro-2H-pyran-4-carbonitrile (derived from SFC peak 1 on OBn intermediate, CHIRALPAK® AS-H, 35% MeOH in $CO_2$ with 0.25% DMEA, Tr = 3.6 minutes) | LRMS (ESI) calc'd for $C_{27}H_{30}N_5O_4$ $[M + H]^+$: 488, found 488. |
| 1-21 | 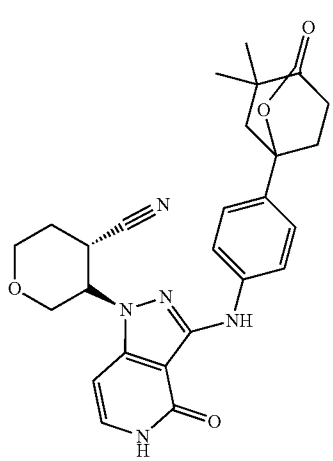 | (3R,4S)-3-(3-{[4-(5,5-dimethyl-3-oxo-2-oxabicyclo[2.2.2]oct-1-yl)phenyl]amino}-4-oxo-4,5-dihydro-1H-pyrazolo[4,3-c]pyridin-1-yl)tetrahydro-2H-pyran-4-carbonitrile (derived from SFC peak 2 on OBn intermediate, CHIRALPAK® AS-H, 35% MeOH in $CO_2$ with 0.25% DMEA, Tr = 4.6 minutes) | LRMS (ESI) calc'd for $C_{27}H_{30}N_5O_4$ $[M + H]^+$: 488, found 488. |

TABLE 8-continued

| Example | Structure | Compound Name | LRMS |
| --- | --- | --- | --- |
| 1-22 | 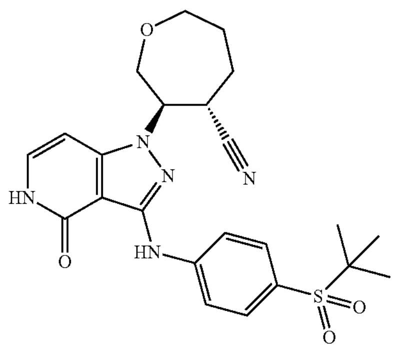 [SMILES: CC(C)(C)S(=O)(=O)c1ccc(Nc2nn([C@H]3COCCC[C@@H]3C#N)c3cc[nH]c(=O)c23)cc1] | (3R,4S or 3S,4R)-3-(3-{[4-(tert-butylsulfonyl)phenyl]amino}-4-oxo-4,5-dihydro-1H-pyrazolo[4,3-c]pyridin-1-yl)oxepane-4-carbonitrile (derived from racemic I-5, peak 1 of HPLC separation of racemic trans isomer pyridone using CHIRALPAC ® IC-3, Hexanes (+0.1% TEA):EtOH = 1:1, Tr = 3.6 minutes) | LRMS (ESI) calc'd for $C_{23}H_{28}N_5O_4S$ $[M + H]^+$: 470, found 470. |
| 1-23 | 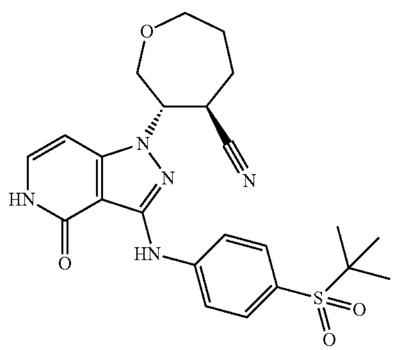 [SMILES: CC(C)(C)S(=O)(=O)c1ccc(Nc2nn([C@@H]3COCCC[C@H]3C#N)c3cc[nH]c(=O)c23)cc1] | (3S,4R or 3R,4S)-3-(3-{[4-(tert-butylsulfonyl)phenyl]amino}-4-oxo-4,5-dihydro-1H-pyrazolo[4,3-c]pyridin-1-yl)oxepane-4-carbonitrile (derived from racemic I-5, peak 2 of HPLC separation of racemic trans isomer pyridone using CHIRALPAK ® IC-3, Hexanes (+0.1% TEA):EtOH = 1:1, Tr = 5.9 minutes) | LRMS (ESI) calc'd for $C_{23}H_{28}N_5O_4S$ $[M + H]^+$: 470, found 470. |
| 1-24 | 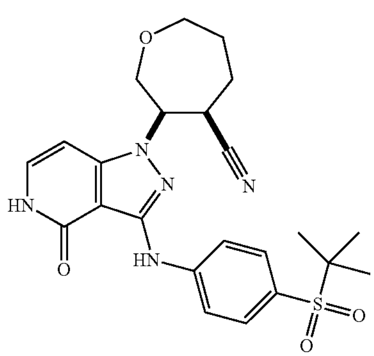 | (3R,4R or 3S,4S)-3-(3-{[4-(tert-butylsulfonyl)phenyl]amino}-4-oxo-4,5-dihydro-1H-pyrazolo[4,3-c]pyridin-1-yl)oxepane-4-carbonitrile (derived from I-6A) | LRMS (ESI) calc'd for $C_{23}H_{28}N_5O_4S$ $[M + H]^+$: 470, found 470. |
| 1-25 | 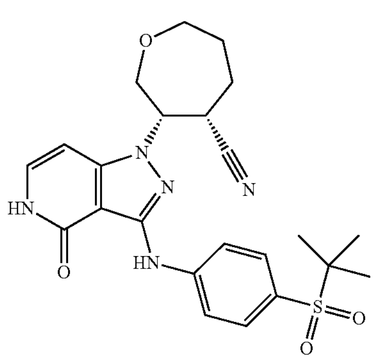 [SMILES: CC(C)(C)S(=O)(=O)c1ccc(Nc2nn([C@@H]3COCCC[C@@H]3C#N)c3cc[nH]c(=O)c23)cc1] | (3S,4S or 3R,4R)-3-(3-{[4-(tert-butylsulfonyl)phenyl]amino}-4-oxo-4,5-dihydro-1H-pyrazolo[4,3-c]pyridin-1-yl)oxepane-4-carbonitrile (derived from I-6B) | LRMS (ESI) calc'd for $C_{23}H_{28}N_5O_4S$ $[M + H]^+$: 470, found 470. |

TABLE 8-continued

| Example | Structure | Compound Name | LRMS |
|---|---|---|---|
| 1-26 | 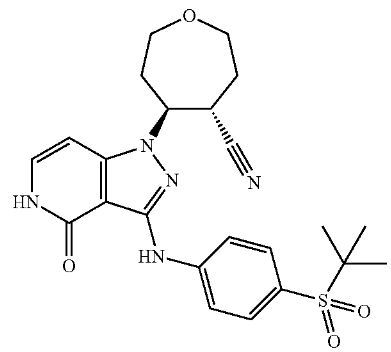 [SMILES: CC(C)(C)S(=O)(=O)c1ccc(Nc2nn([C@H]3CCOCC[C@@H]3C#N)c3cc[nH]c(=O)c23)cc1] | (4S,5S or 4R,5R)-5-(3-{[4-(tert-butylsulfonyl)phenyl]amino}-4-oxo-4,5-dihydro-1H-pyrazolo[4,3-c]pyridin-1-yl)oxepane-4-carbonitrile (derived from racemic I-8, peak 1 from HPLC using CHIRALPAK® IC-3 with hexanes (0.1% TEA) and EtOH = 1:1, Tr = 3.2 minutes on free pyridone) | LRMS (ESI) calc'd for $C_{23}H_{28}N_5O_4S$ $[M + H]^+$: 470, found 470. |
| 1-27 | 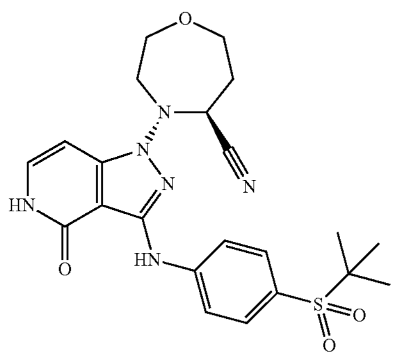 | (4R,5R or 4S,5S)-5-(3-{[4-(tert-butylsulfonyl)phenyl]amino}-4-oxo-4,5-dihydro-1H-pyrazolo[4,3-c]pyridin-1-yl)oxepane-4-carbonitrile (derived from racemic I-8, peak 2 from HPLC using CHIRALPAK® IC-3 with hexanes (0.1% TEA) and EtOH = 1:1, Tr = 5.7 minutes on free pyridone) | LRMS (ESI) calc'd for $C_{23}H_{28}N_5O_4S$ $[M + H]^+$: 470, found 470. |
| 1-28 | 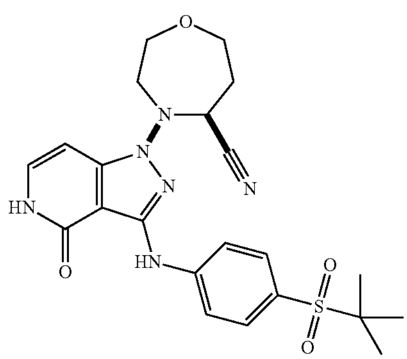 | (4R,5S or 4S,5R)-5-(3-{[4-(tert-butylsulfonyl)phenyl]amino}-4-oxo-4,5-dihydro-1H-pyrazolo[4,3-c]pyridin-1-yl)oxepane-4-carbonitrile (derived from I-7A) | LRMS (ESI) calc'd for $C_{23}H_{28}N_5O_4S$ $[M + H]^+$: 470, found 470. |
| 1-29 | 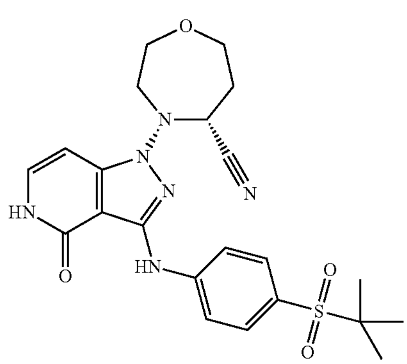 | (4S,5R or 4R,5S)-5-(3-{[4-(tert-butylsulfonyl)phenyl]amino}-4-oxo-4,5-dihydro-1H-pyrazolo[4,3-c]pyridin-1-yl)oxepane-4-carbonitrile (derived from 1-7B) | LRMS (ESI) calc'd for $C_{23}H_{28}N_5O_4S$ $[M+ H]^+$: 470, found 470. |

TABLE 8-continued

| Example | Structure | Compound Name | LRMS |
|---|---|---|---|
| 1-30 | 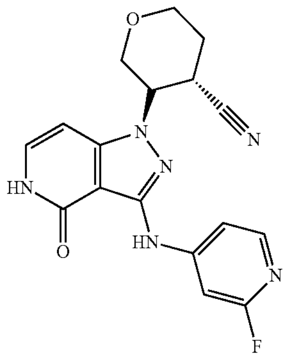 | (3R,4S)-3-{3-[(2-fluoropyridin-4-yl)amino]-4-oxo-4,5-dihydro-1H-pyrazolo[4,3-c]pyridin-1-yl}tetrahydro-2H-pyran-4-carbonitrile | LRMS (ESI) calc'd for $C_{17}H_{16}N_6O_2F$ [M + H]$^+$: 355, found 355. |
| 1-31 | 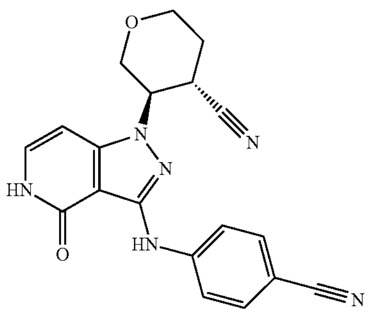 [SMILES: N#Cc1ccc(Nc2nn([C@H]3COCC[C@@H]3C#N)c3cc[nH]c(=O)c23)cc1] | (3R,4S)-3-{3-[(4-cyanophenyl)amino]-4-oxo-4,5-dihydro-1H-pyrazolo[4,3-c]pyridin-1-yl}tetrahydro-2H-pyran-4-carbonitrile | LRMS (ESI) calc'd for $C_{19}H_{17}N_6O_2$ [M + H]$^+$: 361, found 361. |
| 1-32 | 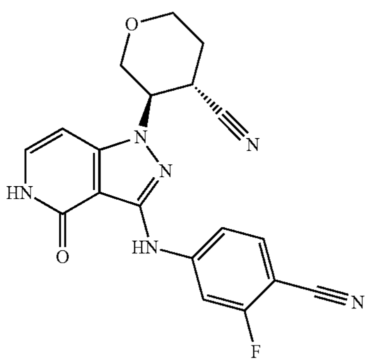 [SMILES: N#Cc1ccc(Nc2nn([C@H]3COCC[C@@H]3C#N)c3cc[nH]c(=O)c23)cc1F] | (3R,4S)-3-{3-[(4-cyano-3-fluorophenyl)amino]-4-oxo-4,5-dihydro-1H-pyrazolo[4,3-c]pyridin-1-yl}tetrahydro-2H-pyran-4-carbonitrile | LRMS (ESI) calc'd for $C_{19}H_{16}N_6O_2F$ [M + H]$^+$: 379, found 379. |
| 1-33 | 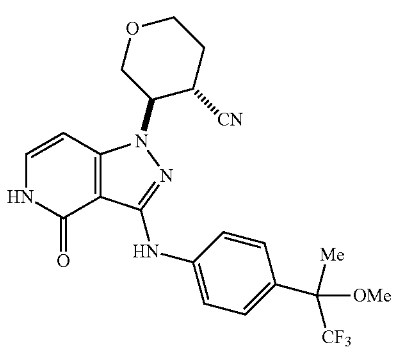 [SMILES: COC(C)(c1ccc(Nc2nn([C@H]3COCC[C@@H]3C#N)c3cc[nH]c(=O)c23)cc1)C(F)(F)F] | (3R,4S)-3-(4-oxo-3-((4-((S or R)-1,1,1-trifluoro-2-methoxypropan-2-yl)phenyl)amino)-4,5-dihydro-1H-pyrazolo[4,3-c]pyridin-1-yl)tetrahydro-2H-pyran-4-carbonitrile (derived from I-19-2A) | LRMS (ESI) Calc'd for $C_{22}H_{23}F_3N_5O_3$ [M + H]$^+$: 462, found 462. |

TABLE 8-continued

| Example | Structure | Compound Name | LRMS |
|---|---|---|---|
| 1-34 | 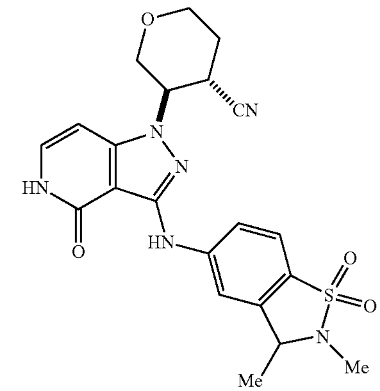 [SMILES: CC1c2cc(Nc3nn([C@H]4COCC[C@@H]4C#N)c4cc[nH]c(=O)c34)ccc2S(=O)(=O)N1C] | (3R,4S)-3-(3-(((R or S)-2,3-dimethyl-1,1-dioxido-2,3-dihydrobenzo[d]isothiazol-5-yl)amino)-4-oxo-4,5-dihydro-1H-pyrazolo[4,3-c]pyridin-1-yl)tetrahydro-2H-pyran-4-carbonitrile (derived from I-12-4A) | LRMS (ESI) Calc'd for $C_{21}H_{23}N_6O_4S$ [M + H]$^+$: 455, found 455. |
| 1-35 | 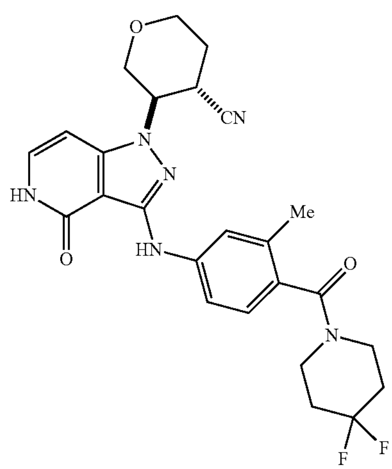 [SMILES: Cc1cc(Nc2nn([C@H]3COCC[C@@H]3C#N)c3cc[nH]c(=O)c23)ccc1C(=O)N1CCC(F)(F)CC1] | (3R,4S)-3-(3-((4-(4,4-difluoropiperidine-1-carbonyl)-3-methylphenyl)amino)-4-oxo-4,5-dihydro-1H-pyrazolo[4,3-c]pyridin-1-yl)tetrahydro-2H-pyran-4-carbonitrile | LRMS (ESI) Calc'd for $C_{25}H_{27}F_2N_6O_3$ [M + H]$^+$: 497, found 497. |
| 1-36 | 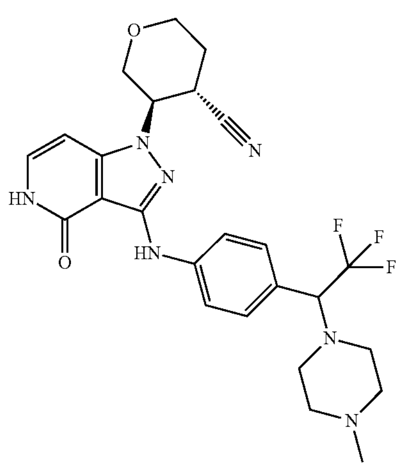 [SMILES: CN1CCN(C(c2ccc(Nc3nn([C@H]4COCC[C@@H]4C#N)c4cc[nH]c(=O)c34)cc2)C(F)(F)F)CC1] | (3R,4S)-3-[4-oxo-3-({4-[(1R or 1S)-2,2,2-trifluoro-1-(4-methylpiperazin-1-yl)ethyl]phenyl}amino)-4,5-dihydro-1H-pyrazolo[4,3-c]pyridin-1-yl]tetrahydro-2H-pyran-4-carbonitrile (from racemic I-21-6. Derived from Peak A via SFC, Lux-2, 40% EtOH + 0.25% DMEA in CO$_2$, Tr = 7.1 minutes on OBn intermediate) | LRMS (ESI) calc'd for $C_{25}H_{29}F_3N_7O_2$ [M + H]$^+$: 516, found 516. |

TABLE 8-continued

| Example | Structure | Compound Name | LRMS |
|---|---|---|---|
| 1-37 | 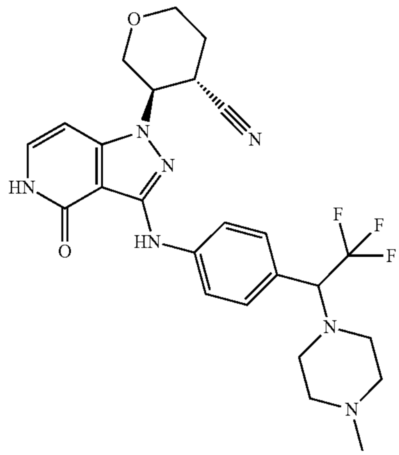 [SMILES: CN1CCN(C(c2ccc(Nc3nn([C@H]4COCC[C@@H]4C#N)c4cc[nH]c(=O)c34)cc2)C(F)(F)F)CC1] | (3R,4S)-3-[4-oxo-3-({4-[(1S or 1R)-2,2,2-trifluoro-1-(4-methylpiperazin-1-yl)ethyl]phenyl}amino)-4,5-dihydro-1H-pyrazolo[4,3-c]pyridin-1-yl]tetrahydro-2H-pyran-4-carbonitrile (from racemic I-21-6. Derived from Peak B via SFC, Lux-2, 40% EtOH + 0.25% DMEA in $CO_2$, Tr = 11.5 minutes on OBn intermediate) | LRMS (ESI) calc'd for $C_{25}H_{29}F_3N_7O_2$ $[M + H]^+$: 516, found 516. |
| 1-38 | 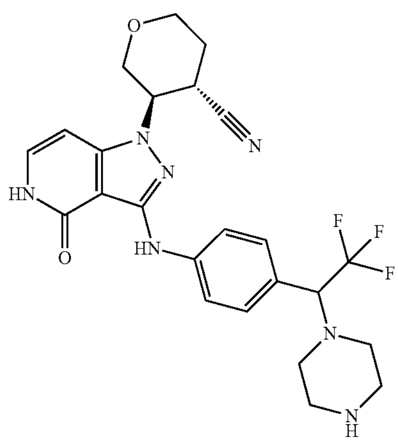 [SMILES: N#C[C@H]1CCOC[C@@H]1n1nc(Nc2ccc(C(N3CCNCC3)C(F)(F)F)cc2)c2c(=O)[nH]ccc21] | (3R,4S)-3-[4-oxo-3-({4-[(1R or 1S)-2,2,2-trifluoro-1-piperazin-1-ylethyl]phenyl}amino)-4,5-dihydro-1H-pyrazolo[4,3-c]pyridin-1-yl]tetrahydro-2H-pyran-4-carbonitrile (from racemic I-21-7. Derived from Peak A via SFC, AD-H, 30% 2-propanol + 0.25% DMEA in $CO_2$, Tr = 4.5 minutes on OBn intermediate) | LRMS (ESI) calc'd for $C_{24}H_{27}F_3N_7O_2$ $[M + H]^+$: 502, found 502. |
| 1-39 | 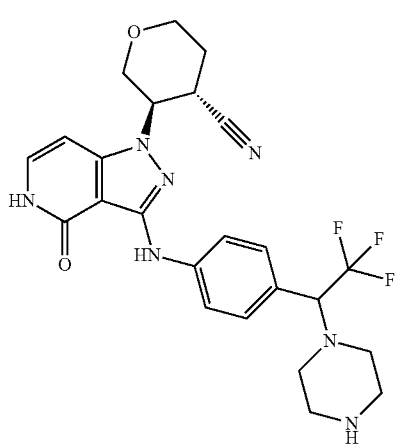 [SMILES: N#C[C@H]1CCOC[C@@H]1n1nc(Nc2ccc(C(N3CCNCC3)C(F)(F)F)cc2)c2c(=O)[nH]ccc21] | (3R,4S)-3-[4-oxo-3-({4-[(1S or 1R)-2,2,2-trifluoro-1-piperazin-1-ylethyl]phenyl}amino)-4,5-dihydro-1H-pyrazolo[4,5-c]pyridin-1-yl]tetrahydro-2H-pyran-4-carbonitrile (from racemic I-21-7. Derived from Peak B via SFC, AD-H, 30% 2-propanol + 0.25% DMEA in $CO_2$, Tr = 7.6 minutes on OBn intermediate) | LRMS (ESI) calc'd for $C_{24}H_{27}F_3N_7O_2$ $[M + H]^+$: 502, found 502. |

TABLE 8-continued

| Example | Structure | Compound Name | LRMS |
|---|---|---|---|
| 1-40 | 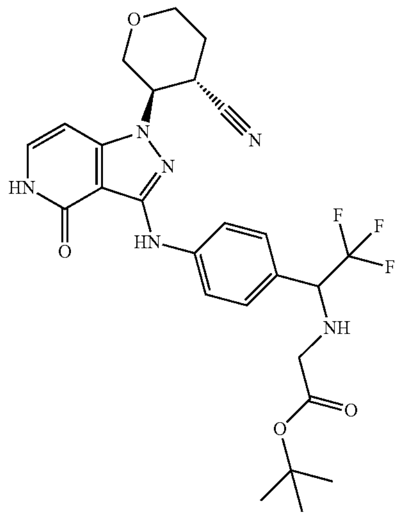 [SMILES: CC(C)(C)OC(=O)CNC(c1ccc(Nc2nn([C@H]3COCC[C@@H]3C#N)c3cc[nH]c(=O)c23)cc1)C(F)(F)F] | tert-butyl N-{[(1R or 1S)-1-[4-({1-[(3R,4S)-4-cyanotetrahydro-2H-pyran-3-yl]-4-oxo-4,5-dihydro-1H-pyrazolo[4,3-c]pyridin-3-yl}amino)phenyl]-2,2,2-trifluoroethyl}glycinate (from racemic I-21-8. Derived from Peak A via SFC, AD-H, 30% MeOH + 0.25% DMEA in CO$_2$, Tr = 5.6 minutes OBn intermediate) | LRMS (ESI) calc'd for C$_{26}$H$_{29}$F$_3$N$_6$O$_4$Na [M + Na]$^+$: 569, found 569. |
| 1-41 | 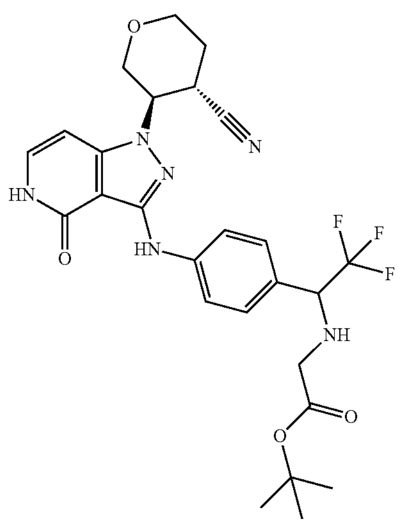 [SMILES: CC(C)(C)OC(=O)CNC(c1ccc(Nc2nn([C@H]3COCC[C@@H]3C#N)c3cc[nH]c(=O)c23)cc1)C(F)(F)F] | tert-butyl N-{(1S or 1R)-1-[4-({1-[(3R,4S)-4-cyanotetrahydro-2H-pyran-3-yl]-4-oxo-4,5-dihydro-1H-pyrazolo[4,3-c]pyridin-3-yl}amino)phenyl]-2,2,2-trifluoroethyl}glycinate (from racemic I-21-8. Derived from Peak B via SFC, AD-H, 30% MeOH + 0.25% DMEA in CO$_2$, Tr = 6.4 minutes on OBn intermediate) | LRMS (ESI) calc'd C$_{26}$H$_{29}$F$_3$N$_6$O$_4$Na [M + Na]$^+$: 569, found 569. |
| 1-42 | 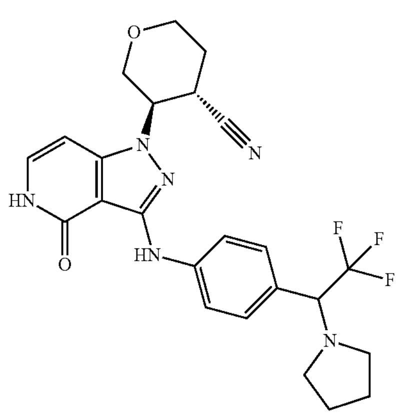 [SMILES: N#C[C@H]1CCOC[C@@H]1n1nc(Nc2ccc(C(N3CCCC3)C(F)(F)F)cc2)c2c(=O)[nH]ccc21] | (3R,4S)-3-[4-oxo-3-({4-[(1R or 1S)-2,2,2-trifluoro-1-pyrrolidin-1-ylethyl]phenyl}amino)-4,5-dihydro-1H-pyrazolo[4,3-c]pyridin-1-yl]tetrahydro-2H-pyran-4-carbonitrile (from racemic I-21-2. Derived from Peak A via SFC, IB, 25% MeOH + 0.25% DMEA in CO$_2$, Tr = 4.5 minutes on OBn intermediate) | LRMS (ESI) calc'd for C$_{24}$H$_{26}$F$_3$N$_6$O$_2$ [M + H]$^+$: 487, found 487. |

TABLE 8-continued

| Example | Structure | Compound Name | LRMS |
|---|---|---|---|
| 1-43 | 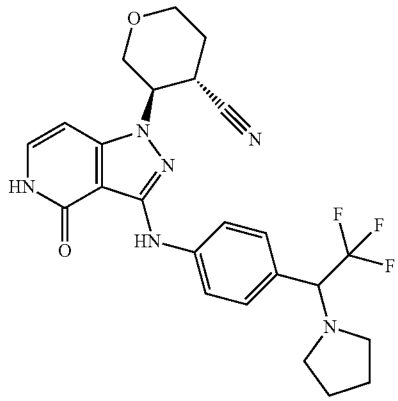 [SMILES: N#C[C@H]1CCOC[C@@H]1n1nc(Nc2ccc(C(N3CCCC3)C(F)(F)F)cc2)c2c(=O)[nH]ccc21] | (3R,4S)-3-[4-oxo-3-({4-[(1S or 1R)-2,2,2-trifluoro-1-pyrrolidin-1-ylethyl]phenyl}amino)-4,5-dihydro-1H-pyrazolo[4,3-c]pyridin-1-yl]tetrahydro-2H-pyran-4-carbonitrile (from racemic I-21-2. Derived from Peak B via SFC, IB, 25% MeOH + 0.25% DMEA in $CO_2$, Tr = 4.8 minutes on OBn intermediate) | LRMS (ESI) calc'd for $C_{24}H_{26}F_3N_6O_2$ $[M + H]^+$: 487, found 487. |
| 1-44 | 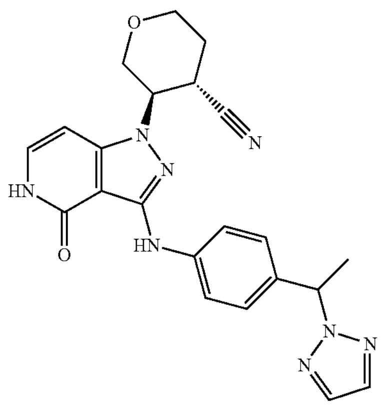 [SMILES: CC(c1ccc(Nc2nn([C@H]3COCC[C@@H]3C#N)c3cc[nH]c(=O)c23)cc1)n1nccn1] | (3R,4S)-3-[4-oxo-3-({4-[(1S or 1R)-1-(2H-1,2,3-triazol-2-yl)ethyl]phenyl}amino)-4,5-dihydro-1H-pyrazolo[4,3-c]pyridin-1-yl]tetrahydro-2H-pyran-4-carbonitrile (from racemic I-25. Derived from Peak A via SFC, OJ-H, 30% MeOH in $CO_2$, Tr = 7.4 minutes on OBn intermediate) | LRMS (ESI) calc'd for $C_{22}H_{23}N_8O_2$ $[M + H]^+$: 431, found 431. |
| 1-45 | 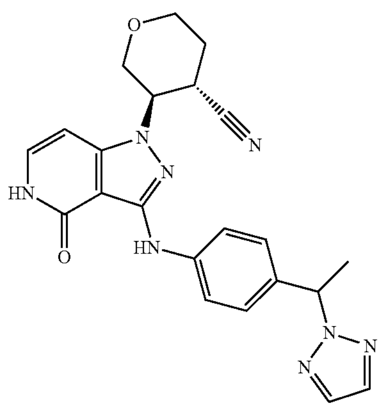 [SMILES: CC(c1ccc(Nc2nn([C@H]3COCC[C@@H]3C#N)c3cc[nH]c(=O)c23)cc1)n1nccn1] | (3R,4S)-3-[4-oxo-3-({4-[(1R or 1S)-1-(2H-1,2,3-triazol-2-yl)ethyl]phenyl}amino)-4,5-dihydro-1H-pyrazolo[4,3-c]pyridin-1-yl]tetrahydro-2H-pyran-4-carbonitrile (from racemic I-25. Derived from Peak B via SFC, OJ-H, 30% MeOH in $CO_2$, Tr = 9.2 minutes on OBn intermediate) | LRMS (ESI) calc'd for $C_{22}H_{23}N_8O_2$ $[M + H]^+$: 431, found 431. |
| 1-46 | 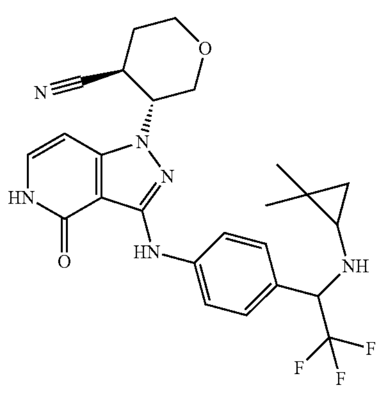 [SMILES: CC1(C)CC1NC(c1ccc(Nc2nn([C@H]3COCC[C@@H]3C#N)c3cc[nH]c(=O)c23)cc1)C(F)(F)F] | (3R,4S)-3-{3-[(4S or 4R-{1S or 1R-[(2,2-dimethylcyclopropyl)amino]-2,2,2-trifluoroethyl}phenyl)amino]-4-oxo-4,5-dihydro-1H-pyrazolo[4,3-c]pyridin-1-yl}tetrahydro-2H-pyran-4-carbonitrile (from I-21-9. Derived from Diastereomeric Peak A via HPLC, Phenyl-Hexyl, 65-85% ACN, Tr = 15.2 minutes on OBn intermediate, then Peak 1 SFC, AD-H, 20% MeOH in $CO_2$, Tr = 4.3 minutes on pyridone final compound) | LRMS (ESI) calc'd for $C_{25}H_{28}F_3N_6O_2$ $[M + H]^+$: 501, found 501. |

TABLE 8-continued

| Example | Structure | Compound Name | LRMS |
|---|---|---|---|
| 1-47 | 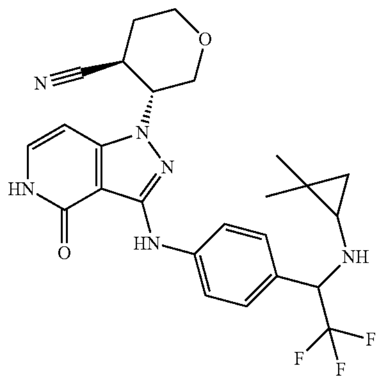 [SMILES: CC1(C)CC1NC(c1ccc(Nc2nn([C@H]3COCC[C@@H]3C#N)c3cc[nH]c(=O)c23)cc1)C(F)(F)F] | (3R,4S)-3-{3-[(4S or 4R-{1S or 1R-[(2,2-dimethylcyclopropyl)amino]-2,2,2-trifluoroethyl}phenyl)amino]-4-oxo-4,5-dihydro-1H-pyrazolo[4,3-c]pyridin-1-yl}tetrahydro-2H-pyran-4-carbonitrile (from I-21-9. Derived from Diastereomeric Peak A via HPLC, Phenyl-Hexyl, 65-85% ACN, Tr = 15.2 minutes on OBn intermediate, then Peak 2 SFC, AD-H, 20% MeOH in CO2, Tr = 6.0 minutes on pyridone final compound) | LRMS (ESI) calc'd for $C_{25}H_{28}F_3N_6O_2$ $[M + H]^+$: 501, found 501. |
| 1-48 | 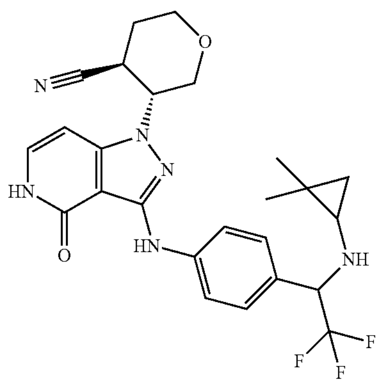 [SMILES: CC1(C)CC1NC(c1ccc(Nc2nn([C@H]3COCC[C@@H]3C#N)c3cc[nH]c(=O)c23)cc1)C(F)(F)F] | (3R,4S)-3-{3-[(4S or 4R-{1S or 1R-[(2,2-dimethylcyclopropyl)amino]-2,2,2-trifluoroethyl}phenyl)amino]-4-oxo-4,5-dihydro-1H-pyrazolo[4,3-c]pyridin-1-yl}tetrahydro-2H-pyran-4-carbonitrile (from I-21-9. Derived from Distereomeric Peak B via HPLC, Phenyl-Hexyl, 65-85% ACN, Tr = 16.5 minutes on OBn intermediate, then Peak 1 SFC, AS—H, 20% MeOH in $CO_2$, Tr = 3.9 minutes on pyridone final compound) | LRMS (ESI) calc'd for $C_{25}H_{28}F_3N_6O_2$ $[M + H]^+$: 501, found 501. |
| 1-49 | 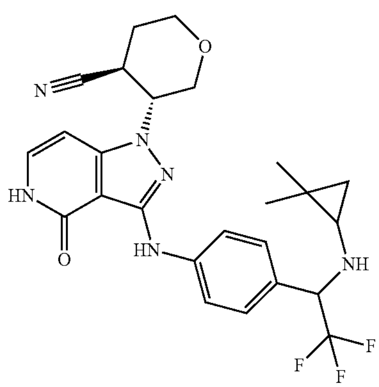 [SMILES: CC1(C)CC1NC(c1ccc(Nc2nn([C@H]3COCC[C@@H]3C#N)c3cc[nH]c(=O)c23)cc1)C(F)(F)F] | (3R,4S)-3-{3-[(4S or 4R-{1S or 1R-[(2,2-dimethylcyclopropyl)amino]-2,2,2-trifluoroethyl}phenyl)amino]-4-oxo-4,5-dihydro-1H-pyrazolo[4,3-c]pyridin-1-yl}tetrahydro-2H-pyran-4-carbonitrile (from I-21-9. Derived from Diastereomeric Peak B via HPLC, Phenyl-Hexyl, 65-85% ACN, Tr = 16.5 minutes on OBn intermediate, then Peak 2 SFC, AS-H, 20% MeOH in $CO_2$, Tr = 6.3 minutes on pyridone final compound) | LRMS (ESI) calc'd for $C_{25}H_{28}F_3N_6O_2$ $[M + H]^+$: 501, found 501. |
| 1-50 | 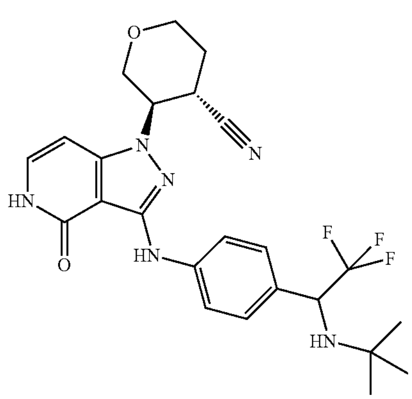 [SMILES: CC(C)(C)NC(c1ccc(Nc2nn([C@H]3COCC[C@@H]3C#N)c3cc[nH]c(=O)c23)cc1)C(F)(F)F] | (3R,4S)-3-[3-({4-[(1R or 1S)-1-(tert-butylamino)-2,2,2-trifluoroethyl]phenyl}amino)-4-oxo-4,5-dihydro-1H-pyrazolo[4,3-c]pyridine-1-yl]tetrahydro-2H-pyran-4-carbonitrile (from racemic I-21-1. Derived from Peak A via SFC, Lux-4, 25% EtOH in $CO_2$, Tr = 5.3 minutes on OBn intermediate) | LRMS (ESI) calc'd for $C_{24}H_{28}F_3N_6O_2$ $[M + H]^+$: 489, found 489. |

TABLE 8-continued

| Example | Structure | Compound Name | LRMS |
|---|---|---|---|
| 1-51 | 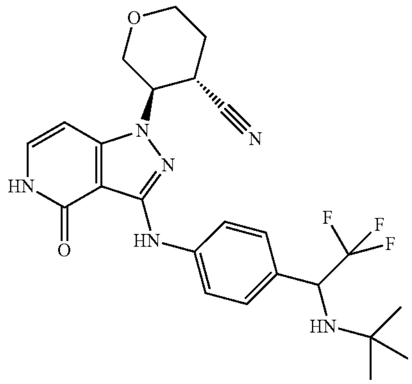 [SMILES: CC(C)(C)NC(c1ccc(Nc2nn([C@H]3COCC[C@@H]3C#N)c3cc[nH]c(=O)c23)cc1)C(F)(F)F] | (3R,4S)-3-[3-[3-({4-[(1S or 1R)-1-(tert-butylamino)-2,2,2-trifluoroethyl]phenyl}amino)-4-oxo-4,5-dihydro-1H-pyrazolo[4,3-c]pyridin-1-yl]tetrahydro-2H-pyran-4-carbonitrile (from racemic I-21.1. Derived from Peak B via SFC, Lux-4, 25% EtOH in CO$_2$, Tr = 5.8 minutes on OBn intermediate) | LRMS (ESI) calc'd for C$_{24}$H$_{28}$F$_3$N$_6$O$_2$ [M + H]$^+$: 489, found 489. |
| 1-52 | 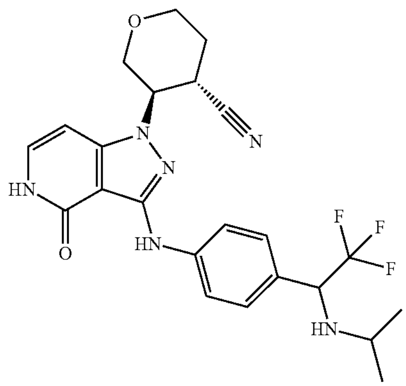 [SMILES: CC(C)NC(c1ccc(Nc2nn([C@H]3COCC[C@@H]3C#N)c3cc[nH]c(=O)c23)cc1)C(F)(F)F] | (3R,4S)-3-{4-oxo-3-[(4-{(1R or 1S)-2,2,2-trifluoro-1-[(1-methylethyl)amino]ethyl}phenyl)amino]-4,5-dihydro-1H-pyrazolo[4,3-c]pyridin-1-yl}tetrahydro-2H-pyran-4-carbonitrile (from racemic I-21-3. Derived from Peak A via SFC, AS-H, 15% MeOH + 0.25% DMEA in CO$_2$, Tr = 4.6 minutes on pyridone final compound) | LRMS (ESI) calc'd C$_{23}$H$_{26}$F$_3$N$_6$O$_2$ [M + H]$^+$: 475, found 475. |
| 1-53 | 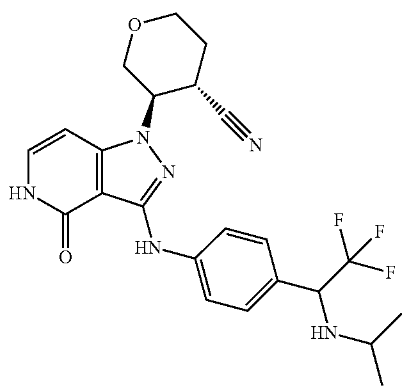 [SMILES: CC(C)NC(c1ccc(Nc2nn([C@H]3COCC[C@@H]3C#N)c3cc[nH]c(=O)c23)cc1)C(F)(F)F] | (3R,4S)-3-{4-oxo-3-[(4-{[1S or 1R)-2,2,2-trifluoro-[(1-methylethyl)amino]ethyl}phenyl)amino]-4,5-dihydro-1H-pyrazolo[4,3-c]pyridin-1-yl}tetrahydro-2H-pyran-4-carbonitrile (from racemic I-21-3. Derived from Peak B via SFC, AS-H, 15% MeOH + 0.25% DMEA in CO$_2$, Tr = 6.1 minutes on pyridone final compound) | LRMS (ESI) calc'd for C$_{23}$H$_{26}$F$_3$N$_6$O$_2$ [M + H]$^+$: 475, found 475. |
| 1-54 | 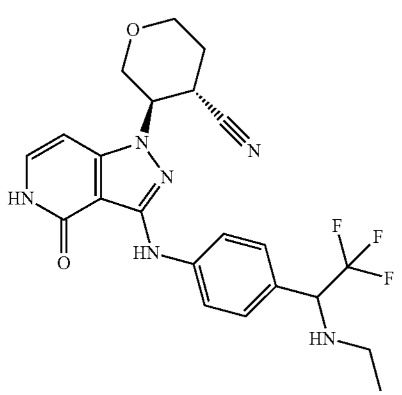 [SMILES: CCNC(c1ccc(Nc2nn([C@H]3COCC[C@@H]3C#N)c3cc[nH]c(=O)c23)cc1)C(F)(F)F] | (3R,4S)-3-[3-({4-[(1R or 1S)-1-(ethylamino)-2,2,2-trifluoroethyl]phenyl}amino)-4-oxo-4,5-dihydro-1H-pyrazolo[4,3-c]pyridin-1-yl]tetrahydro-2H-pyran-4-carbonitrile (from racemic I-21-5. Derived from Peak A via SFC, AS-H, 20% MeOH + 0.25% DMEA in CO$_2$, Tr = 3.6 minutes on pyridone final compound) | LRMS (ESI) calc'd for C$_{22}$H$_{23}$F$_3$N$_6$O$_2$ [M + H]$^+$: 461, found 461. |

TABLE 8-continued

| Example | Structure | Compound Name | LRMS |
|---|---|---|---|
| 1-55 | 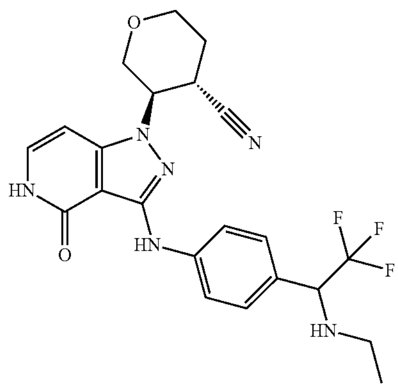 [SMILES: CCNC(c1ccc(Nc2nn([C@H]3COCC[C@@H]3C#N)c3cc[nH]c(=O)c23)cc1)C(F)(F)F] | (3R,4S)-3-[3-({4-[(1S or 1R)-1-(ethylamino)-2,2,2-trifluoroethyl]phenyl}amino)-4-oxo-4,5-dihydro-1H-pyrazolo[4,3-c]pyridin-1-yl]tetrahydro-2H-pyran-4-carbonitrile (from racemic I-21-5. Derived from Peak B via SFC, AS-H, 20% MeOH + 0.25% DMEA in $CO_2$, Tr = 5.7 minutes on pyridone final compound) | LRMS (ESI) calc'd for $C_{22}H_{23}F_3N_6O_2$ $[M + H]^+$: 461, found 461. |
| 1-56 | 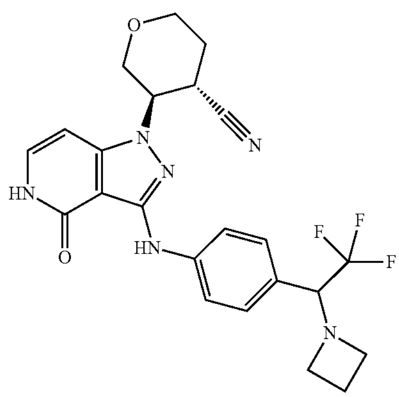 [SMILES: N#C[C@H]1CCOC[C@@H]1n1nc(Nc2ccc(C(N3CCC3)C(F)(F)F)cc2)c2c(=O)[nH]ccc21] | (3R,4S)-3-[3-({4-[(1R or 1S)-1-azetidin-1-yl-2,2,2-trifluoroethyl]phenyl}amino)-4-oxo-4,5-dihydro-1H-pyrazolo[4,3-c]pyridin-1-yl]tetrahydro-2H-pyran-4-carbonitrile (from racemic I-21-4. Derived from Peak A via SFC, AS-D, 15% EtOH + 0.25% DMEA in $CO_2$, Tr = 7.5 minutes on pyridone final compound) | LRMS (ESI) calc'd for $C_{23}H_{24}F_3N_6O_2$ $[M + H]^+$: 473, found 473. |
| 1-57 | 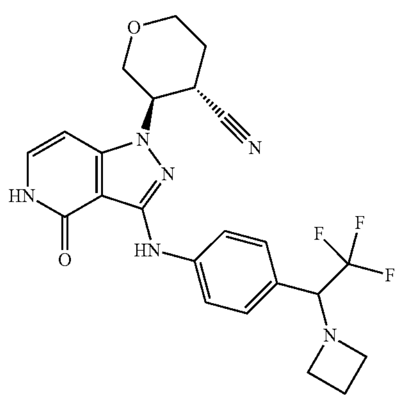 [SMILES: N#C[C@H]1CCOC[C@@H]1n1nc(Nc2ccc(C(N3CCC3)C(F)(F)F)cc2)c2c(=O)[nH]ccc21] | (3R,4S)-3-[3-({4-[(1S or 1R)-1-azetidin-1-yl-2,2,2-trifluoroethyl]phenyl}amino)-4-oxo-4,5-dihydro-1H-pyrazolo[4,3-c]pyridin-1-yl]tetrahydro-2H-pyran-4-carbonitrile (from racemic I-21-4. Derived from Peak B via SFC, AS-D, 15% EtOH + 0.25% DMEA in $CO_2$, Tr = 8.5 minutes on pyridone final compound) | LRMS (ESI) calc'd for $C_{23}H_{24}F_3N_6O_2$ $[M + H]^+$: 473, found 473. |
| 1-58 | 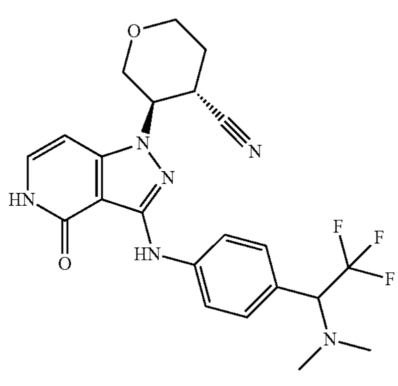 [SMILES: CN(C)C(c1ccc(Nc2nn([C@H]3COCC[C@@H]3C#N)c3cc[nH]c(=O)c23)cc1)C(F)(F)F] | (3R,4S)-3-[3-({4-[(1R or 1S)-1-(dimethylamino)-2,2,2-trifluoroethyl]phenyl}amino)-4-oxo-4,5-dihydro-1H-pyrazolo[4,3-c]pyridin-1-yl]tetrahydro-2H-pyran-4-carbonitrile (from racemic I-21-10. Derived from Peak A via SFC, OJ-H, 20% MeOH in $CO_2$, Tr = 4.2 minutes on pyridone final compound) | LRMS (ESI) calc'd for $C_{22}H_{23}F_3N_6O_2$ $[M + H]^+$: 461, found 461. |

TABLE 8-continued

| Example | Structure | Compound Name | LRMS |
|---|---|---|---|
| 1-59 | 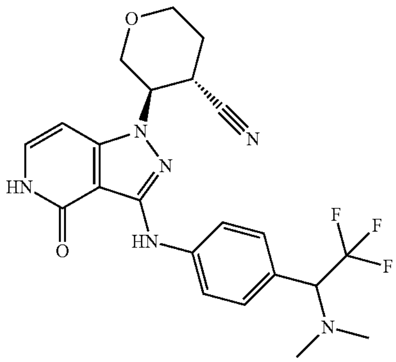 [SMILES: CN(C)C(c1ccc(Nc2nn([C@H]3COCC[C@@H]3C#N)c3cc[nH]c(=O)c23)cc1)C(F)(F)F] | (3R,4S)-3-[3-({4-[(1S or 1R)-1-(dimethylamino)-2,2,2-trifluoroethyl]phenyl}amino)-4-oxo-4,5-dihydro-1H-pyrazolo[4,3-c]pyridin-1-yl]tetrahydro-2H-pyran-4-carbonitrile (from racemic I-21-10. Dervied from Peak B via SFC, OJ-H, 20% MeOH in $CO_2$, Tr = 4.8 minutes on pyridone final compound) | LRMS (ESI) calc'd for $C_{22}H_{23}F_3N_6O_2$ $[M + H]^+$: 461, found 461. |
| 1-60 | 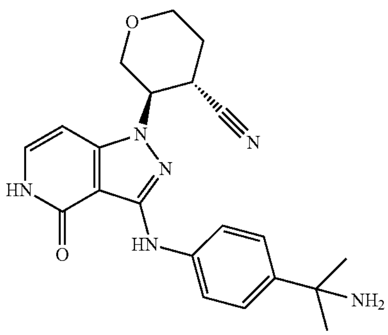 [SMILES: CC(C)(N)c1ccc(Nc2nn([C@H]3COCC[C@@H]3C#N)c3cc[nH]c(=O)c23)cc1] | (3R,4S)-3-(3-{[4-(1-amino-1-methylethyl)phenyl]amino}-4-oxo-4,5-dihydro-1H-pyrazolo[4,3-c]pyridin-1-yl)tetrahydro-2H-pyran-4-carbonitrile | LRMS (ESI) calc'd for $C_{21}H_{25}N_6O_2$ $[M + H]^+$: 393, found 393. |
| 1-61 | 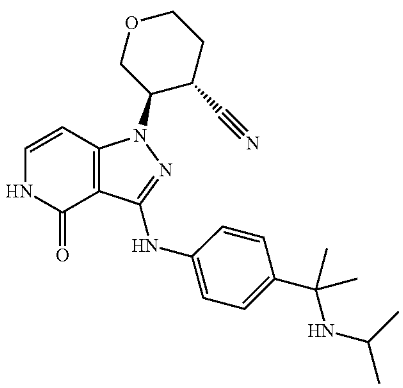 [SMILES: CC(C)NC(C)(C)c1ccc(Nc2nn([C@H]3COCC[C@@H]3C#N)c3cc[nH]c(=O)c23)cc1] | (3R,4S)-3-{3-[(4-{1-methyl-1-[(1-methylethyl)amino]ethyl}phenyl)amino]-4-oxo-4,5-dihydro-1H-pyrazolo[4,3-c]pyridin-1-yl}tetrahydro-2H-pyran-4-carbonitrile | LRMS (ESI) calc'd for $C_{24}H_{30}N_6O_2Na$ $[M + Na]^+$: 457, found 457. |
| 1-62 | 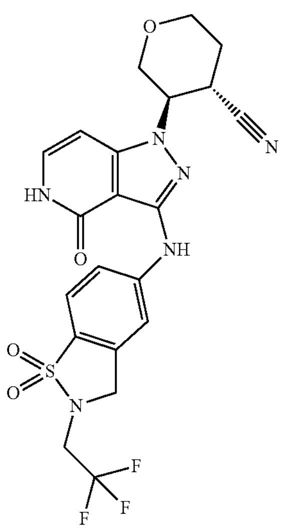 [SMILES: N#C[C@H]1CCOC[C@@H]1n1nc(Nc2ccc3c(c2)CN(CC(F)(F)F)S3(=O)=O)c2c(=O)[nH]ccc21] | (3R,4S)-3-(3-{[1,1-dioxido-2-(2,2,2-trifluoroethyl)-2,3-dihydro-1,2-benzothiazol-5-yl]amino}-4-oxo-4,5-dihydro-1H-pyrazolo[4,3-c]pyridin-1-yl)tetrahydro-2H-pyran-4-carbonitrile | LRMS (ESI) calc'd for $C_{21}H_{20}FN_6O_4S$ $[M + H]^+$: 509, found 509. |

TABLE 8-continued

| Example | Structure | Compound Name | LRMS |
|---|---|---|---|
| 1-63 | 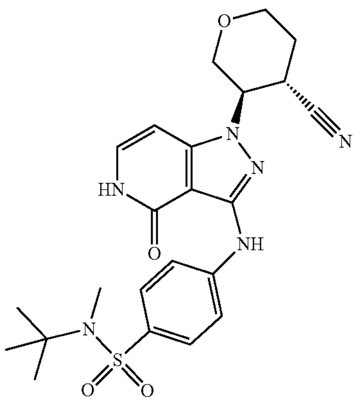 [SMILES: CN(C(C)(C)C)S(=O)(=O)c1ccc(Nc2nn([C@H]3COCC[C@@H]3C#N)c3cc[nH]c(=O)c23)cc1] | N-tert-butyl-4-({1-[(3R,4S)-4-cyanotetrahydro-2H-pyran-3-yl]-4-oxo-4,5-dihydro-1H-pyrazolo[4,3-c]pyridin-3-yl}amino)-N-methylbenzenesulfonamide | LRMS (ESI) calc'd for $C_{23}H_{29}N_6O_4S$ [M + H]$^+$: 485, found 485. |
| 1-64 | 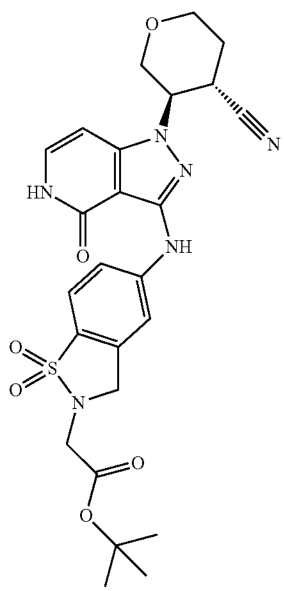 [SMILES: CC(C)(C)OC(=O)CN1Cc2cc(Nc3nn([C@H]4COCC[C@@H]4C#N)c4cc[nH]c(=O)c34)ccc2S1(=O)=O] | tert-butyl [5-({1-[(3R,4S)-4-cyanotetrahydro-2H-pyran-3-yl]-4-oxo-4,5-dihydro-1H-pyrazolo[4,3-c]pyridin-3-yl}amino)-1,1-dioxido-1,2-benzisothiazol-2(3H)-yl]acetate | LRMS (ESI) calc'd for $C_{25}H_{29}N_6O_6S$ [M + H]$^+$: 541, found 541. |
| 1-65 | 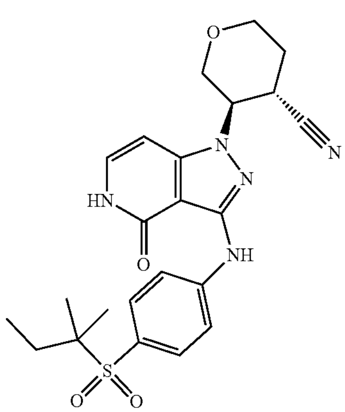 [SMILES: CCC(C)(C)S(=O)(=O)c1ccc(Nc2nn([C@H]3COCC[C@@H]3C#N)c3cc[nH]c(=O)c23)cc1] | (3R,4S)-3-[3-({4-[(1,1-dimethylpropyl)sulfonyl]phenyl}amino)-4-oxo-4,5-dihydro-1H-pyrazolo[4,3-c]pyridin-1-yl]tetrahydro-2H-pyran-4-carbonitrile | LRMS (ESI) calc'd for $C_{23}H_{28}N_5O_4S$ [M + H]$^+$: 470, found 470. |

107 108

TABLE 8-continued

| Example | Structure | Compound Name | LRMS |
|---|---|---|---|
| 1-66 | 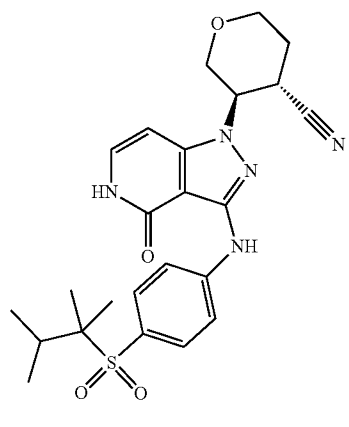 [SMILES: CC(C)C(C)(C)S(=O)(=O)c1ccc(Nc2nn([C@H]3COCC[C@@H]3C#N)c3cc[nH]c(=O)c23)cc1] | (3R,4S)-3-[4-oxo-3-({4-[(1,1,2-trimethylpropyl)sulfonyl]phenyl}amino)-4,5-dihydro-1H-pyrazolo[4,3-c]pyridin-1-yl]tetrahydro-2H-pyran-4-carbonitrile | LRMS (ESI) calc'd for $C_{24}H_{30}N_5O_4S$ [M + H]$^+$: 484, found 484. |
| 1-67 | 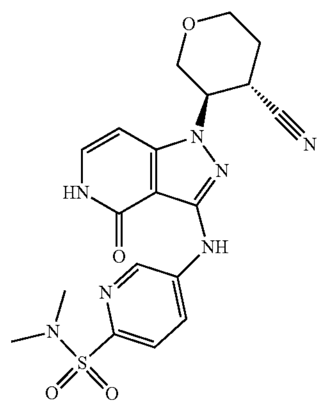 [SMILES: CN(C)S(=O)(=O)c1ccc(Nc2nn([C@H]3COCC[C@@H]3C#N)c3cc[nH]c(=O)c23)cn1] | 5-({1-[(3R,4S)-4-cyanotetrahydro-2H-pyran-3-yl]-4-oxo-4,5-dihydro-1H-pyrazolo[4,3-c]pyridin-3-yl}amino)-N,N-dimethylpyridine-2-sulfonamide | LRMS (ESI) calc'd for $C_{19}H_{22}N_7O_4S$ [M + H]$^+$: 444, found 444. |
| 1-68 | 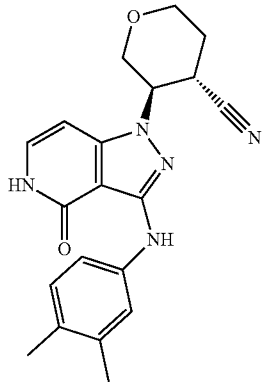 [SMILES: Cc1ccc(Nc2nn([C@H]3COCC[C@@H]3C#N)c3cc[nH]c(=O)c23)cc1C] | (3R,4S)-3-{3-[(3,4-dimethylphenyl)amino]-4-oxo-4,5-dihydro-1H-pyrazolo[4,3-c]pyridin-1-yl}tetrahydro-2H-pyran-4-carbonitrile | LRMS (ESI) calc'd for $C_{20}H_{22}N_5O_2$ [M + H]$^+$: 364, found 364. |

TABLE 8-continued

| Example | Structure | Compound Name | LRMS |
|---|---|---|---|
| 1-69 | 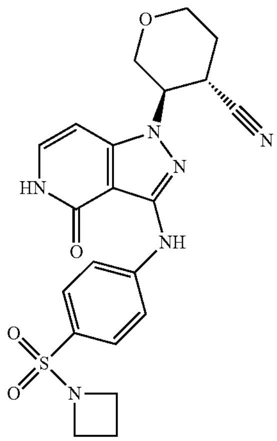 [SMILES: N#C[C@H]1CCOC[C@@H]1n1nc(Nc2ccc(S(=O)(=O)N3CCC3)cc2)c2c(=O)[nH]ccc21] | (3R,4S)-3-(3-{[4-(azetidin-1-ylsulfonyl)phenyl]amino}-4-oxo-4,5-dihydro-1H-pyrazolo[4,3-c]pyridin-1-yl)tetrahydro-2H-pyran-4-carbonitrile | LRMS (ESI) calc'd for $C_{21}H_{23}N_6O_4S$ [M + H]$^+$: 455, found 455. |
| 1-70 | 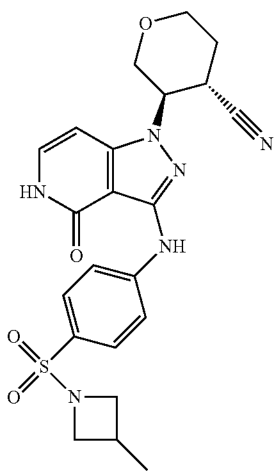 [SMILES: CC1CN(S(=O)(=O)c2ccc(Nc3nn([C@H]4COCC[C@@H]4C#N)c4cc[nH]c(=O)c34)cc2)C1] | (3R,4S)-3-[3-({4-[(3-methylazetidin-1-yl)sulfonyl]phenyl}amino)-4-oxo-4,5-dihydro-1H-pyrazolo[4,3-c]pyridin-1-yl]tetrahydro-2H-pyran-4-carbonitrile | LRMS (ESI) calc'd for $C_{22}H_{25}N_6O_4S$ [M + H]$^+$: 469, found 469. |
| 1-71 | 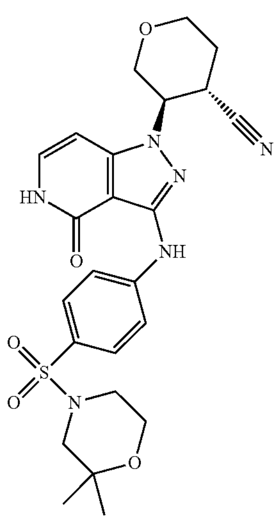 [SMILES: CC1(C)CN(S(=O)(=O)c2ccc(Nc3nn([C@H]4COCC[C@@H]4C#N)c4cc[nH]c(=O)c34)cc2)CCO1] | (3R,4S)-3-[3-({4-[(2,2-dimethylmorpholin-4-yl)sulfonyl]phenyl}amino)-4-oxo-4,5-dihydro-1H-pyrazolo[4,3-c]pyridin-1-yl]tetrahydro-2H-pyran-4-carbonitrile | LRMS (ESI) calc'd for $C_{24}H_{29}N_6O_5S$ [M + H]$^+$: 513, found 513. |

TABLE 8-continued

| Example | Structure | Compound Name | LRMS |
|---|---|---|---|
| 1-72 | 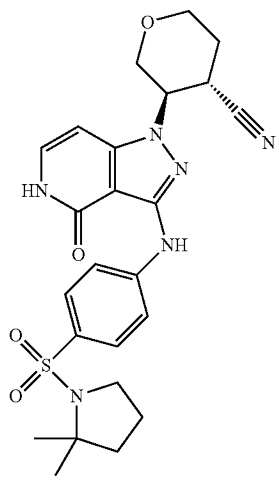 [SMILES: CC1(C)CCCN1S(=O)(=O)c1ccc(Nc2nn([C@H]3COCC[C@@H]3C#N)c3cc[nH]c(=O)c23)cc1] | (3R,4S)-3-[3-({4-[(2,2-dimethylpyrrolidin-1-yl)sulfonyl]phenyl}amino)-4-oxo-4,5-dihydro-1H-pyrazolo[4,3-c]pyridin-1-yl]tetrahydro-2H-pyran-4-carbonitrile | LRMS (ESI) calc'd for $C_{24}H_{29}N_6O_4S$ [M + H]$^+$: 497, found 497. |
| 1-73 | 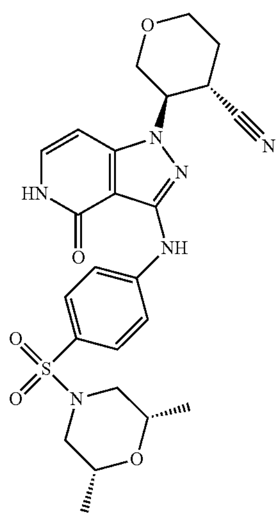 [SMILES: C[C@@H]1CN(S(=O)(=O)c2ccc(Nc3nn([C@H]4COCC[C@@H]4C#N)c4cc[nH]c(=O)c34)cc2)C[C@H](C)O1] | (3R,4S)-3-{3-[(4-{[(cis)-2,6-dimethylmorpholin-4-yl]sulfonyl}phenyl)amino]-4-oxo-4,5-dihydro-1H-pyrazolo[4,3-c]pyridin-1-yl}tetrahydro-2H-pyran-4-carbonitrile | LRMS (ESI) calc'd for $C_{24}H_{29}N_6O_5S$ [M + H]$^+$: 513, found 513. |
| 1-74 | 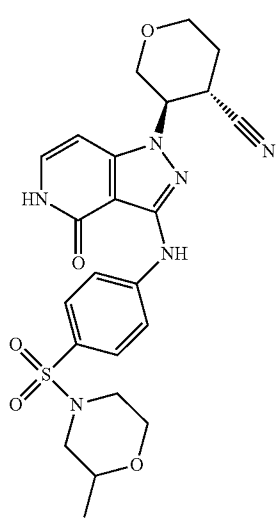 [SMILES: CC1CN(S(=O)(=O)c2ccc(Nc3nn([C@H]4COCC[C@@H]4C#N)c4cc[nH]c(=O)c34)cc2)CCO1] | (3R,4S)-3-{3-[(4-{[(2S or 2R)-2-methylmorpholin-4-yl]sulfonyl}phenyl)amino]-4-oxo-4,5-dihydro-1H-pyrazolo[4,3-c]pyridin-1-yl}tetrahydro-2H-pyran-4-carbonitrile (derived from I-24-3A) | LRMS (ESI) calc'd for $C_{23}H_{27}N_6O_5S$ [M + H]$^+$: 499, found 499. |

TABLE 8-continued

| Example | Structure | Compound Name | LRMS |
|---|---|---|---|
| 1-75 | 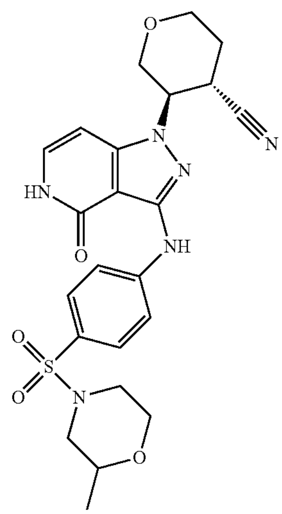 [SMILES: CC1CN(S(=O)(=O)c2ccc(Nc3nn([C@H]4COCC[C@@H]4C#N)c4cc[nH]c(=O)c34)cc2)CCO1] | (3R,4S)-3-{3-[(4-{[(2R or 2S)-2-methylmorpholin-4-yl]sulfonyl}phenyl)amino]-4-oxo-4,5-dihydro-1H-pyrazolo[4,3-c]pyridin-1-yl}tetrahydro-2H-pyran-4-carbonitrile (derived from I-24-3B) | LRMS (ESI) calc'd for $C_{23}H_{27}N_6O_5S$ [M + H]$^+$: 499, found 499. |
| 1-76 | 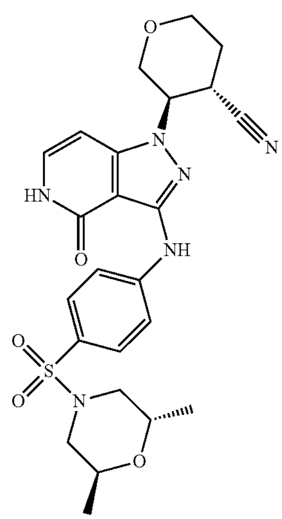 [SMILES: C[C@H]1CN(S(=O)(=O)c2ccc(Nc3nn([C@H]4COCC[C@@H]4C#N)c4cc[nH]c(=O)c34)cc2)C[C@H](C)O1] | (3R,4S)-3-{3-[(4-{[(trans)-2,6-dimethylmorpholin-4-yl]sulfonyl}phenyl)amino]-4-oxo-4,5-dihydro-1H-pyrazolo[4,3-c]pyridin-1-yl}tetrahydro-2H-pyran-4-carbonitrile | LRMS (ESI) calc'd for $C_{24}H_{29}N_6O_5S$ [M + H]$^+$: 513, found 513. |
| 1-77 | 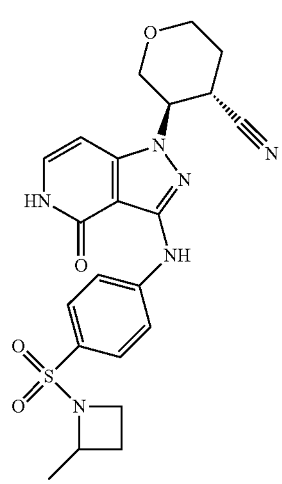 [SMILES: CC1CCN1S(=O)(=O)c1ccc(Nc2nn([C@H]3COCC[C@@H]3C#N)c3cc[nH]c(=O)c23)cc1] | (3R,4S)-3-{3-[(4-{[(2R or 2S)-2-methylazetidin-1-yl]sulfonyl}phenyl)amino]-4-oxo-4,5-dihydro-1H-pyrazolo[4,3-c]pyridin-1-yl}tetrahydro-2H-pyran-4-carbonitrile (derived from I-24-2A) | LRMS (ESI) calc'd for $C_{22}H_{25}N_6O_4S$ [M + H]$^+$: 469, found 469. |

TABLE 8-continued

| Example | Structure | Compound Name | LRMS |
|---|---|---|---|
| 1-78 | 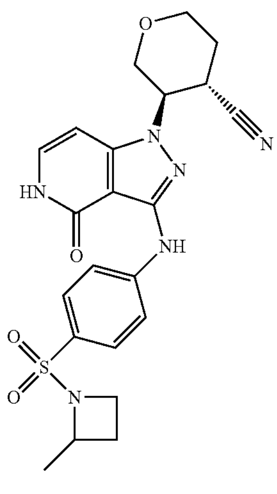 [SMILES: CC1CCN1S(=O)(=O)c1ccc(Nc2nn([C@H]3COCC[C@@H]3C#N)c3cc[nH]c(=O)c23)cc1] | (3R,4S)-3-{3-[(4-{[(2S or 2R)-2-methylazetidin-1-yl]sulfonyl}phenyl)amino]-4-oxo-4,5-dihydro-1H-pyrazolo[4,3-c]pyridin-1-yl}tetrahydro-2H-pyran-4-carbonitrile (derived from I-24-2B) | LRMS (ESI) calc'd for $C_{22}H_{25}N_6O_4S$ $[M + H]^+$: 469, found 469. |
| 1-79 | 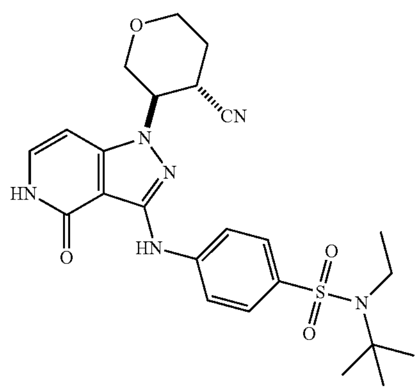 [SMILES: CCN(C(C)(C)C)S(=O)(=O)c1ccc(Nc2nn([C@H]3COCC[C@@H]3C#N)c3cc[nH]c(=O)c23)cc1] | N-(tert-butyl)-4-((1-((3R,4S)-4-cyanotetrahydro-2H-pyran-3-yl)-4-oxo-4,5-dihydro-1H-pyrazolo[4,3-c]pyridin-3-yl)amino)-N-ethylbenzenesulfonamide | LRMS (ESI) calc'd for $C_{24}H_{31}N_6O_4S$ $[M + H]^+$: 499, found 499. |
| 1-80 | 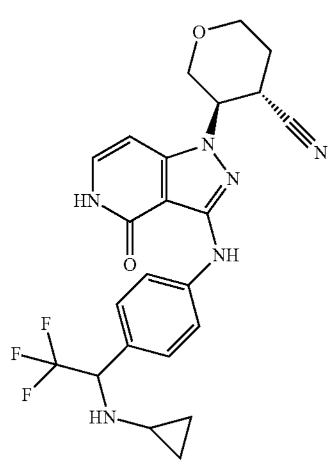 | (3R,4S)-3-[3-({4-[(1S or 1R)-1-(cyclopropylamino)-2,2,2-trifluoroethyl]phenyl}amino)-4-oxo-4,5-dihydro-1H-pyrazolo[4,3-c]pyridin-1-yl]tetrahydro-2H-pyran-4-carbonitrile (from racemic I-21-11. (derived from Peak A via SFC: AS-H, 25% MeOH in $CO_2$, Tr = 4.1 minutes on free pyridone) | LRMS (ESI) calc'd for $C_{30}H_{30}F_3N_6O_2$ $[M + H]^+$: 473, found 473. |

TABLE 8-continued

| Example | Compound Name | LRMS |
|---|---|---|
| 1-81 | (3R,4S)-3-[3-({4-[(1R or 1S)-1-(cyclopropylamino)-2,2,2-trifluoroethyl]phenyl}amino)-4-oxo-4,5-dihydro-1H-pyrazolo[4,3-c]pyridin-1-yl]tetrahydro-2H-pyran-4-carbonitrile (from racemic I-21-11. Derived from Peak B via SFC, AS-H, 25% MeOH in $CO_2$, Tr = 7.3 minutes on free pyridone) | LRMS (ESI) calc'd for $C_{30}H_{30}F_3N_6O_2$ $[M + H]^+$: 473, found 473. |
| 1-82 | (3R,4S)-3-{3-[(4-{[1S or 1R)-1-[(2,2-dimethylpropyl)amino]-2,2,2-trifluoroethyl}phenyl)amino]-4-oxo-4,5-dihydro-1H-pyrazolo[4,3-c]pyridin-1-yl}tetrahydro-2H-pyran-4-carbonitrile (from racemic I-21-12. Derived from Peak A via SFC: AS-H, 20% MeOH in $CO_2$, Tr = 2.6 minutes on free pyridone) | LRMS (ESI) calc'd for $C_{25}H_{29}F_3N_6O_2Na$ $[M + Na]^+$: 525, found 525. |
| 1-83 | (3R,4S)-3-{3-[(4-{(1R or 1S)-1-[(2,2-dimethylpropyl)amino]-2,2,2-trifluoroethyl}phenyl)amino]-4-oxo-4,5-dihydro-1H-pyrazolo[4,3-c]pyridin-1-yl}tetrahydro-2H-pyran-4-carbonitrile (from racemic I-21-12. Derived from Peak B via SFC: AS-H, 20% MeOH in $CO_2$, Tr = 4.8 minutes on free pyridone) | LRMS (ESI) calc'd for $C_{25}H_{29}F_3N_6O_2Na$ $[M + Na]^+$: 525, found 525. |

TABLE 8-continued

| Example | Structure | Compound Name | LRMS |
|---|---|---|---|
| 1-84 | 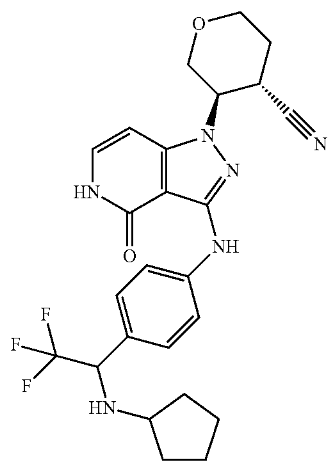 [SMILES: N#C[C@H]1CCOC[C@@H]1n1nc(Nc2ccc(C(NC3CCCC3)C(F)(F)F)cc2)c2c(=O)[nH]ccc21] | (3R,4S)-3-[3-({4-[(1S or 1R)-1-(cyclopentylamino)-2,2,2-trifluoroethyl]phenyl}amino)-4-oxo-4,5-dihydro-1H-pyrazolo[4,3-c]pyridin-1-yl]tetrahydro-2H-pyran-4-carbonitrile (from racemic I-21-13. Derived from Peak A via SFC: AS-H, 20% MeOH in $CO_2$, Tr = 4.8 minutes on free pyridone) | LRMS (ESI) calc'd for $C_{25}H_{28}F_3N_6O_2$ $[M + H]^+$: 501, found 501. |
| 1-85 | 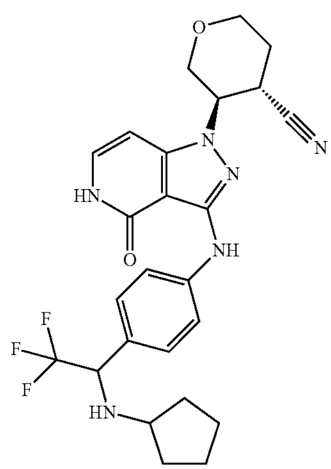 [SMILES: N#C[C@H]1CCOC[C@@H]1n1nc(Nc2ccc(C(NC3CCCC3)C(F)(F)F)cc2)c2c(=O)[nH]ccc21] | (3R,4S)-3-[3-({4-[(1R or 1S)-1-(cyclopentylamino)-2,2,2-trifluoroethyl]phenyl}amino)-4-oxo-4,5-dihydro-1H-pyrazolo[4,3-c]pyridin-1-yl]tetrahydro-2H-pyran-4-carbonitrile (from racemic I-21-13. Derived from Peak B via SFC: AS-H, 20% MeOH in $CO_2$, Tr = 6.6 minutes on free pyridone) | LRMS (ESI) calc'd for $C_{25}H_{28}F_3N_6O_2$ $[M + H]^+$: 501, found 501. |
| 1-86 | 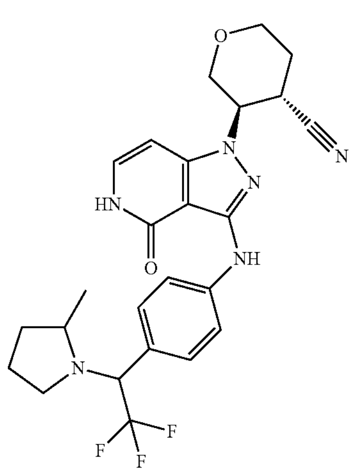 [SMILES: CC1CCCN1C(c1ccc(Nc2nn([C@H]3COCC[C@@H]3C#N)c3cc[nH]c(=O)c23)cc1)C(F)(F)F] | (3R,4S)-3-{4-oxo-3-[(4-{(1R or 1S)-2,2,2-trifluoro-1-[(2S or 2R)-2-methylpyrrolidin-1-yl]ethyl}phenyl)amino]-4,5-dihydro-1H-pyrazolo[4,3-c]pyridin-1-yl}tetrahydro-2H-pyran-4-carbonitrile (from I-21-14. Derived from Diastereomeric Peak A via SFC: Lux-4, 30% MeOH in $CO_2$, Tr = 5.1 minutes, then Peak 1 via SFC: OJ-H, 20% MeOH (with 0.25% DEA) in $CO_2$, Tr = 4.2 minutes on free pyridone) | LRMS (ESI) calc'd for $C_{25}H_{28}F_3N_6O_2$ $[M + H]^+$: 501, found 501. |

TABLE 8-continued

| Example | Structure | Compound Name | LRMS |
|---|---|---|---|
| 1-87 | 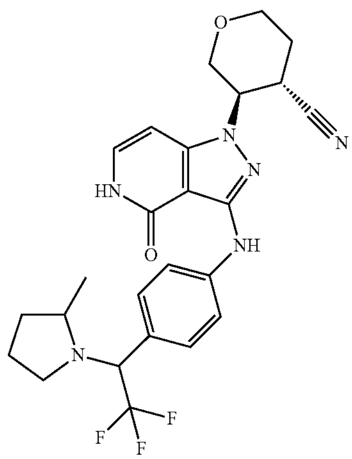 [SMILES: CC1CCCN1C(c1ccc(Nc2nn([C@H]3COCC[C@@H]3C#N)c3cc[nH]c(=O)c23)cc1)C(F)(F)F] | (3R,4S)-3-{4-oxo-3-[(4-{(1S or 1R)-2,2,2-trifluoro-1-[(2R or 2S)-2-methylpyrrolidin-1-yl]ethyl}phenyl)amino]-4,5-dihydro-1H-pyrazolo[4,3-c]pyridin-1-yl}tetrahydro-2H-pyran-4-carbonitrile (from I-21-14. Derived from Diastereomeric Peak A via SFC: Lux-4, 30% MeOH in CO$_2$, Tr = 5.1 minutes, then Peak 2 via SFC, OJ-H, 20% MeOH (with 0.25% DEA) in CO$_2$, Tr = 4.7 minutes on free pyridone) | LRMS (ESI) calc'd for C$_{25}$H$_{28}$F$_3$N$_6$O$_2$ [M + H]$^+$: 501, found 501. |
| 1-88 | 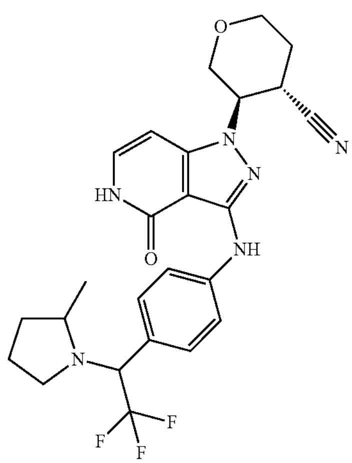 [SMILES: CC1CCCN1C(c1ccc(Nc2nn([C@H]3COCC[C@@H]3C#N)c3cc[nH]c(=O)c23)cc1)C(F)(F)F] | (3R,4S)-3-{4-oxo-3-[(4-{(1S or 1R)-2,2,2-trifluoro-1-[(2S or 2R)-2-methylpyrrolidin-1-yl]ethyl}phenyl)amino]-4,5-dihydro-1H-pyrazolo[4,3-c]pyridin-1-yl}tetrahydro-2H-pyran-4-carbonitrile (from I-21-14. Derived from Diastereomeric Peak B via SFC, Lux-4, 30% MeOH in CO$_2$, Tr = 5.6 minutes, then Peak 1 via SFC, Lux-2, 25% MeOH (with 0.25% DEA) in CO$_2$, Tr = 8.5 minutes on free pyridone) | LRMS (ESI) calc'd for C$_{25}$H$_{28}$F$_3$N$_6$O$_2$ [M + H]$^+$: 501, found 501. |
| 1-89 | 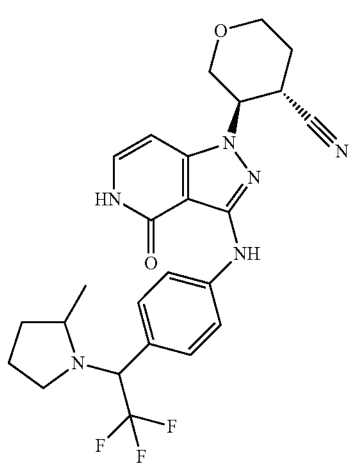 [SMILES: CC1CCCN1C(c1ccc(Nc2nn([C@H]3COCC[C@@H]3C#N)c3cc[nH]c(=O)c23)cc1)C(F)(F)F] | (3R,4S)-3-{4-oxo-3-[(4-{(1R or 1S)-2,2,2-trifluoro-1-[(2R or 2S)-2-methylpyrrolidin-1-yl]ethyl}phenyl)amino]-4,5-dihydro-1H-pyrazolo[4,3-c]pyridin-1-yl}tetrahydro-2H-pyran-4-carbonitrile (from I-21-14. Derived from Diastereomeric Peak B via SFC, Lux-4, 30% MeOH in CO$_2$, Tr = 5.6 minutes, then Peak 2 via SFC, Lux-2, 25% MeOH (with 0.25% DEA) in CO$_2$, Tr = 9.6 minutes on free pyridone) | LRMS (ESI) calc'd for C$_{25}$H$_{28}$F$_3$N$_6$O$_2$ [M + H]$^+$: 501, found 501. |

TABLE 8-continued

| Example | Structure | Compound Name | LRMS |
|---|---|---|---|
| 1-90 | 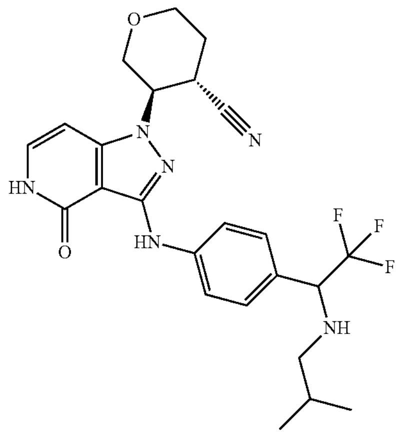 [SMILES: CC(C)CNC(c1ccc(Nc2nn([C@H]3COCC[C@@H]3C#N)c3cc[nH]c(=O)c23)cc1)C(F)(F)F] | (3R,4S)-3-{4-oxo-3-[(4-{(1S or 1R)-2,2,2-trifluoro-1-[(2-methylpropyl)amino]ethyl}phenyl)amino]-4,5-dihydro-1H-pyrazolo[4,3-c]pyridin-1-yl}tetrahydro-2H-pyran-4-carbonitrile (from racemic I-21-16. Derived from Peak A via SFC: AS-H, 20% MeOH (with 0.25% DEA) in $CO_2$, Tr = 3.2 minutes on free pyridone) | LRMS (ESI) calc'd for $C_{24}H_{28}F_3N_6O_2$ $[M + H]^+$: 489, found 489. |
| 1-91 | 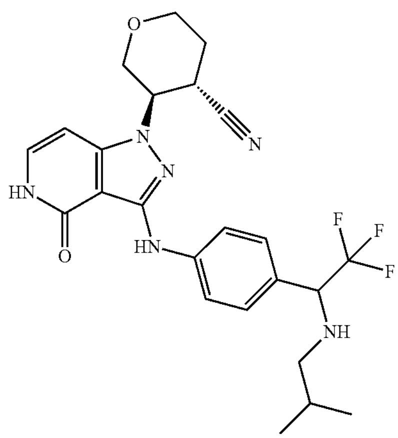 [SMILES: CC(C)CNC(c1ccc(Nc2nn([C@H]3COCC[C@@H]3C#N)c3cc[nH]c(=O)c23)cc1)C(F)(F)F] | (3R,4S)-3-{4-oxo-3-[(4-{(1R or 1S)-2,2,2-trifluoro-1-[(2-methylpropyl)amino]ethyl}phenyl)amino]-4,5-dihydro-1H-pyrazolo[4,3-c]pyridin-1-yl}tetrahydro-2H-pyran-4-carbonitrile (from racemic I-21-15. Derived from Peak B via SFC: AS-H, 20% MeOH (with 0.25% DEA) in $CO_2$, Tr = 5.9 minutes on free pyridone) | LRMS (ESI) calc'd for $C_{24}H_{28}F_3N_6O_2$ $[M + H]^+$: 489, found 489. |
| 1-92 | 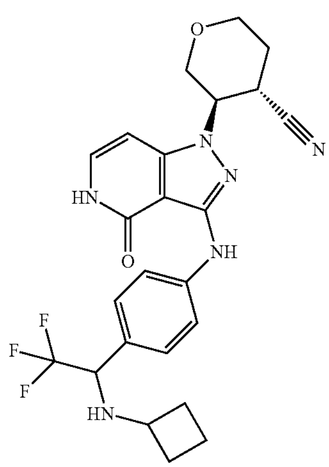 [SMILES: N#C[C@H]1CCOC[C@@H]1n1nc(Nc2ccc(C(NC3CCC3)C(F)(F)F)cc2)c2c(=O)[nH]ccc21] | (3R,4S)-3-[3-({4-[(1S or 1R)-1-(cyclobutylamino)-2,2,2-trifluoroethyl]phenyl}amino)-4-oxo-4,5-dihydro-1H-pyrazolo[4,3-c]pyridin-1-yl]tetrahydro-2H-pyran-4-carbonitrile (from racemic I-21-15. Derived from Peak A via SFC: AS-H, 20% MeOH (with 0.25% DEA) in $CO_2$, Tr = 4.7 minutes on free pyridone) | LRMS (ESI) calc'd for $C_{24}H_{26}F_3N_6O_2$ $[M + H]^+$: 487, found 487. |

TABLE 8-continued

| Example | Structure | Compound Name | LRMS |
|---------|-----------|---------------|------|
| 1-93 | 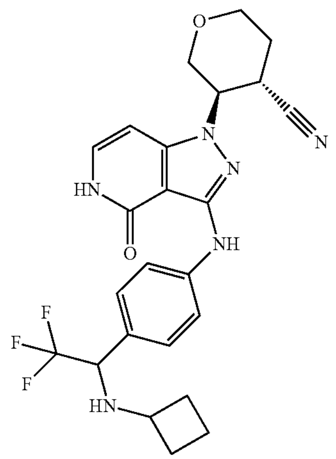 [SMILES: N#C[C@H]1CCOC[C@@H]1n1nc(Nc2ccc(C(NC3CCC3)C(F)(F)F)cc2)c2c(=O)[nH]ccc21] | (3R,4S)-3-[3-({4-[(1R or 1S)-1-(cyclobutylamino)-2,2,2-trifluoroethyl]phenyl}amino)-4-oxo-4,5-dihydro-1H-pyrazolo[4,3-c]pyridin-1-yl]tetrahydro-2H-pyran-4-carbonitrile (from racemic I-21-15. Derived from Peak B via SFC: AS-H, 20% MeOH (with 0.25% DEA) in $CO_2$, Tr = 7.6 minutes on free pyridone) | LRMS (ESI) calc'd for $C_{24}H_{26}F_3N_6O_2$ $[M + H]^+$: 487, found 487. |
| 1-94 | 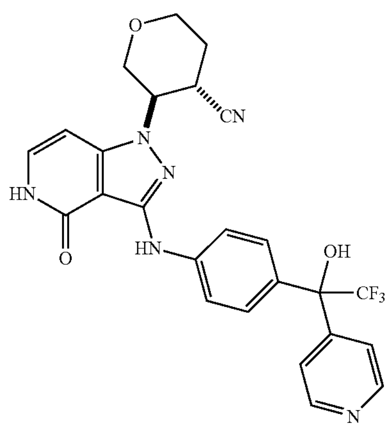 | (3R,4S)-3-(4-oxo-3-((4-((S or R)-2,2,2-trifluoro-1-hydroxy-1-(pyridin-4-yl)ethyl)phenyl)amino)-4,5-dihydro-1H-pyrazolo[4,3-c]pyridin-1-yl)tetrahydro-2H-pyran-4-carbonitrile (from SFC Peak 1, Chiralpak IC: 35% MeOH in $CO_2$, Tr = 3.7 minutes on free pyridone) | LRMS (ESI) Calc'd for $C_{25}H_{22}F_3N_6O_3$ $[M + H]^+$: 511, found 511. |
| 1-95 | 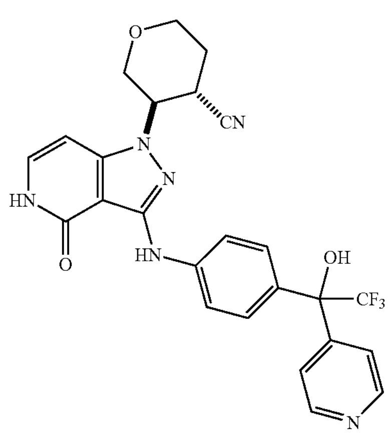 | (3R,4S)-3-(4-oxo-3-((4-((S or R)-2,2,2-trifluoro-1-hydroxy-1-(pyridin-4-yl)ethyl)phenyl)amino)-4,5-dihydro-1H-pyrazolo[4,3-c]pyridin-1-yl)tetrahydro-2H-pyran-4-carbonitrile (from SFC Peak 2, Chiralpak IC: 35% MeOH in $CO_2$, Tr = 5.0 minutes on free pyridone) | LRMS (ESI) Calc'd for $C_{25}H_{22}F_3N_6O_3$ $[M + H]^+$: 511, found 511. |

TABLE 8-continued

| Example | Compound Name | LRMS |
|---|---|---|
| 1-96 | (3R,4S)-3-(4-oxo-3-((4-((S or R)-2,2,2-trifluoro-1-hydroxy-1-(pyridin-2-yl)ethyl)phenyl)amino)-4,5-dihydro-1H-pyrazolo[4,3-c]pyridin-1-yl)tetrahydro-2H-pyran-4-carbonitrile (from SFC Peak 1, Chiralcel OJ-H: 40% MeOH + 0.25% DMEA in $CO_2$, Tr = 2.7 minutes on free pyridone) | LRMS (ESI) Calc'd for $C_{25}H_{22}F_3N_6O_3$ $[M + H]^+$: 511, found 511. |
| 1-97 | (3R,4S)-3-(4-oxo-3-((4-((S or R)-2,2,2-trifluoro-1-hydroxy-1-(pyridin-2-yl)ethyl)phenyl)amino)-4,5-dihydro-1H-pyrazolo[4,3-c]pyridin-1-yl)tetrahydro-2H-pyran-4-carbonitrile (from SFC Peak 2, Chiralcel OJ-H: 40% MeOH + 0.25% DMEA in $CO_2$, Tr = 6.7 minutes on free pyridone) | LRMS (ESI) Calc'd for $C_{25}H_{22}F_3N_6O_3$ $[M + H]^+$: 511, found 511. |
| 1-98 | (3R,4S)-3-(4-oxo-3-((4-((S or R)-3-(trifluoromethyl)pyrrolidin-3-yl)phenyl)amino)-4,5-dihydro-1H-pyrazolo[4,3-c]pyridin-1-yl)tetrahydro-2H-pyran-4-carbonitrile (from SFC Peak 1, Chiralpak AS-H: 25% MeOH + 0.25% DMEA in $CO_2$, Tr = 3.7 minutes on free pyridone) | LRMS (ESI) Calc'd for $C_{23}H_{24}F_3N_6O_2$ $[M + H]^+$: 473, found 473. |
| 1-99 | (3R,4S)-3-(4-oxo-3-((4-((S or R)-3-(trifluoromethyl)pyrrolidin-3-yl)phenyl)amino)-4,5-dihydro-1H-pyrazolo[4,3-c]pyridin-1-yl)tetrahydro-2H-pyran-4-carbonitrile (from SFC Peak 2, Chiralpak AS-H: 25% MeOH + 0.25% DMEA in $CO_2$, Tr = 4.3 minutes on free pyridone) | LRMS (ESI) Calc'd for $C_{23}H_{24}F_3N_6O_2$ $[M + H]^+$: 473, found 473. |

TABLE 8-continued

| Example | Structure | Compound Name | LRMS |
|---|---|---|---|
| 1-100 | 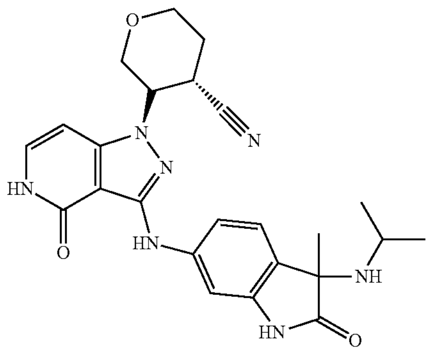 | (3R,4S)-3-[3-({(3R or 3S)-3-methyl-3-[(1-methylethyl)amino]-2-oxo-2,3-dihydro-1H-indol-6-yl}amino)-4-oxo-4,5-dihydro-1H-pyrazolo[4,3-c]pyridin-1-yl]tetrahydro-2H-pyran-4-carbonitrile. (SFC resolution achieved using Chiralpak AD-H: 35% i-PrOH in $CO_2$, Tr = 3.1 mins on free pyridone) mins | LRMS (ESI) Calc'd for $C_{24}H_{28}N_7O_3$ $[M + H]^+$: 462, found 462. |
| 1-101 | 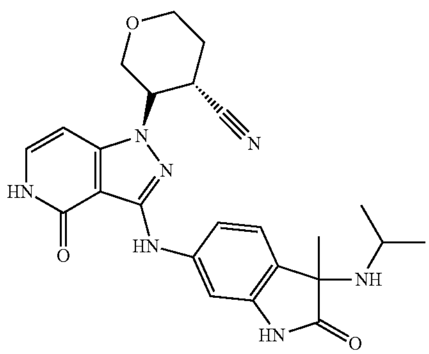 | (3R,4S)-3-[3-({(3S or 3R)-3-methyl-3-[(1-methylethyl)amino]-2-oxo-2,3-dihydro-1H-indol-6-yl}amino)-4-oxo-4,5-dihydro-1H-pyrazolo[4,3-c]pyridin-1-yl]tetrahydro-2H-pyran-4-carbonitrile. (SCF resolution achieved using Chiralpak AD-H: 35% i-PrOH in $CO_2$, Tr = 7.0 minutes on free pyridone) | LRMS (ESI) Calc'd for $C_{24}H_{28}N_7O_3$ $[M + H]^+$: 462, found 462. |

Example 2-1

(3S,4S)-3-{3-[(2-methyl-1,3-benzothiazol-6-yl)amino]-4-oxo-4,5-dihydro-1H-pyrazolo[4,3-c]pyridin-1-yl}tetrahydro-2H-pyran-4-carbonitrile

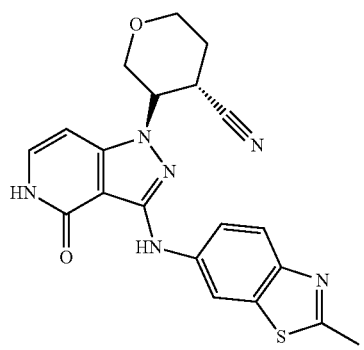

(3R,4S)-3-(3-amino-4-oxo-4,5-dihydro-1H-pyrazolo[4,3-c]pyridin-1-yl)tetrahydro-2H-pyran-4-carbonitrile (52 mg, 0.20 mmol), 6-bromo-2-methylbenzo[d]thiazole (50.2 mg, 0.220 mmol), $Pd_2(dba)_3$ (22 mg, 0.024 mmol), t-Bu-XPhos (20 mg, 0.048 mmol) and potassium acetate (39.3 mg, 0.400 mmol) were added to a microwave vial followed by 2-propanol (2.50 mL). The vials was sealed and degassed by successive evacuation/argon backfill (×3). The resulting mixture was stirred at 85° C. for 18 hours, then cooled to ambient temperature and concentrated in vacuo. The residue was taken into DMSO (2.50 mL), filtered, and the resulting solution was purified directly by reverse-phase HPLC (5-50% acetonitrile in water with 0.1% TFA modifier). Fractions containing pure product were frozen and lyophilized to the title compound as the TFA salt as a solid. LRMS (ESI) calc'd for $C_{20}H_{19}N_6O_2S$ $[M+H]^+$: 407, found 407. $^1H$ NMR (500 MHz, DMSO-d6): δ 11.24 (d, J=6.3 Hz, 1H), 8.40 (d, J=1.9 Hz, 1H), 8.35 (s, 1H), 7.83 (d, J=8.8 Hz, 1H), 7.72 (dd, J=2.3, 8.8 Hz, 1H), 7.31 (dd, J=5.9, 7.3 Hz, 1H), 6.80 (d, J=7.3 Hz, 1H), 4.93 (dt, J=4.5, 10.7 Hz, 1H), 4.01 (m, 2H), 3.83 (dt, 3.8, J=11.8 Hz, 1H), 3.78 (t, J=10.7 Hz, 1H), 2.79 (s, 3H), 2.25 (d, J=12.6 Hz, 1H), 2.09 (dq, J=4.7, 12.6 Hz, 1H).

The following examples outlined in Table 9 were prepared by analogy using the general procedure outlined above for Example 2-1. In select cases, the general procedure was modified to alternatively utilize KOAc base, 2-di-tert-butylphosphino-2',4',6'-triisopropyl-1,1'-biphenyl ligand instead, [(2-di-tert-butylphosphino-2',4',6'-triisopropyl-1,1'-biphenyl)-2-(2'-amino-1,1'-biphenyl)]palladium(II) methanesulfonate (t-BuXPhos Pd G3) precatalyst in place of the individual phosphine and palladium source, and t-amyl alcohol in place of 2-propanol. Additionally, in certain instances the cross coupling could be run between 70-85° C.

TABLE 9

| Example | Structure | Compound Name | LRMS |
|---------|-----------|---------------|------|
| 2-2 | 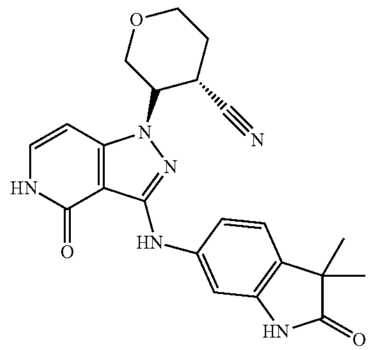 | (3R,4S)-3-{3-[(3,3-dimethyl-2-oxo-2,3-dihydro-1H-indol-6-yl)amino]-4-oxo-4,5-dihydro-1H-pyrazolo[4,3-c]pyridin-1-yl}tetrahydro-2H-pyran-4-carbonitrile | LRMS (ESI) calc'd for $C_{22}H_{23}N_6O_3$ [M + H]$^+$: 419, found 419. |
| 2-3 | 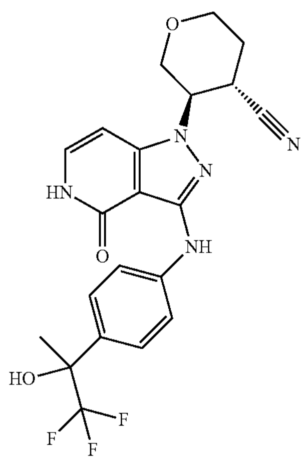 [SMILES: CC(O)(c1ccc(Nc2nn([C@H]3COCC[C@@H]3C#N)c3cc[nH]c(=O)c23)cc1)C(F)(F)F] | (3R,4S)-3-[4-oxo-3-({4-[(1R or 1S)-2,2,2-trifluoro-1-hydroxy-1-methylethyl]phenyl}amino)-4,5-dihydro-1H-pyrazolo[4,3-c]pyridin-1-yl]tetrahydro-2H-pyran-4-carbonitrile (derived from I-19-1A) | LRMS (ESI) calc'd for $C_{21}H_{21}F_3N_5O_3$ [M + H]$^+$: 448, found 448. |
| 2-4 | 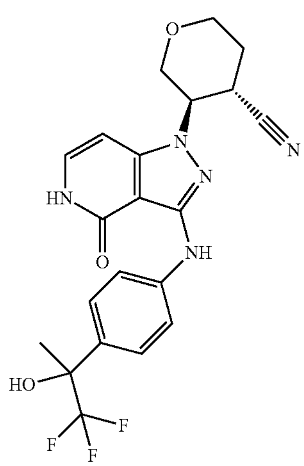 [SMILES: CC(O)(c1ccc(Nc2nn([C@H]3COCC[C@@H]3C#N)c3cc[nH]c(=O)c23)cc1)C(F)(F)F] | (3R,4S)-3-[4-oxo-3-({4-[(1R or 1S)-2,2,2-trifluoro-1-hydroxy-1-methylethyl]phenyl}amino)-4,5-dihydro-1H-pyrazolo[4,3-c]pyridin-1-yl]tetrahydro-2H-pyran-4-carbonitrile (derived from I-19-1B) | LRMS (ESI) calc'd for $C_{21}H_{21}F_3N_5O_3$ [M + H]$^+$: 448, found 448. |

TABLE 9-continued

| Example | Structure | Compound Name | LRMS |
|---------|-----------|---------------|------|
| 2-5 | 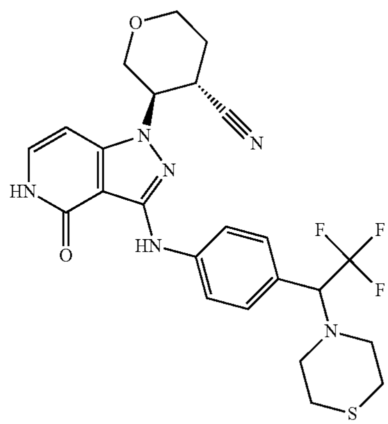 [SMILES: N#C[C@H]1CCOC[C@@H]1n1nc(Nc2ccc(C(N3CCSCC3)C(F)(F)F)cc2)c2c(=O)[nH]ccc21] | (3R,4S)-3-[4-oxo-3-({4-[(1S or 1R)-2,2,2-trifluoro-1-thiomorpholin-4-ylethyl]phenyl}amino)-4,5-dihydro-1H-pyrazolo[4,3-c]pyridin-1-yl]tetrahydro-2H-pyran-4-carbonitrile (derived from I-21-18) | LRMS (ESI) calc'd for $C_{24}H_{25}F_3N_6O_2SNa$ [M + H]$^+$: 541, found 541. |
| 2-6 | 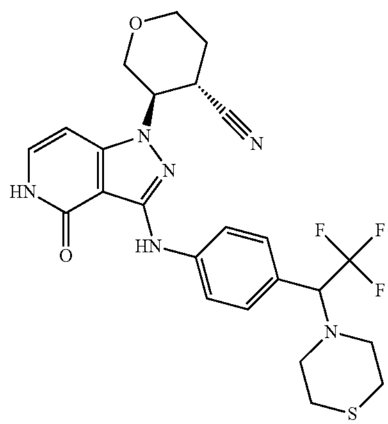 [SMILES: N#C[C@H]1CCOC[C@@H]1n1nc(Nc2ccc(C(N3CCSCC3)C(F)(F)F)cc2)c2c(=O)[nH]ccc21] | (3R,4S)-3-[4-oxo-3-({4-[(1R or 1S)-2,2,2-trifluoro-1-thiomorpholin-4-ylethyl]phenyl}amino)-4,5-dihydro-1H-pyrazolo[4,3-c]pyridin-1-yl]tetrahydro-2H-pyran-4-carbonitrile (derived from I-21-17) | LRMS (ESI) calc'd for $C_{24}H_{25}F_3N_6O_2SNa$ [M + Na]$^+$: 541, found 541. |
| 2-7 | 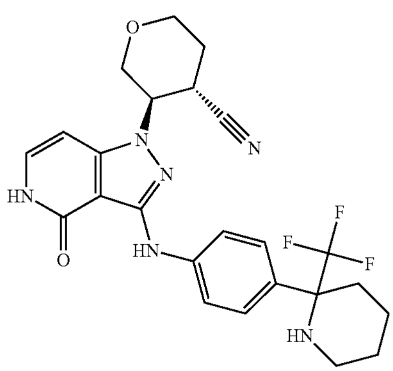 [SMILES: N#C[C@H]1CCOC[C@@H]1n1nc(Nc2ccc(C3(C(F)(F)F)CCCCN3)cc2)c2c(=O)[nH]ccc21] | (3R,4S)-3-[4-oxo-3-({4-[(2S or 2R)-2-(trifluoromethyl)piperidin-2-yl]phenyl}amino)-4,5-dihydro-1H-pyrazolo[4,3-c]pyridin-1-yl]tetrahydro-2H-pyran-4-carbonitrile (derived from I-27) | LRMS (ESI) calc'd for $C_{24}H_{26}F_3N_6O_2$ [M + H]$^+$: 487, found 487. |
| 2-8 | 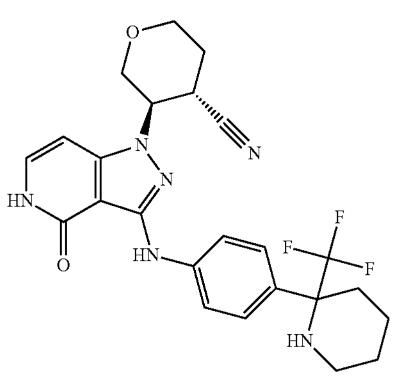 [SMILES: N#C[C@H]1CCOC[C@@H]1n1nc(Nc2ccc(C3(C(F)(F)F)CCCCN3)cc2)c2c(=O)[nH]ccc21] | (3R,4S)-3-[4-oxo-3-({4-[(2R or 2S)-2-(trifluoromethyl)piperidin-2-yl]phenyl}amino)-4,5-dihydro-1H-pyrazolo[4,3-c]pyridin-1-yl]tetrahydro-2H-pyran-4-carbonitrile (derived from I-26) | LRMS (ESI) calc'd for $C_{24}H_{26}F_3N_6O_2$ [M + H]$^+$: 487, found 487. |

Example 3-1

(3R,4S)-3-(3-((4-chloro-3-(methylsulfonyl)phenyl)amino)-4-oxo-4,5-dihydro-1H-pyrazolo[4,3-t]pyridin-1-yl)tetrahydro-2H-pyran-4-carbonitrile

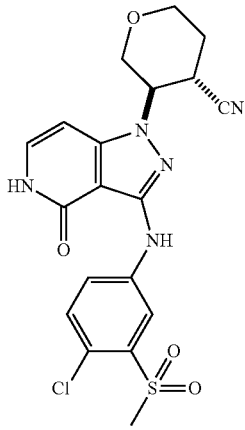

Step 1: (3R,4S)-3-(4-(benzyloxy)-3-((4-chloro-3-(methylthio)phenyl)amino)-1H-pyrazolo[4,3-c]pyridin-1-yl)tetrahydro-2H-pyran-4-carbonitrile (3-1a)

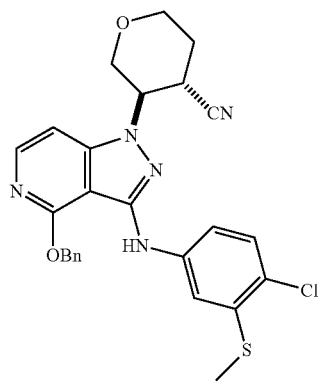

3-1a

To (3R,4S)-3-(3-amino-4-(benzyloxy)-1H-pyrazolo[4,3-c]pyridin-1-yl)tetrahydro-2H-pyran-4-carbonitrile (I-3B) (0.12 g, 0.34 mmol), (5-bromo-2-chlorophenyl)(methyl)sulfane (90 mg, 0.38 mmol), Pd$_2$dba$_3$ (38 mg, 0.041 mmol), potassium acetate (51 mg, 0.52 mmol), 2-di-tert-butylphosphino-3,4,5,6-tetramethyl-2',4',6'-triisopropyl-1,1'-biphenyl (35 mg, 0.082 mmol) in a degassed sealed microwave vial, was added propan-2-ol (3.5 mL) and the reaction was heated to 85° C. for 18 hours. The reaction was then concentrated in vacuo and purified by silica chromatography, eluting with 50-100% EtOAc in hexanes to afford the desired product 3-1a. LRMS (ESI) calc'd for $C_{26}H_{25}ClN_5O_2S$ [M+H]$^+$: 507, found 507.

Step 2: (3R,4S)-3-(3-((4-chloro-3-(methylthio)phenyl)amino)-4-oxo-4,5-dihydro-1H-pyrazolo[4,3-c]pyridin-1-yl)tetrahydro-2H-pyran-4-carbonitrile (3-1b)

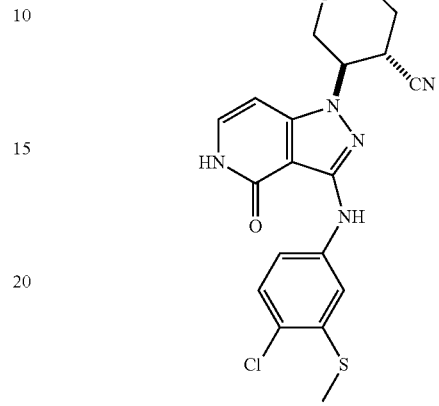

3-1b (3R,4S)-3-(4-(Benzyloxy)-3-((4-chloro-3-(methylthio)phenyl)amino)-1H-pyrazolo[4,3-c]pyridin-1-yl)tetrahydro-2H-pyran-4-carbonitrile (3-1a) (0.10 g, 0.20 mmol) was stirred in 1:1 DCM:TFA (2 mL) at ambient temperature for 16 hours. The mixture was then carefully diluted with saturated aqueous sodium bicarbonate and extracted with EtOAc. The organic layer was washed with brine, dried over anhydrous magnesium sulfate, filtered, and concentrated in vacuo to afford the title compound, 3-1b. The residue was carried forward without further purification. LRMS (ESI) calc'd for $C_{19}H_{19}ClN_5O_2S$ [M+H]$^+$: 416, found 416.

Step 3: (3R,4S)-3-(3-((4-chloro-3-(methylsulfonyl)phenyl)amino)-4-oxo-4,5-dihydro-1H-pyrazolo[4,3-c]pyridin-1-yl)tetrahydro-2H-pyran-4-carbonitrile To 3-1b (0.10 g, 0.24 mmol) in 1:1 DCM:EtOAc (9.6 mL) was added m-CPBA (54 mg, 0.24 mmol) at ambient temperature. The reaction mixture was stirred for 1 hour and then diluted with saturated aqueous sodium thiosulfate and extracted with EtOAc (×2). The combined organic extracts were washed with saturated aqueous sodium thiosulfate, dried over anhydrous magnesium sulfate, filtered and concentrated in vacuo. The residue was purified with reverse phase chromatography to afford compound 3-1. LRMS (ESI) calc'd for $C_{19}H_{19}ClN_5O_4S$ [M+H]$^+$: 448, found 448. $^1$H NMR (500 MHz, DMSO-d6): δ 11.18 (s, 1H); 8.82 (s, 1H); 8.72 (d, J=2.8 Hz, 1H); 7.94 (m, 1H); 7.56 (d, J=8.7 Hz, 1H); 7.26 (t, J=6.1 Hz, 1H); 6.75 (d, J=7.3 Hz, 1H); 4.88-4.96 (m, 1H); 3.92-4.04 (m, 2H); 3.72 (t, J=10.8 Hz, 1H); 3.55-3.63 (m, 1H); 3.33-3.43 (m, 4H); 2.15-2.25 (m, 1H); 1.97-2.07 (m, 1H).

The following examples outlined in Table 10 were prepared by analogy using the general procedure outlined above for Example 3-1 using the appropriate amount of m-CPBA to achieve mono oxidation of the sulfide.

TABLE 10

| Example | Structure | Compound Name | LRMS |
|---------|-----------|---------------|------|
| 3-2 | 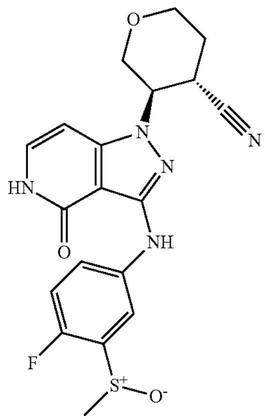 [SMILES: C[S+]([O-])c1cc(Nc2nn([C@H]3COCC[C@@H]3C#N)c3cc[nH]c(=O)c23)ccc1F] | (3R,4S)-3-(3-((4-fluoro-3-((S or R)-methylsulfinyl)phenyl)amino)-4-oxo-4,5-dihydro-1H-pyrazolo[4,3-c]pyridin-1-yl)tetrahydro-2H-pyran-4-carbonitrile (obtained via SFC separation of the diastereomeric mixture of sulfoxides on free pyridone using CHIRALPAK ® AD-H with 35%/65% (methanol/$CO_2$), peak 1, Tr = 3.8 mins.) | LRMS (ESI) calc'd for $C_{19}H_{19}FN_5O_3S$ $[M + H]^+$: 416, found 416. |
| 3-3 | 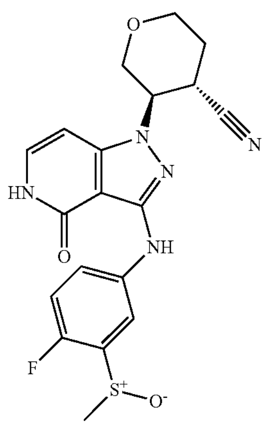 [SMILES: C[S+]([O-])c1cc(Nc2nn([C@H]3COCC[C@@H]3C#N)c3cc[nH]c(=O)c23)ccc1F] | (3R,4S)-3-(3-((4-fluoro-3-((S or R)-methylsulfinyl)phenyl)amino)-4-oxo-4,5-dihydro-1H-pyrazolo[4,3-c]pyridin-1-yl)tetrahydro-2H-pyran-4-carbonitrile (obtained via SFC separation of the diastereomeric mixture of sulfoxides on free pyridone using CHIRALPAK ® AD-H with 35%/65% (methanol/$CO_2$), peak 2, Tr = 6.1 mins.) | LRMS (ESI) calc'd for $C_{19}H_{19}FN_5O_3S$ $[M + H]^+$: 416, found 416. |
| 3-4 | 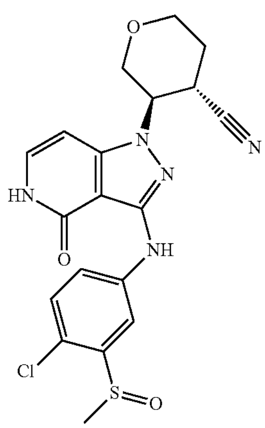 [SMILES: CS(=O)c1cc(Nc2nn([C@H]3COCC[C@@H]3C#N)c3cc[nH]c(=O)c23)ccc1Cl] | (3R,4S)-3-(3-{[4-chloro-3-((S and R) methylsulfinyl)phenyl]amino}-4-oxo-4,5-dihydro-1H-pyrazolo[4,3-c]pyridin-1-yl)tetrahydro-2H-pyran-4-carbonitrile | LRMS (ESI) calc'd for $C_{19}H_{19}ClN_5O_3S$ $[M + H]^+$: 432, found 432. |

BIOLOGICAL ASSAYS

Jak Biochemical HTRF Assay Protocol

The ability of compounds to inhibit the activity of JAK1, JAK2, JAK3, and TYK2 was measured using a recombinant purified GST-tagged catalytic domain for each enzyme (Invitrogen JAK1 #M4290, JAK2 #M4290, JAK3 #M4290, TYK2 #M4290) in an HTRF format biochemical assay. The reactions employed a common peptide substrate, LCB-EQEDEPEGDYFEWLW-NH2 (in-house). The basic assay protocol is as follows: First, 250 nL of diluted compounds in DMSO were dispensed into the wells of a dry 384-well Black plate (Greiner #781076) using a Labcyte Echo 555 acoustic dispenser. Subsequent reagent additions employed an Agilent Bravo. Next, 18 μL of 1.11× enzyme and 1.11× substrate in 1× assay buffer (Invitrogen kinase buffer # PV3189, 2 mM DTT, 0.05% BSA) were added to the wells and shaken and then preincubated for 30 minutes at room temperature to allow compound binding to equilibrate. After equilibration, 2 μL of 10×ATP in 1× assay buffer was added to initiate the kinase reaction and the plates were shaken and then incubated at room temperature for 120 minutes. At the end of the incubation, 20 μL of 2× stop buffer (streptavidin-Dylight 650 (Thermo #84547B/100 mL), Eu-tagged pY20 antibody (Perkin Elmer #AD0067), EDTA, HEPES, and Triton) was added to quench the reaction. Plates were shaken and centrifuged and then incubated 60 minutes at room temperature and then read on a Perkin Elmer Envision ($\lambda_{ex}$=337 nm, $\lambda_{em}$=665 and 615 nm, TRF delay time=20 µs). HTRF signal=10,000*665 nm reading/615 nm reading. After normalization to untreated controls, the percent inhibition of the HTRF signal at each compound concentration was calculated. The plot of percent inhibition versus the log of compound concentration was fit with a 4-parameter dose response equation to calculate $IC_{50}$ values.

Final reaction conditions were:

| Enzyme | [E] (nM) | [S] (µM) | [ATP] (µM) | [Eu-pY20] (nM) | [SA-Dylight] (nM) |
|---|---|---|---|---|---|
| JAK1 | 1.405 | 0.75 | 31.8 | 9 | 312.5 |
| JAK2 | 0.052 | 0.75 | 8.5 | 9 | 312.5 |
| JAK3 | 0.031 | 0.75 | 2.9 | 9 | 312.5 |
| TYK2 | 2.612 | 0.75 | 6.9 | 9 | 312.5 |

Compound concentrations tested were 1496, 499, 175, 49.9, 18.7, 6.2, 2.1, 0.75, 0.24, 0.075, and 0.0125 nM, with 1.25% residual DMSO.

BIOLOGICAL DATA

Examples of the instant invention were evaluated in JAK1 and JAK2 in vitro binding assays as described above. The following table tabulates the JAK1 $IC_{50}$ values and JAK2 $IC_{50}$ values disclosed for the instant invention.

| Example | JAK1 $IC_{50}$ | JAK2 $IC_{50}$ |
|---|---|---|
| 1-1 | 7.06 | 11.47 |
| 1-2 | 0.05 | 0.35 |
| 1-3 | 0.11 | 1.39 |
| 1-4 | 0.04 | 0.34 |
| 1-5 | 0.05 | 0.15 |
| 1-6 | 0.07 | 0.21 |
| 1-7 | 0.05 | 0.29 |
| 1-8 | 0.06 | 0.22 |
| 1-9 | 0.09 | 0.29 |
| 1-10 | 0.08 | 0.21 |
| 1-11 | 0.09 | 0.34 |
| 1-12 | 0.10 | 0.30 |
| 1-13 | 0.08 | 0.21 |
| 1-14 | 0.22 | 0.41 |
| 1-15 | 0.12 | 0.27 |
| 1-16 | 0.36 | 5.04 |
| 1-17 | 0.09 | 2.52 |
| 1-18 | 0.07 | 0.13 |
| 1-19 | 0.05 | 0.08 |
| 1-20 | 0.07 | 0.30 |
| 1-21 | 0.08 | 0.28 |
| 1-22 | 17.3 | 21.2 |
| 1-23 | 0.25 | 0.69 |
| 1-24 | 12.4 | 14.7 |
| 1-25 | 2.27 | 3.43 |
| 1-26 | 0.71 | 2.13 |
| 1-27 | 22.37 | 60.73 |
| 1-28 | 5.34 | 12.65 |
| 1-29 | 4.38 | 5.91 |
| 1-30 | 0.25 | 4.65 |
| 1-31 | 0.12 | 0.96 |
| 1-32 | 0.24 | 2.11 |
| 1-33 | 0.04 | 0.09 |
| 1-34 | 0.03 | 1.18 |
| 1-35 | 0.12 | 0.16 |
| 1-36 | 0.24 | 0.27 |
| 1-37 | 0.22 | 0.33 |
| 1-38 | 0.09 | 0.13 |
| 1-39 | 0.13 | 0.17 |
| 1-40 | 0.16 | 0.78 |
| 1-41 | 0.14 | 0.60 |
| 1-42 | 0.05 | 0.13 |
| 1-43 | 0.04 | 0.08 |
| 1-44 | 0.12 | 0.18 |
| 1-45 | 0.14 | 0.21 |
| 1-46 | 0.14 | 0.21 |
| 1-47 | 0.27 | 0.43 |
| 1-48 | 0.65 | 1.73 |
| 1-49 | 0.18 | 0.30 |
| 1-50 | 0.08 | 0.09 |
| 1-51 | 0.08 | 0.14 |
| 1-52 | 0.08 | 0.11 |
| 1-53 | 0.08 | 0.09 |
| 1-54 | 0.07 | 0.14 |
| 1-55 | 0.08 | 0.12 |
| 1-56 | 0.06 | 0.14 |
| 1-57 | 0.09 | 0.22 |
| 1-58 | 0.07 | 0.13 |
| 1-59 | 0.05 | 0.08 |
| 1-60 | 0.21 | 0.59 |
| 1-61 | 0.30 | 0.30 |
| 1-62 | 0.05 | 0.29 |
| 1-63 | 0.10 | 0.30 |
| 1-64 | 0.04 | 0.30 |
| 1-65 | 0.09 | 0.26 |
| 1-66 | 0.07 | 0.16 |
| 1-67 | 0.70 | 1.92 |
| 1-68 | 0.28 | 1.83 |
| 1-69 | 0.08 | 0.30 |
| 1-70 | 0.15 | 0.65 |
| 1-71 | 0.22 | 0.70 |
| 1-72 | 0.10 | 0.20 |
| 1-73 | 0.35 | 0.70 |
| 1-74 | 0.18 | 0.52 |
| 1-75 | 0.14 | 0.54 |
| 1-76 | 0.24 | 0.82 |
| 1-77 | 0.05 | 0.17 |
| 1-78 | 0.12 | 0.24 |
| 1-79 | 0.04 | 0.08 |
| 1-80 | 0.07 | 0.15 |
| 1-81 | 0.08 | 0.15 |
| 1-82 | 0.87 | 2.56 |
| 1-83 | 0.50 | 1.06 |
| 1-84 | 0.13 | 0.15 |
| 1-85 | 0.12 | 0.14 |
| 1-86 | 0.15 | 0.23 |
| 1-87 | 0.15 | 0.30 |
| 1-88 | 0.11 | 0.09 |
| 1-89 | 0.15 | 0.14 |
| 1-90 | 0.21 | 0.40 |
| 1-91 | 0.17 | 0.21 |
| 1-92 | 0.13 | 0.19 |
| 1-93 | 0.09 | 0.11 |
| 1-94 | 0.08 | 0.15 |
| 1-95 | 0.06 | 0.09 |
| 1-96 | 0.07 | 0.15 |
| 1-97 | 0.14 | 0.18 |
| 1-98 | 0.06 | 0.17 |
| 1-99 | 0.07 | 0.16 |
| 1-100 | 0.06 | 0.05 |
| 1-101 | 0.07 | 0.05 |
| 2-1 | 0.03 | 0.89 |
| 2-2 | 0.05 | 0.16 |
| 2-3 | 0.06 | 0.39 |
| 2-4 | 0.05 | 0.27 |
| 2-5 | 0.14 | 0.15 |
| 2-6 | 0.21 | 0.24 |
| 2-7 | 0.05 | 0.06 |
| 2-8 | 0.05 | 0.05 |
| 3-1 | 1.64 | 7.44 |
| 3-2 | 0.89 | 13.73 |
| 3-3 | 1.64 | 7.44 |
| 3-4 | 1.75 | 14.63 |

The invention claimed is:
1. A compound, or a pharmaceutically acceptable salt, or a stereoisomer thereof selected from:

3-(3-((4-(methyl sulfonyl)phenyl)amino)-4-oxo-4,5-dihydro-1H-pyrazolo[4,3-c]pyridin-1-yl)tetrahydro-2H-pyran-4-carbonitrile;

3-(4-oxo-3-(phenylamino)-4,5-dihydro-1H-pyrazolo[4,3-c]pyridin-1-yl)tetrahydro-2H-pyran-4-carbonitrile;

3-(3-((2-methyl-1,1-dioxido-2,3-dihydrobenzo[d]isothiazol-5-yl)amino)-4-oxo-4,5-dihydro-1H-pyrazolo[4,3-c]pyridin-1-yl)tetrahydro-2H-pyran-4-carbonitrile;

3-(3-((2-(tert-butyl)-1,1-dioxido-2,3-dihydrobenzo[d]isothiazol-5-yl)amino)-4-oxo-4,5-dihydro-1H-pyrazolo[4,3-c]pyridin-1-yl)tetrahydro-2H-pyran-4-carbonitrile;

4-((1-(4-cyanotetrahydro-2H-pyran-3-yl)-4-oxo-4, 5-dihydro-H-pyrazolo[4,3-c]pyridin-3-yl)amino)-N,N-dimethylbenzenesulfonamide;

3-(3-((1,1-dioxido-2-(2,2,2-trifluoroethyl)-2,3-dihydrobenzo[d]isothiazol-5-yl)amino)-4-oxo-4,5-dihydro-1H-pyrazolo[4,3-c]pyridin-1-yl)tetrahydro-2H-pyran-4-carbonitrile;

3-(3-((4-(1-amino-2,2,2-trifluoroethyl)phenyl)amino)-4-oxo-4, 5-dihydro-1H-pyrazolo[4,3-c]pyridin-1-yl)tetrahydro-2H-pyran-4-carbonitrile;

N-(tert-butyl)-4-((1-(4-cyanotetrahydro-2H-pyran-3-yl)-4-oxo-4, 5-dihydro 1H-pyrazolo[4,3-c]pyridin-3-yl)amino)benzenesulfonamide;

3-(3-((4-(isopropylsulfonyl)phenyl)amino)-4-oxo-4,5-dihydro-1H-pyrazolo[4,3-c]pyridin-1-yl)tetrahydro-2H-pyran-4-carbonitrile;

N-(tert-butyl)-4-((1-(4-cyanotetrahydro-2H-pyran-3-yl)-4-oxo-4, 5-dihydro 1H-pyrazolo[4,3-c]pyridin-3-yl)amino)-N-methylbenzenesulfonamide;

3-(3-((4-(tert-butyl sulfonyl)phenyl)amino)-4-oxo-4,5-dihydro-1H-pyrazolo[4,3-c]pyridin-1-yl)tetrahydro-2H-pyran-4-carbonitrile;

3-(3-{[2-(2-methylpropyl)-2,3-dihydro-1H-isoindol-5-yl]amino}-4-oxo-4,5-dihydro-1H-pyrazolo[4,3-c]pyridin-1-yl)tetrahydro-2H-pyran-4-carbonitrile;

3-(3-{[2-(1-methylethyl)-2,3-dihydro-1H-isoindol-5-yl]amino}-4-oxo-4,5-dihydro-1H-pyrazolo[4,3-c]pyridin-1-yl)tetrahydro-2H-pyran-4-carbonitrile;

methyl 5-({1-[4-cyanotetrahydro-2H-pyran-3-yl]-4-oxo-4,5-dihydro-1H-pyrazolo[4,3-c]pyridin-3-yl}amino)-2-hydroxybenzenecarboximidoate;

3-{3-[(4-fluoro-3-methoxyphenyl)amino]-4-oxo-4, 5-dihydro-1H-pyrazolo[4,3-c]pyridin-1-yl}tetrahydro-2H-pyran-4-carbonitrile;

3-[3-({4-[1-(dimethylamino)-2,2,2-trifluoroethyl]phenyl}amino)-4-oxo-4,5-dihydro-1H-pyrazolo[4,3-c]pyridin-1-yl]tetrahydro-2H-pyran-4-carbonitrile;

3-(3-{[4-(5,5-dimethyl-3-oxo-2-oxabicyclo[2.2.2]oct-1-yl)phenyl]amino}-4-oxo-4,5-dihydro-1H-pyrazolo[4,3-c]pyridin-1-yl)tetrahydro-2H-pyran-4-carbonitrile;

3-(3-{[4-(tert-butylsulfonyl)phenyl]amino}-4-oxo-4,5-dihydro-1H-pyrazolo[4,3-c]pyridin-1-yl)oxepane-4-carbonitrile;

3-(3-{[4-(tert-butylsulfonyl)phenyl]amino}-4-oxo-4,5-dihydro-1H-pyrazolo[4,3-c]pyridin-1-yl)oxepane-4-carbonitrile;

5-(3-{[4-(tert-butylsulfonyl)phenyl]amino}-4-oxo-4,5-dihydro-1H-pyrazolo[4,3-c]pyridin-1-yl)oxepane-4-carbonitrile;

5-(3-{[4-(tert-butyl sulfonyl)phenyl]amino}-4-oxo-4,5-dihydro-1H-pyrazolo[4,3-c]pyridin-1-yl)oxepane-4-carbonitrile;

3-{3-[(2-fluoropyridin-4-yl)amino]-4-oxo-4,5-dihydro-1H-pyrazolo[4,3-c]pyridin-1-yl}tetrahydro-2H-pyran-4-carbonitrile;

3-{3-[(4-cyanophenyl)amino]-4-oxo-4,5-dihydro-1H-pyrazolo[4,3-c]pyridin-1-yl}tetrahydro-2H-pyran-4-carbonitrile;

3-{3-[(4-cyano-3-fluorophenyl)amino]-4-oxo-4, 5-dihydro-1H-pyrazolo[4,3-c]pyridin-1-yl}tetrahydro-2H-pyran-4-carbonitrile;

3-(4-oxo-3-((4-((S or R)-1,1,1-trifluoro-2-methoxypropan-2-yl)phenyl)amino)-4,5-dihydro-1H-pyrazolo[4,3-c]pyridin-1-yl)tetrahydro-2H-pyran-4-carbonitrile;

3-(3-((2,3-dimethyl-1,1-dioxido-2,3-dihydrobenzo[d]isothiazol-5-yl)amino)-4-oxo-4,5-dihydro-1H-pyrazolo[4,3-c]pyridin-1-yl)tetrahydro-2H-pyran-4-carbonitrile;

3-(3-((4-(4,4-difluoropiperidine-1-carbonyl)-3-methylphenyl)amino)-4-oxo-4,5-dihydro-1H-pyrazolo[4,3-c]pyridin-1-yl)tetrahydro-2H-pyran-4-carbonitrile;

3-[4-oxo-3-({4-[2,2,2-trifluoro-1-(4-methylpiperazin-1-yl)ethyl]phenyl}amino)-4,5-dihydro-1H-pyrazolo[4,3-c]pyridin-1-yl]tetrahydro-2H-pyran-4-carbonitrile;

3-[4-oxo-3-({4-[2,2,2-trifluoro-1-piperazin-1-ylethyl]phenyl}amino)-4,5-dihydro-1H-pyrazolo[4,3-c]pyridin-1-yl]tetrahydro-2H-pyran-4-carbonitrile;

tert-butyl N-{1-[4-({1-[4-cyanotetrahydro-2H-pyran-3-yl]-4-oxo-4,5-dihydro-1H-pyrazolo[4,3-c]pyridin-3-yl}amino)phenyl]-2,2,2-trifluoroethyl}glycinate;

3-[4-oxo-3-({4-[2,2,2-trifluoro-1-pyrrolidin-1-ylethyl]phenyl}amino)-4,5-dihydro-1H-pyrazolo[4,3-c]pyridin-1-yl]tetrahydro-2H-pyran-4-carbonitrile;

3-[4-oxo-3-({4-[1-(2H-1,2,3-triazol-2-yl)ethyl]phenyl}amino)-4, 5-dihydro-1H-pyrazolo[4,3-c]pyridin-1-yl]tetrahydro-2H-pyran-4-carbonitrile;

3-{3-[{[(2,2-dimethylcyclopropyl)amino]-2,2,2-trifluoroethyl}phenyl)amino]-4-oxo-4,5-dihydro-1H-pyrazolo[4,3-c]pyridin-1-yl}tetrahydro-2H-pyran-4-carbonitrile;

3-[3-({4-[1-(tert-butylamino)-2,2,2-trifluoroethyl]phenyl})amino)-4-oxo-4,5-dihydro-1H-pyrazolo[4,3-c]pyridin-1-yl]tetrahydro-2H-pyran-4-carbonitrile;

3-{4-oxo-3-[(4-{2,2,2-trifluoro-1-[(1-methylethyl)amino]ethyl}phenyl)amino]-4,5-dihydro-1H-pyrazolo[4,3-c]pyridin-1-yl}tetrahydro-2H-pyran-4-carbonitrile;

3-[3-({4-[1-(ethylamino)-2,2,2-trifluoroethyl]phenyl}amino)-4-oxo-4,5-dihydro-1H-pyrazolo[4,3-c]pyridin-1-yl]tetrahydro-2H-pyran-4-carbonitrile;

3-[3-({4-[1-azetidin-1-yl-2,2,2-trifluoroethyl]phenyl}amino)-4-oxo-4,5-dihydro-1H-pyrazolo[4,3-c]pyridin-1-yl]tetrahydro-2H-pyran-4-carbonitrile;

3-[3-({4-[1-(dimethylamino)-2,2,2-trifluoroethyl]phenyl}amino)-4-oxo-4,5-dihydro-1H-pyrazolo[4,3-c]pyridin-1-yl]tetrahydro-2H-pyran-4-carbonitrile;

3-(3-{[4-(1-amino-1-methylethyl)phenyl]amino}-4-oxo-4,5-dihydro-1H-pyrazolo[4,3-c]pyridin-1-yl)tetrahydro-2H-pyran-4-carbonitrile;

3-{3-[(4-{1-methyl-1-[(1-methylethyl)amino]ethyl}phenyl)amino]-4-oxo-4,5-dihydro-1H-pyrazolo[4,3-c]pyridin-1-yl}tetrahydro-2H-pyran-4-carbonitrile;

3-(3-{[1,1-dioxido-2-(2,2,2-trifluoroethyl)-2,3-dihydro-1,2-benzisothiazol-5-yl]amino}-4-oxo-4,5-dihydro-1H-pyrazolo[4,3-c]pyridin-1-yl)tetrahydro-2H-pyran-4-carbonitrile;

N-tert-butyl-4-({1-[4-cyanotetrahydro-2H-pyran-3-yl]-4-oxo-4,5-dihydro-1H-pyrazolo[4,3-c]pyridin-3-yl}amino)-N-methylbenzenesulfonamide;

tert-butyl [5-({1-[4-cyanotetrahydro-2H-pyran-3-yl]-4-oxo-4,5-dihydro-1H-pyrazolo[4,3-c]pyridin-3-yl}amino)-1,1-dioxido-1,2-benzisothiazol-2(3H)-yl]acetate;

3-[3-({4-[(1,1-dimethylpropyl)sulfonyl]phenyl}amino)-4-oxo-4,5-dihydro-1H-pyrazolo[4,3-c]pyridin-1-yl]tetrahydro-2H-pyran-4-carbonitrile;

3-[4-oxo-3-({4-[(1,1,2-trimethylpropyl)sulfonyl]phenyl}amino)-4,5-dihydro-1H-pyrazolo[4,3-c]pyridin-1-yl]tetrahydro-2H-pyran-4-carbonitrile;

5-({1-[4-cyanotetrahydro-2H-pyran-3-yl]-4-oxo-4,5-dihydro-1H-pyrazolo[4,3-c]pyridin-3-yl}amino)-N,N-dimethylpyridine-2-sulfonamide;

3-{3-[(3,4-dimethylphenyl)amino]-4-oxo-4,5-dihydro-1H-pyrazolo[4,3-c]pyridin-1-yl}tetrahydro-2H-pyran-4-carbonitrile;

3-(3-{[4-(azetidin-1-ylsulfonyl)phenyl]amino}-4-oxo-4,5-dihydro-1H-pyrazolo[4,3-c]pyridin-1-yl)tetrahydro-2H-pyran-4-carbonitrile;

3-[3-({4-[(3-methylazetidin-1-yl)sulfonyl]phenyl}amino)-4-oxo-4,5-dihydro-1H-pyrazolo[4,3-c]pyridin-1-yl]tetrahydro-2H-pyran-4-carbonitrile;

3-[3-({4-[(2,2-dimethylmorpholin-4-yl)sulfonyl]phenyl}amino)-4-oxo-4,5-dihydro-1H-pyrazolo[4,3-c]pyridin-1-yl]tetrahydro-2H-pyran-4-carbonitrile;

3-[3-({4-[(2,2-dimethylpyrrolidin-1-yl)sulfonyl]phenyl}amino)-4-oxo-4,5-dihydro-1H-pyrazolo[4,3-c]pyridin-1-yl]tetrahydro-2H-pyran-4-carbonitrile;

3-{3-[(4-{[2,6-dimethylmorpholin-4-yl]sulfonyl}phenyl)amino]-4-oxo-4,5-dihydro-1H-pyrazolo[4,3-c]pyridin-1-yl}tetrahydro-2H-pyran-4-carbonitrile;

3-{3-[(4-{[2-methylmorpholin-4-yl]sulfonyl}phenyl)amino]-4-oxo-4, 5-dihydro-1H-pyrazolo[4,3-c]pyridin-1-yl}tetrahydro-2H-pyran-4-carbonitrile;

3-{3-[(4-{[2,6-dimethylmorpholin-4-yl]sulfonyl}phenyl)amino]-4-oxo-4,5-dihydro-1H-pyrazolo[4,3-c]pyridin-1-yl}tetrahydro-2H-pyran-4-carbonitrile;

3-{3-[(4-{[2-methylazetidin-1-yl]sulfonyl}phenyl)amino]-4-oxo-4,5-dihydro-1H-pyrazolo[4,3-c]pyridin-1-yl}tetrahydro-2H-pyran-4-carbonitrile;

N-(tert-butyl)-4-((1-(4-cyanotetrahydro-2H-pyran-3-yl)-4-oxo-4, 5-dihydro 1H-pyrazolo[4,3-c]pyridin-3-yl)amino)-N-ethylbenzenesulfonamide;

3-[3-({4-[1-(cyclopropylamino)-2,2,2-trifluoroethyl]phenyl}amino)-4-oxo-4,5 dihydro-1H-pyrazolo[4,3-c]pyridin-1-yl]tetrahydro-2H-pyran-4-carbonitrile;

3-{3-[(4-{1-[(2,2-dimethylpropyl)amino]-2,2,2-trifluoroethyl}phenyl)amino]-4-oxo-4,5-dihydro-1H-pyrazolo[4,3-c]pyridin-1-yl}tetrahydro-2H-pyran-4-carbonitrile;

3-[3-({4-[1-(cyclopentylamino)-2,2,2-trifluoroethyl]phenyl}amino)-4-oxo-4,5-dihydro-1H-pyrazolo[4,3-c]pyridin-1-yl]tetrahydro-2H-pyran-4-carbonitrile;

3-{4-oxo-3-[(4-{2,2,2-trifluoro-1-[2-methylpyrrolidin-1-yl]ethyl}phenyl)amino]-4,5-dihydro-1H-pyrazolo[4,3-c]pyridin-1-yl}tetrahydro-2H-pyran-4-carbonitrile;

3-{4-oxo-3-[(4-{2,2,2-trifluoro-1-[(2-methylpropyl)amino]ethyl}phenyl)amino]-4,5-dihydro-1H-pyrazolo[4,3-c]pyridin-1-yl}tetrahydro-2H-pyran-4-carbonitrile;

3-[3-({4-[1-(cyclobutylamino)-2,2,2-trifluoroethyl]phenyl}amino)-4-oxo-4,5-dihydro-1H-pyrazolo[4,3-c]pyridin-1-yl]tetrahydro-2H-pyran-4-carbonitrile;

3-(4-oxo-3-((4-(2,2,2-trifluoro-1-hydroxy-1-(pyridin-4-yl)ethyl)phenyl)amino)-4,5-dihydro-1H-pyrazolo[4,3-c]pyridin-1-yl)tetrahydro-2H-pyran-4-carbonitrile;

3-(4-oxo-3-((4-(2,2,2-trifluoro-1-hydroxy-1-(pyridin-2-yl)ethyl)phenyl)amino)-4,5-dihydro-1H-pyrazolo[4,3-c]pyridin-1-yl)tetrahydro-2H-pyran-4-carbonitrile;

3-(4-oxo-3-((4-((3-(trifluoromethyl)pyrrolidin-3-yl)phenyl)amino)-4, 5-dihydro-1H-pyrazolo[4,3-c]pyridin-1-yl)tetrahydro-2H-pyran-4-carbonitrile;

3-[3-({3-methyl-3-[(1-methylethyl)amino]-2-oxo-2,3-dihydro-1H-indol-6-yl}amino)-4-oxo-4, 5-dihydro-1H-pyrazolo[4,3-c]pyridin-1-yl]tetrahydro-2H-pyran-4-carbonitrile;

3-{3-[(2-methyl-1,3-benzothiazol-6-yl)amino]-4-oxo-4, 5-dihydro-H-pyrazolo[4,3-c]pyridin-1-yl}tetrahydro-2H-pyran-4-carbonitrile;

3-{3-[(3,3-dimethyl-2-oxo-2,3-dihydro-1H-indol-6-yl)amino]-4-oxo-4, 5-dihydro-1H-pyrazolo[4,3-c]pyridin-1-yl}tetrahydro-2H-pyran-4-carbonitrile;

3-[4-oxo-3-({4-[2,2,2-trifluoro-1-hydroxy-1-methylethyl]phenyl}amino)-4,5-dihydro-1H-pyrazolo[4,3-c]pyridin-1-yl]tetrahydro-2H-pyran-4-carbonitrile;

3-(3-((4-chloro-3-(methylsulfonyl)phenyl)amino)-4-oxo-4, 5-dihydro-1H-pyrazolo[4,3-c]pyridin-1-yl)tetrahydro-2H-pyran-4-carbonitrile;

3-(3-((4-fluoro-3-(methyl sulfinyl)phenyl)amino)-4-oxo-4, 5-dihydro-1H-pyrazolo[4,3-c]pyridin-1-yl)tetrahydro-2H-pyran-4-carbonitrile, and 3-(3-{[4-chloro-3-(methylsulfinyl)phenyl]amino}-4-oxo-4,5-dihydro-1H-pyrazolo[4,3-c]pyridin-1-yl)tetrahydro-2H-pyran-4-carbonitrile.

2. A pharmaceutical composition comprising a compound of claim 1 or a pharmaceutically acceptable salt thereof and a pharmaceutically acceptable carrier.

3. A method of treating a condition in a mammal that can be ameliorated by the inhibition of Janus kinases JAK1 and JAK 2 which condition is selected from, arthritis, asthma and obstructive airways diseases, autoimmune diseases or disorders, and cancer comprising administering to the mammal in need of such treatment, a therapeutically effective amount of a compound according to claim 1 or a pharmaceutically acceptable salt or a stereoisomer thereof.

4. A method according to claim 3, wherein said condition is arthritis.

5. A method according to claim 4, wherein said condition is selected from rheumatoid arthritis, juvenile arthritis, and psoriatic arthritis.

6. A method according to claim 3, wherein said condition is asthma or obstructive airways diseases.

7. A method according to claim 6, wherein said condition is selected from: chronic asthma, late asthma, airway hyperresponsiveness, bronchitis, bronchial asthma, allergic asthma, intrinsic asthma, extrinsic asthma, dust asthma, recurrent airway obstruction, and chronic obstruction pulmonary disease (COPD), and emphysema.

8. A method according to claim 3, wherein said condition is autoimmune diseases or disorders.

9. A method of treating asthma in a mammal in need thereof, comprising administering a therapeutically effective amount of a compound according to claim 1 or a pharmaceutically acceptable salt thereof.

10. A method of treating arthritis in a mammal in need thereof, comprising administering a therapeutically effective amount of a compound according to claim 1 or a pharmaceutically acceptable salt thereof.

11. A compound of claim 1, or a pharmaceutically acceptable salt thereof selected from:

(3R,4S)-3-[4-oxo-3-({4-[(1S)-2,2,2-trifluoro-1-(4-methylpiperazin-1-yl)ethyl]phenyl}amino)-4,5-dihydro-1H-pyrazolo[4,3-c]pyridin-1-yl]tetrahydro-2H-pyran-4-carbonitrile;

(3R,4S)-3-[4-oxo-3-({4-[(1R)-2,2,2-trifluoro-1-(4-methylpiperazin-1-yl)ethyl]phenyl}amino)-4,5-dihydro-1H-pyrazolo[4,3-c]pyridin-1-yl]tetrahydro-2H-pyran-4-carbonitrile;

(3R,4S)-3-[4-oxo-3-({4-[(1R)-2,2,2-trifluoro-1-piperazin-1-ylethyl]phenyl}amino)-4,5-dihydro-1H-pyrazolo[4,3-c]pyridin-1-yl]tetrahydro-2H-pyran-4-carbonitrile;

(3R,4S)-3-[4-oxo-3-({4-[(1S)-2,2,2-trifluoro-1-piperazin-1-ylethyl]phenyl}amino)-4,5-dihydro-1H-pyrazolo[4,3-c]pyridin-1-yl]tetrahydro-2H-pyran-4-carbonitrile;

(3R,4S)-3-[4-oxo-3-({4-[(1S)-2,2,2-trifluoro-1-piperazin-1-ylethyl]phenyl}amino)-4,5-dihydro-1H-pyrazolo[4,3-c]pyridin-1-yl]tetrahydro-2H-pyran-4-carbonitrile;

(3R,4S)-3-[4-oxo-3-({4-[(1R)-2,2,2-trifluoro-1-piperazin-1-ylethyl]phenyl}amino)-4,5-dihydro-1H-pyrazolo[4,3-c]pyridin-1-yl]tetrahydro-2H-pyran-4-carbonitrile;

tert-butyl N-{(1R)-1-[4-({1-[(3R,4S)-4-cyanotetrahydro-2H-pyran-3-yl]-4-oxo-4,5-dihydro-1H-pyrazolo[4,3-c]pyridin-3-yl}amino)phenyl]-2,2,2-trifluoroethyl}glycinate;

tert-butyl N-{(1S)-1-[4-({1-[(3R,4S)-4-cyanotetrahydro-2H-pyran-3-yl]-4-oxo-4,5-dihydro-1H-pyrazolo[4,3-c]pyridin-3-yl}amino)phenyl]-2,2,2-trifluoroethyl}glycinate;

tert-butyl N-{(1S)-1-[4-({1-[(3R,4S)-4-cyanotetrahydro-2H-pyran-3-yl]-4-oxo-4,5-dihydro-1H-pyrazolo[4,3-c]pyridin-3-yl}amino)phenyl]-2,2,2-trifluoroethyl}glycinate;

tert-butyl N-{(1R)-1-[4-({1-[(3R,4S)-4-cyanotetrahydro-2H-pyran-3-yl]-4-oxo-4,5-dihydro-1H-pyrazolo[4,3-c]pyridin-3-yl}amino)phenyl]-2,2,2-trifluoroethyl}glycinate;

(3R,4S)-3-[4-oxo-3-({4-[(1R)-2,2,2-trifluoro-1-pyrrolidin-1-ylethyl]phenyl}amino)-4,5-dihydro-1H-pyrazolo[4,3-c]pyridin-1-yl]tetrahydro-2H-pyran-4-carbonitrile;

(3R,4S)-3-[4-oxo-3-({4-[(1S)-2,2,2-trifluoro-1-pyrrolidin-1-ylethyl]phenyl}amino)-4,5-dihydro-1H-pyrazolo[4,3-c]pyridin-1-yl]tetrahydro-2H-pyran-4-carbonitrile;

(3R,4S)-3-[4-oxo-3-({4-[(1S)-2,2,2-trifluoro-1-pyrrolidin-1-ylethyl]phenyl}amino)-4,5-dihydro-1H-pyrazolo[4,3-c]pyridin-1-yl]tetrahydro-2H-pyran-4-carbonitrile;

(3R,4S)-3-[4-oxo-3-({4-[(1R)-2,2,2-trifluoro-1-pyrrolidin-1-ylethyl]phenyl}amino)-4,5-dihydro-1H-pyrazolo[4,3-c]pyridin-1-yl]tetrahydro-2H-pyran-4-carbonitrile;

(3R,4S)-3-[4-oxo-3-({4-[(1S)-1-(2H-1,2,3-triazol-2-yl)ethyl]phenyl}amino)-4,5-dihydro-1H-pyrazolo[4,3-c]pyridin-1-yl]tetrahydro-2H-pyran-4-carbonitrile;

(3R,4S)-3-[4-oxo-3-({4-[(1R)-1-(2H-1,2,3-triazol-2-yl)ethyl]phenyl}amino)-4,5-dihydro-1H-pyrazolo[4,3-c]pyridin-1-yl]tetrahydro-2H-pyran-4-carbonitrile;

(3R,4S)-3-[4-oxo-3-({4-[(1R)-1-(2H-1,2,3-triazol-2-yl)ethyl]phenyl}amino)-4,5-dihydro-1H-pyrazolo[4,3-c]pyridin-1-yl]tetrahydro-2H-pyran-4-carbonitrile;

(3R,4S)-3-[4-oxo-3-({4-[(1S)-1-(2H-1,2,3-triazol-2-yl)ethyl]phenyl}amino)-4,5-dihydro-1H-pyrazolo[4,3-c]pyridin-1-yl]tetrahydro-2H-pyran-4-carbonitrile;

(3R,4S)-3-{3-[(4S-{1S-[(2,2-dimethylcyclopropyl)amino]-2,2,2-trifluoroethyl}phenyl) amino]-4-oxo-4,5-dihydro-1H-pyrazolo[4,3-c]pyridin-1-yl}tetrahydro-2H-pyran-4-carbonitrile;

(3R,4S)-3-{3-[(4S-{1R-[(2,2-dimethylcyclopropyl)amino]-2,2,2-trifluoroethyl}phenyl) amino]-4-oxo-4,5-dihydro-1H-pyrazolo[4,3-c]pyridin-1-yl}tetrahydro-2H-pyran-4-carbonitrile;

(3R,4S)-3-{3-[(4S-{1S-[(2,2-dimethylcyclopropyl)amino]-2,2,2-trifluoroethyl}phenyl) amino]-4-oxo-4,5-dihydro-1H-pyrazolo[4,3-c]pyridin-1-yl}tetrahydro-2H-pyran-4-carbonitrile;

(3R,4S)-3-{3-[(4S-{1R-[(2,2-dimethylcyclopropyl)amino]-2,2,2-rifluoroethyl}phenyl) amino]-4-oxo-4,5-dihydro-1H-pyrazolo[4,3-c]pyridin-1-yl}tetrahydro-2H-pyran-4-carbonitrile;

(3R,4S)-3-{3-[(4R-{1S-[(2,2-dimethylcyclopropyl)amino]-2,2,2-rifluoroethyl}phenyl) amino]-4-oxo-4,5-dihydro-1H-pyrazolo[4,3-c]pyridin-1-yl}tetrahydro-2H-pyran-4-carbonitrile;

(3R,4S)-3-{3-[(4R-{1R-[(2,2-dimethylcyclopropyl)amino]-2,2,2-rifluoroethyl}phenyl) amino]-4-oxo-4,5-dihydro-1H-pyrazolo[4,3-c]pyridin-1-yl}tetrahydro-2H-pyran-4-carbonitrile;

(3R,4S)-3-{3-[(4S-{1S-[(2,2-dimethylcyclopropyl)amino]-2,2,2-trifluoroethyl}phenyl) amino]-4-oxo-4,5-dihydro-1H-pyrazolo[4,3-c]pyridin-1-yl}tetrahydro-2H-pyran-4-carbonitrile;

(3R,4S)-3-{3-[(4S-{1R-[(2,2-dimethylcyclopropyl)amino]-2,2,2-trifluoroethyl}phenyl) amino]-4-oxo-4,5-dihydro-1H-pyrazolo[4,3-c]pyridin-1-yl}tetrahydro-2H-pyran-4-carbonitrile;

(3R,4S)-3-{3-[(4R-{1S-[(2,2-dimethylcyclopropyl)amino]-2,2,2-trifluoroethyl}phenyl) amino]-4-oxo-4,5-dihydro-1H-pyrazolo[4,3-c]pyridin-1-yl}tetrahydro-2H-pyran-4-carbonitrile;

(3R,4S)-3-{3-[(4R-{1R-[(2,2-dimethylcyclopropyl)amino]-2,2,2-trifluoroethyl}phenyl) amino]-4-oxo-4,5-dihydro-1H-pyrazolo[4,3-c]pyridin-1-yl}tetrahydro-2H-pyran-4-carbonitrile;

(3R,4S)-3-{3-[(4S-{1S-[(2,2-dimethylcyclopropyl)amino]-2,2,2-trifluoroethyl}phenyl) amino]-4-oxo-4,5-dihydro-1H-pyrazolo[4,3-c]pyridin-1-yl}tetrahydro-2H-pyran-4-carbonitrile;

(3R,4S)-3-{3-[(4S-{1R-[(2,2-dimethylcyclopropyl)amino]-2,2,2-trifluoroethyl}phenyl) amino]-4-oxo-4,5-dihydro-1H-pyrazolo[4,3-c]pyridin-1-yl}tetrahydro-2H-pyran-4-carbonitrile;

(3R,4S)-3-{3-[(4R-{1S-[(2,2-dimethylcyclopropyl)amino]-2,2,2-trifluoroethyl}phenyl) amino]-4-oxo-4,5-dihydro-1H-pyrazolo[4,3-c]pyridin-1-yl}tetrahydro-2H-pyran-4-carbonitrile; or (3R,4S)-3-{3-[(4R-{1R-[(2,2-dimethylcyclopropyl)amino]-2,2,2-trifluoroethyl}phenyl) amino]-4-oxo-4,5-dihydro-1H-pyrazolo[4,3-c]pyridin-1-yl}tetrahydro-2H-pyran-4-carbonitrile.

* * * * *